United States Patent
Dehghani et al.

(10) Patent No.: US 12,416,798 B2
(45) Date of Patent: Sep. 16, 2025

(54) SYSTEMS AND METHODS FOR MEDICAL IMAGING

(71) Applicant: Activ Surgical, Inc., Boston, MA (US)

(72) Inventors: Hossein Dehghani, Boston, MA (US); Vasiliy E. Buharin, Boston, MA (US); Roman Stolyarov, Boston, MA (US); Thomas Calef, Boston, MA (US); Liam O'Shea, Boston, MA (US); Alexander J. Dye, Boston, MA (US); Chris J. Situ, Boston, MA (US)

(73) Assignee: ACTIV Surgical, Inc., Boston, MA (US)

( * ) Notice: Subject to any disclaimer, the term of this patent is extended or adjusted under 35 U.S.C. 154(b) by 0 days.

(21) Appl. No.: 18/614,393

(22) Filed: Mar. 22, 2024

(65) Prior Publication Data

US 2024/0353669 A1    Oct. 24, 2024

Related U.S. Application Data

(63) Continuation of application No. 17/673,324, filed on Feb. 16, 2022, now Pat. No. 11,977,218, which is a
(Continued)

(51) Int. Cl.
*G02B 23/24* (2006.01)
*A61B 1/06* (2006.01)
(Continued)

(52) U.S. Cl.
CPC .......... *G02B 23/2423* (2013.01); *A61B 1/06* (2013.01); *H04N 23/45* (2023.01); *H04N 23/55* (2023.01); *H04N 23/58* (2023.01)

(58) Field of Classification Search
CPC .......... G02B 23/2423; G02B 27/48; G02B 23/2484; G02B 23/2415; G02B 23/2476;
(Continued)

(56) References Cited

U.S. PATENT DOCUMENTS

| | | |
|---|---|---|
| 4,349,014 A | 9/1982 | Takamatsu |
| 4,576,456 A | 3/1986 | Okino |

(Continued)

FOREIGN PATENT DOCUMENTS

| | | |
|---|---|---|
| CN | 102770071 A | 11/2012 |
| CN | 103169446 A | 6/2013 |

(Continued)

OTHER PUBLICATIONS

Bray et al. Endoscopic laser speckle imaging of tissue blood flow: applications in the human knee. Journal of Orthopaedic Research, pp. 1650-1659 (2006).

(Continued)

*Primary Examiner* — John W Miller
*Assistant Examiner* — Omer Khalid
(74) *Attorney, Agent, or Firm* — Cesariand McKenna, LLP

(57) ABSTRACT

The present disclosure provides systems and methods for medical imaging. The system may comprise a scope assembly. The scope assembly may comprise a housing unit configured to releasably couple to at least a portion of an elongated scope. The scope assembly may comprise an imaging unit operably coupled to the housing unit, wherein the imaging unit comprises an optics assembly configured to (i) receive one or more light beams that are transmitted through the elongated scope and (ii) direct at least a portion of the one or more light beams onto two or more locations within a subject's body. At least one of the two or more locations may comprise a target site. The imaging unit may be configured to move via a rotational and/or translational motion relative to the housing unit to alter a field of view when imaging within the subject's body.

20 Claims, 29 Drawing Sheets

Related U.S. Application Data continuation of application No. PCT/US2020/047275, filed on Aug. 20, 2020.

(60) Provisional application No. 62/889,863, filed on Aug. 21, 2019, provisional application No. 62/953,724, filed on Dec. 26, 2019, provisional application No. 62/960,897, filed on Jan. 14, 2020.

(51) Int. Cl.
*H04N 23/45* (2023.01)
*H04N 23/55* (2023.01)
*H04N 23/58* (2023.01)

(58) Field of Classification Search
CPC ......... A61B 1/06; A61B 1/00126; A61B 1/05; H04N 23/45; H04N 23/55; H04N 23/58
USPC .......................................................... 348/79
See application file for complete search history.

(56) References Cited

U.S. PATENT DOCUMENTS

| | | |
|---|---|---|
| 4,592,632 A | 6/1986 | Renold |
| 4,844,071 A | 7/1989 | Chen et al. |
| 4,974,076 A | 11/1990 | Nakamura |
| 5,748,930 A | 5/1998 | Prakash |
| 5,749,830 A | 5/1998 | Kaneko |
| 5,980,450 A | 11/1999 | Thompson |
| 6,069,698 A | 5/2000 | Ozawa et al. |
| 6,088,105 A | 7/2000 | Link |
| 6,373,963 B1 | 4/2002 | Demers et al. |
| 6,438,302 B1 | 8/2002 | Utsui |
| 6,491,702 B2 | 12/2002 | Heilbrun et al. |
| 6,503,195 B1 | 1/2003 | Keller et al. |
| 6,537,211 B1 | 3/2003 | Wang |
| 6,542,249 B1 | 4/2003 | Kofman et al. |
| 6,549,288 B1 | 4/2003 | Migdal et al. |
| 6,563,105 B2 | 5/2003 | Seibel et al. |
| 6,564,086 B2 | 5/2003 | Marchitto et al. |
| 6,613,041 B1 | 9/2003 | Schrunder |
| 6,635,011 B1 | 10/2003 | Ozawa |
| 6,697,164 B1 | 2/2004 | Babayoff et al. |
| 6,800,057 B2 | 10/2004 | Tsujita et al. |
| 6,850,872 B1 | 2/2005 | Marschner et al. |
| 6,873,867 B2 | 3/2005 | Vilsmeier |
| 6,885,464 B1 | 4/2005 | Pfeiffer et al. |
| RE38,800 E | 9/2005 | Barbour |
| 6,965,690 B2 | 11/2005 | Matsumoto |
| 6,977,732 B2 | 12/2005 | Chen et al. |
| 6,987,531 B2 | 1/2006 | Kamon |
| 7,006,236 B2 | 2/2006 | Tomasi et al. |
| 7,068,825 B2 | 6/2006 | Rubbert et al. |
| 7,092,107 B2 | 8/2006 | Babayoff et al. |
| 7,099,732 B2 | 8/2006 | Geng |
| 7,124,066 B2 | 10/2006 | Marschner et al. |
| 7,152,024 B2 | 12/2006 | Marschner et al. |
| 7,184,150 B2 | 2/2007 | Quadling et al. |
| 7,200,262 B2 | 4/2007 | Sawada |
| 7,224,384 B1 | 5/2007 | Iddan et al. |
| 7,230,725 B2 | 6/2007 | Babayoff et al. |
| 7,242,997 B2 | 7/2007 | Geng |
| 7,305,110 B2 | 12/2007 | Rubbert et al. |
| 7,313,264 B2 | 12/2007 | Crampton |
| 7,319,529 B2 | 1/2008 | Babayoff |
| 7,363,201 B2 | 4/2008 | Marschner et al. |
| 7,385,708 B2 | 6/2008 | Ackerman et al. |
| 7,433,807 B2 | 10/2008 | Marschner et al. |
| 7,435,217 B2 | 10/2008 | Wiklof |
| 7,450,783 B2 | 11/2008 | Talapov et al. |
| 7,477,402 B2 | 1/2009 | Babayoff et al. |
| 7,489,408 B2 | 2/2009 | Harding et al. |
| 7,491,956 B2 | 2/2009 | Knoche et al. |
| 7,492,927 B2 | 2/2009 | Marschner et al. |
| 7,511,829 B2 | 3/2009 | Babayoff |
| 7,522,764 B2 | 4/2009 | Schwotzer |
| 7,577,299 B2 | 8/2009 | Kawamata et al. |
| 7,620,209 B2 | 11/2009 | Stevick et al. |
| 7,630,089 B2 | 12/2009 | Babayoff et al. |
| 7,704,206 B2 | 4/2010 | Suzuki et al. |
| 7,724,378 B2 | 5/2010 | Babayoff |
| 7,724,932 B2 | 5/2010 | Ernst et al. |
| 7,751,871 B2 | 7/2010 | Rubbert |
| 7,763,841 B1 | 7/2010 | McEldowney |
| 7,794,388 B2 | 9/2010 | Draxinger et al. |
| 7,821,649 B2 | 10/2010 | Bendall et al. |
| 7,854,700 B2 | 12/2010 | Orihara |
| 7,898,651 B2 | 3/2011 | Hu et al. |
| 7,944,569 B2 | 5/2011 | Babayoff et al. |
| 7,951,073 B2 | 5/2011 | Freed |
| 7,961,912 B2 | 6/2011 | Stevick et al. |
| 7,967,743 B2 | 6/2011 | Ishihara |
| 7,990,548 B2 | 8/2011 | Babayoff et al. |
| 7,995,798 B2 | 8/2011 | Krupnik et al. |
| 8,027,710 B1 | 9/2011 | Dannan |
| 8,038,609 B2 | 10/2011 | Kohno et al. |
| 8,084,753 B2 | 12/2011 | Joshi et al. |
| 8,194,122 B2 | 6/2012 | Amling et al. |
| 8,264,536 B2 | 9/2012 | McEldowney |
| 8,279,418 B2 | 10/2012 | Yee et al. |
| 8,280,152 B2 | 10/2012 | Thiel et al. |
| 8,310,683 B2 | 11/2012 | Babayoff et al. |
| 8,320,621 B2 | 11/2012 | McEldowney |
| 8,326,020 B2 | 12/2012 | Lee et al. |
| 8,330,804 B2 | 12/2012 | Lutian et al. |
| 8,400,494 B2 | 3/2013 | Zalevsky et al. |
| 8,406,859 B2 | 3/2013 | Zuzak et al. |
| 8,471,897 B2 | 6/2013 | Rodriguez Ramos et al. |
| 8,517,928 B2 | 8/2013 | Orihara |
| 8,553,939 B2 | 10/2013 | Craig et al. |
| 8,558,873 B2 | 10/2013 | McEldowney |
| 8,593,507 B2 | 11/2013 | Yahav |
| 8,610,665 B2 | 12/2013 | Craig et al. |
| 8,649,024 B2 | 2/2014 | Colonna De Lega |
| 8,659,765 B2 | 2/2014 | Ando |
| 8,723,118 B2 | 5/2014 | McEldowney et al. |
| 8,723,923 B2 | 5/2014 | Bloom et al. |
| 8,755,053 B2 | 6/2014 | Fright et al. |
| 8,792,098 B2 | 7/2014 | Dewald et al. |
| 8,803,952 B2 | 8/2014 | Katz et al. |
| 8,823,790 B2 | 9/2014 | Dunn et al. |
| 8,891,087 B2 | 11/2014 | Zuzak et al. |
| 8,896,594 B2 | 11/2014 | Xiong et al. |
| 8,974,378 B2 | 3/2015 | Imaizumi et al. |
| 9,001,190 B2 | 4/2015 | Olivier, III et al. |
| 9,057,784 B2 | 6/2015 | Hudman |
| 9,068,824 B2 | 6/2015 | Findeisen et al. |
| 9,070,194 B2 | 6/2015 | Lee et al. |
| 9,072,445 B2 | 7/2015 | Berguer et al. |
| 9,074,868 B2 | 7/2015 | Bendall et al. |
| 9,089,277 B2 | 7/2015 | Babayoff et al. |
| 9,119,552 B2 | 9/2015 | Baumann et al. |
| 9,135,502 B2 | 9/2015 | Haker et al. |
| 9,142,025 B2 | 9/2015 | Park et al. |
| 9,147,253 B2 | 9/2015 | Yee et al. |
| 9,149,348 B2 | 10/2015 | Wu et al. |
| 9,155,480 B2 | 10/2015 | Thakor et al. |
| 9,157,728 B2 | 10/2015 | Ogawa |
| 9,157,733 B2 | 10/2015 | Dillon et al. |
| 9,198,578 B2 | 12/2015 | Zuzak et al. |
| 9,204,952 B2 | 12/2015 | Lampalzer |
| 9,220,570 B2 | 12/2015 | Kim et al. |
| 9,226,645 B2 | 1/2016 | Ntziachristos |
| 9,226,673 B2 | 1/2016 | Ferguson, Jr. et al. |
| 9,247,865 B2 | 2/2016 | Igarashi et al. |
| 9,254,076 B2 | 2/2016 | McDowall |
| 9,254,078 B2 | 2/2016 | McDowall |
| 9,254,103 B2 | 2/2016 | Krishnaswamy et al. |
| 9,261,356 B2 | 2/2016 | Lampert et al. |
| 9,261,358 B2 | 2/2016 | Atiya et al. |
| 9,271,633 B2 | 3/2016 | Scott et al. |
| 9,271,658 B2 | 3/2016 | Ferguson, Jr. et al. |
| 9,274,047 B2 | 3/2016 | Velten et al. |
| 9,282,926 B2 | 3/2016 | Schwotzer et al. |

(56) References Cited

U.S. PATENT DOCUMENTS

| | | |
|---|---|---|
| 9,294,758 B2 | 3/2016 | Xiong et al. |
| 9,297,889 B2 | 3/2016 | Hudman et al. |
| 9,304,603 B2 | 4/2016 | Miller |
| 9,330,464 B1 | 5/2016 | Ackerman et al. |
| 9,345,389 B2 | 5/2016 | Nie et al. |
| 9,345,392 B2 | 5/2016 | Saito |
| 9,345,397 B2 | 5/2016 | Taylor et al. |
| 9,351,643 B2 | 5/2016 | Sharonov |
| 9,364,300 B2 | 6/2016 | Tchouprakov et al. |
| 9,375,844 B2 | 6/2016 | Itkowitz et al. |
| 9,377,295 B2 | 6/2016 | Fright et al. |
| 9,380,224 B2 | 6/2016 | Keskin et al. |
| 9,389,068 B2 | 7/2016 | Ri |
| 9,404,741 B2 | 8/2016 | Schick |
| 9,432,593 B2 | 8/2016 | Yang et al. |
| 9,439,568 B2 | 9/2016 | Atiya et al. |
| 9,443,310 B2 | 9/2016 | Hudman et al. |
| 9,444,981 B2 | 9/2016 | Bellis et al. |
| 9,451,872 B2 | 9/2016 | Yokota |
| 9,462,253 B2 | 10/2016 | Hudman et al. |
| 9,471,864 B2 | 10/2016 | Zatloukal et al. |
| 9,491,441 B2 | 11/2016 | Sarmast et al. |
| 9,494,418 B2 | 11/2016 | Schmidt |
| 9,506,749 B2 | 11/2016 | Bellis et al. |
| 9,513,113 B2 | 12/2016 | Yang et al. |
| 9,513,768 B2 | 12/2016 | Zhao et al. |
| 9,545,220 B2 | 1/2017 | Sidlesky |
| 9,554,692 B2 | 1/2017 | Levy |
| 9,557,574 B2 | 1/2017 | McEldowney |
| 9,581,802 B2 | 2/2017 | Yokota |
| 9,615,901 B2 | 4/2017 | Babayoff et al. |
| 9,622,644 B2 | 4/2017 | Yokota |
| 9,622,662 B2 | 4/2017 | Zuzak et al. |
| 9,638,801 B2 | 5/2017 | Boufounos et al. |
| 9,674,436 B2 | 6/2017 | Crane et al. |
| 9,675,429 B2 | 6/2017 | Lampert et al. |
| 9,690,984 B2 | 6/2017 | Butler et al. |
| 9,696,427 B2 | 7/2017 | Wilson et al. |
| 9,720,506 B2 | 8/2017 | Kim et al. |
| 9,729,860 B2 | 8/2017 | Cohen et al. |
| 9,737,239 B2 | 8/2017 | Kimmel |
| 9,739,594 B2 | 8/2017 | Koerner et al. |
| 9,746,318 B2 | 8/2017 | Sugano |
| 9,752,867 B2 | 9/2017 | Atiya et al. |
| 9,782,056 B2 | 10/2017 | McDowall |
| 9,788,903 B2 | 10/2017 | Kim et al. |
| 9,799,117 B2 | 10/2017 | Chen et al. |
| 9,817,159 B2 | 11/2017 | Hudman |
| 9,833,145 B2 | 12/2017 | Jeong et al. |
| 9,841,496 B2 | 12/2017 | Hudman |
| 9,844,427 B2 | 12/2017 | Atiya et al. |
| 9,901,409 B2 | 2/2018 | Yang et al. |
| 9,918,640 B2 | 3/2018 | Ntziachristos et al. |
| 9,922,249 B2 | 3/2018 | Kang et al. |
| 9,939,258 B2 | 4/2018 | Lampert et al. |
| 9,943,271 B2 | 4/2018 | Dirauf et al. |
| 9,947,099 B2 | 4/2018 | Bleyer et al. |
| 9,953,428 B2 | 4/2018 | Gren et al. |
| 9,955,140 B2 | 4/2018 | Rhemann et al. |
| 9,955,861 B2 | 5/2018 | Gao et al. |
| 9,958,585 B2 | 5/2018 | Powell et al. |
| 9,958,758 B2 | 5/2018 | Hudman |
| 9,962,244 B2 | 5/2018 | Esbech et al. |
| 9,970,753 B2 | 5/2018 | Han et al. |
| 10,011,014 B2 | 7/2018 | Divoky et al. |
| 10,018,464 B2 | 7/2018 | Boles et al. |
| 10,024,968 B2 | 7/2018 | Hudman et al. |
| 10,039,439 B2 | 8/2018 | Aoyama |
| 10,045,882 B2 | 8/2018 | Balicki et al. |
| 10,055,856 B2 | 8/2018 | Sabater et al. |
| 10,058,256 B2 | 8/2018 | Chen et al. |
| 10,066,997 B2 | 9/2018 | Korner et al. |
| 10,089,737 B2 | 10/2018 | Krieger et al. |
| 10,169,862 B2 | 1/2019 | Andre et al. |
| 10,244,991 B2 | 4/2019 | Shademan et al. |
| 10,390,718 B2 | 8/2019 | Chen et al. |
| 10,398,519 B2 | 9/2019 | Kim et al. |
| 10,575,737 B2 | 3/2020 | Andre et al. |
| 10,675,040 B2 | 6/2020 | Kim et al. |
| 10,681,259 B2 | 6/2020 | Ichiki et al. |
| 10,694,117 B2 | 6/2020 | Frangioni |
| 10,722,173 B2 | 7/2020 | Chen et al. |
| 10,792,492 B2 | 10/2020 | Chen et al. |
| 10,925,465 B2 | 2/2021 | Tully et al. |
| 10,948,350 B2 | 3/2021 | Ferguson, Jr. et al. |
| 10,966,597 B2 | 4/2021 | Yamazoe et al. |
| 11,135,028 B2 | 10/2021 | Kim et al. |
| 11,278,220 B2 | 3/2022 | Tucker et al. |
| 11,389,051 B2 | 7/2022 | Tully et al. |
| 11,754,828 B2 | 9/2023 | Tully et al. |
| 11,977,218 B2 | 5/2024 | Dehghani et al. |
| 2001/0030983 A1 | 10/2001 | Yuri et al. |
| 2002/0021355 A1 | 2/2002 | Utsui |
| 2002/0022768 A1 | 2/2002 | Utsui |
| 2003/0050532 A1 | 3/2003 | Doguchi |
| 2003/0176768 A1 | 9/2003 | Gono |
| 2003/0195623 A1 | 10/2003 | Marchitto et al. |
| 2004/0257438 A1 | 12/2004 | Doguchi |
| 2005/0010084 A1 | 1/2005 | Tsai |
| 2005/0096515 A1 | 5/2005 | Geng |
| 2005/0220447 A1 | 10/2005 | Ito |
| 2005/0267329 A1 | 12/2005 | Konstorum et al. |
| 2006/0173240 A1 | 8/2006 | Fukuyama |
| 2007/0055103 A1 | 3/2007 | Hoefig et al. |
| 2007/0115484 A1 | 5/2007 | Huang et al. |
| 2007/0146719 A1 | 6/2007 | Wedel |
| 2007/0165243 A1 | 7/2007 | Kang et al. |
| 2007/0276185 A1 | 11/2007 | Gono |
| 2007/0280423 A1 | 12/2007 | Schmidt |
| 2008/0107305 A1 | 5/2008 | Vanderkooy et al. |
| 2008/0218826 A1 | 9/2008 | DeSaulniers |
| 2008/0266391 A1 | 10/2008 | Lee et al. |
| 2009/0216085 A1 | 8/2009 | Yamazaki |
| 2009/0221874 A1 | 9/2009 | Vinther et al. |
| 2009/0244260 A1 | 10/2009 | Takahashi et al. |
| 2009/0289200 A1 | 11/2009 | Ishii |
| 2010/0097454 A1 | 4/2010 | Kubo |
| 2010/0113921 A1 | 5/2010 | Fear et al. |
| 2010/0210904 A1 | 8/2010 | Cline et al. |
| 2011/0015518 A1 | 1/2011 | Schmidt et al. |
| 2011/0043609 A1 | 2/2011 | Choi et al. |
| 2011/0057930 A1 | 3/2011 | Keller et al. |
| 2011/0069162 A1 | 3/2011 | Ozawa et al. |
| 2011/0071352 A1 | 3/2011 | Ozawa et al. |
| 2011/0080471 A1 | 4/2011 | Song et al. |
| 2011/0115882 A1 | 5/2011 | Shahinian |
| 2011/0123098 A1 | 5/2011 | Ernst et al. |
| 2011/0245844 A1* | 10/2011 | Jinno .................. A61B 34/30 606/130 |
| 2012/0075432 A1 | 3/2012 | Bilbrey et al. |
| 2012/0095354 A1 | 4/2012 | Dunn et al. |
| 2012/0101348 A1 | 4/2012 | Yamaguchi et al. |
| 2012/0165681 A1 | 6/2012 | Keller |
| 2012/0206587 A1 | 8/2012 | Oz et al. |
| 2012/0307512 A1 | 12/2012 | Cogger et al. |
| 2012/0310098 A1 | 12/2012 | Popovic |
| 2013/0023732 A1 | 1/2013 | Kim et al. |
| 2013/0041267 A1 | 2/2013 | Ntziachristos et al. |
| 2013/0253313 A1 | 9/2013 | Kang et al. |
| 2013/0274596 A1 | 10/2013 | Azizian et al. |
| 2013/0296712 A1 | 11/2013 | Durvasula |
| 2014/0031665 A1 | 1/2014 | Pinto et al. |
| 2014/0051923 A1 | 2/2014 | Mirza et al. |
| 2014/0052005 A1 | 2/2014 | Yokota |
| 2014/0071257 A1 | 3/2014 | Yokota |
| 2014/0092281 A1 | 4/2014 | Nisenzon et al. |
| 2014/0194747 A1 | 7/2014 | Kruglick et al. |
| 2014/0221749 A1 | 8/2014 | Grant et al. |
| 2014/0309495 A1 | 10/2014 | Kirma et al. |
| 2014/0378845 A1 | 12/2014 | Nadkarni |
| 2015/0099925 A1 | 4/2015 | Davidson et al. |
| 2015/0164329 A1 | 6/2015 | Schmidt et al. |
| 2015/0238276 A1 | 8/2015 | Atarot et al. |
| 2015/0377613 A1 | 12/2015 | Small et al. |

(56) References Cited

U.S. PATENT DOCUMENTS

| | | |
|---|---|---|
| 2015/0381909 A1 | 12/2015 | Butte et al. |
| 2016/0100908 A1 | 4/2016 | Tesar |
| 2016/0128553 A1 | 5/2016 | Geng |
| 2016/0139039 A1 | 5/2016 | Ikehara et al. |
| 2016/0239978 A1 | 8/2016 | Cole et al. |
| 2016/0260206 A1 | 9/2016 | Jung et al. |
| 2016/0262615 A1 | 9/2016 | Jung et al. |
| 2016/0278678 A1 | 9/2016 | Valdes et al. |
| 2016/0300348 A1 | 10/2016 | Nadeau et al. |
| 2016/0302880 A1 | 10/2016 | Uhlemann et al. |
| 2016/0307325 A1 | 10/2016 | Wang et al. |
| 2016/0307326 A1 | 10/2016 | Wang |
| 2016/0309068 A1 | 10/2016 | Nadeau et al. |
| 2016/0335472 A1 | 11/2016 | Lee et al. |
| 2017/0014030 A1 | 1/2017 | Rentschler et al. |
| 2017/0020393 A1 | 1/2017 | Rentschler et al. |
| 2017/0026633 A1 | 1/2017 | Riza |
| 2017/0030710 A1 | 2/2017 | Rentschler et al. |
| 2017/0032531 A1 | 2/2017 | Nagata et al. |
| 2017/0059305 A1 | 3/2017 | Nonn et al. |
| 2017/0059849 A1 | 3/2017 | Daidoji et al. |
| 2017/0079724 A1 | 3/2017 | Yang et al. |
| 2017/0095299 A1 | 4/2017 | Hendrick et al. |
| 2017/0100024 A1 | 4/2017 | Shahmoon et al. |
| 2017/0143237 A1 | 5/2017 | Yokota |
| 2017/0155818 A1 | 6/2017 | Bonnet |
| 2017/0164836 A1 | 6/2017 | Krishnaswamy et al. |
| 2017/0172382 A1 | 6/2017 | Nir et al. |
| 2017/0172384 A1 | 6/2017 | Yokota |
| 2017/0172394 A1 | 6/2017 | Scott et al. |
| 2017/0209031 A1 | 7/2017 | Nakamura et al. |
| 2017/0224274 A1 | 8/2017 | Chen et al. |
| 2017/0227942 A1 | 8/2017 | Thomson et al. |
| 2017/0228879 A1 | 8/2017 | Sato |
| 2017/0251900 A1 | 9/2017 | Hansen et al. |
| 2017/0280970 A1 | 10/2017 | Sartor et al. |
| 2017/0311778 A1 | 11/2017 | Hasser et al. |
| 2017/0328704 A1 | 11/2017 | Atiya et al. |
| 2017/0347043 A1 | 11/2017 | Rephaeli et al. |
| 2017/0351103 A1 | 12/2017 | Duckett et al. |
| 2017/0366773 A1 | 12/2017 | Kiraly et al. |
| 2018/0003943 A1 | 1/2018 | Chan |
| 2018/0008371 A1 | 1/2018 | Manus |
| 2018/0042466 A1 | 2/2018 | Kang et al. |
| 2018/0047165 A1 | 2/2018 | Sato |
| 2018/0104009 A1 | 4/2018 | Abhari et al. |
| 2018/0125586 A1 | 5/2018 | Sela et al. |
| 2018/0165823 A1 | 6/2018 | Ludwig |
| 2018/0174318 A1 | 6/2018 | Wang et al. |
| 2018/0235715 A1 | 8/2018 | Amiot et al. |
| 2018/0243043 A1 | 8/2018 | Michihata et al. |
| 2018/0279954 A1* | 10/2018 | Hayam .................. A61B 5/363 |
| 2018/0360299 A1 | 12/2018 | Kishima |
| 2019/0000308 A1 | 1/2019 | Duckett, III et al. |
| 2019/0239730 A1 | 8/2019 | Myung et al. |
| 2019/0246873 A1* | 8/2019 | Lu ...................... A61B 1/00124 |
| 2019/0265490 A1 | 8/2019 | Duckett, III |
| 2020/0107710 A1 | 4/2020 | Duckett, III et al. |
| 2020/0143545 A1 | 5/2020 | Weng et al. |
| 2020/0305721 A1 | 10/2020 | Chen et al. |
| 2020/0315432 A1 | 10/2020 | Tully et al. |
| 2021/0030277 A1 | 2/2021 | Ferguson, Jr. et al. |
| 2021/0282630 A1 | 9/2021 | Kikuchi et al. |
| 2021/0282654 A1 | 9/2021 | Cha et al. |
| 2021/0338060 A1 | 11/2021 | Tully et al. |
| 2022/0287553 A1 | 9/2022 | Tully et al. |
| 2022/0377217 A1 | 11/2022 | Dehghani et al. |
| 2022/0378280 A1 | 12/2022 | Tully et al. |
| 2023/0105882 A1 | 4/2023 | Abe |
| 2024/0353669 A1 | 10/2024 | Dehghani et al. |

FOREIGN PATENT DOCUMENTS

| | | |
|---|---|---|
| CN | 107124547 A | 9/2017 |
| CN | 107510430 A | 12/2017 |
| EP | 1489406 A1 | 12/2004 |
| EP | 2625998 A1 | 8/2013 |
| EP | 2604177 B1 | 4/2016 |
| JP | H10290780 A | 11/1998 |
| JP | 2006187427 A | 7/2006 |
| JP | 2007037783 A | 2/2007 |
| JP | 2007229135 A | 9/2007 |
| JP | 2009022652 A | 2/2009 |
| JP | 2009095554 A | 5/2009 |
| JP | 2010017377 A | 1/2010 |
| JP | 2015231498 A | 12/2015 |
| JP | 2018042676 A | 3/2025 |
| KR | 20170051264 A | 5/2017 |
| KR | 20180066645 A | 6/2018 |
| WO | WO-2010096447 A2 | 8/2010 |
| WO | WO-2010096453 A1 | 8/2010 |
| WO | WO-2012096878 A2 | 7/2012 |
| WO | WO-2014152753 A1 | 9/2014 |
| WO | WO-2016061052 A1 | 4/2016 |
| WO | WO-2016153741 A1 | 9/2016 |
| WO | WO-2017075602 A1 | 5/2017 |
| WO | WO-2018021035 A1 | 2/2018 |
| WO | WO-2019045971 A1 | 3/2019 |
| WO | WO-2020006454 A1 | 1/2020 |
| WO | WO-2020210168 | 10/2020 |
| WO | WO-2021035094 A1 | 2/2021 |
| WO | 2021108450 A1 | 6/2021 |
| WO | WO-2022029308 A1 | 2/2022 |
| WO | WO-2022058499 A1 | 3/2022 |
| WO | WO-2023091515 A1 | 5/2023 |
| WO | WO-2023205456 A1 | 10/2023 |

OTHER PUBLICATIONS

Cha et al. Dual-display laparascopic laser speckle contrast imaging for real-time surgical assistance. Biomedical Optics Express, 9(12) pp. 1-20 (2018). Available at https://hsrc.himmelfarb.gwu.edu/cgi/viewcontent.cgi?article=3662&context=smhs_peds_facpubs.

Dunn, et al. Laser speckle contrast imaging in biomedical optics. Journal of Biomedical Optics 15(1), 011109 (Jan./Feb. 2010).

Holstein-Rathlou et al. Nephron blood flow dynamics measured by laser speckle contrast imaging. Am J Phsiol Renal Physiol 300: F319-F329, 2011.

Kadambi et al. Rethinking machine vision time of flight with GHz heterodyning. IEEE Access. vol. 5, 1-13, Nov. 2017.

Li et al. SH-ToF: Micro Resolution Time-of-Flight Imaging with Superheterodyne Interferometry, IEEE ICCP, 2018: 1-10.

PCT/US2020/047275 International Search Report & Written Opinion dated Feb. 1, 2021.

PCT/US20/26920 Search Report and Written Opinion dated Jun. 26, 2020.

Richards et al. Intraoperative laser speckle contrast imaging with retrospective motion correction for quantitative assessment of cerebral blood flow. Neurophotonics 1(1), 015006 (Jul.-Sep. 2014).

Richards et al. Low-cost laser speckle contrast imaging of blood flow using a webcam. 2013 Optical Society of America.

U.S. Appl. No. 17/150,708 Notice of Allowance dated Apr. 12, 2022.

U.S. Appl. No. 16/882,297 Notice of Allowance dated Nov. 6, 2020.

U.S. Appl. No. 16/882,297 Office Action dated Aug. 7, 2020.

U.S. Appl. No. 17/150,708 Office Action dated Oct. 26, 2021.

EP20788162.4 Extended European Search Report dated Mar. 7, 2023.

PCT/US2022/050147 International Search Report and Written Opinion dated Apr. 6, 2023.

U.S. Appl. No. 17/838,469 Office Action dated Jun. 9, 2023.

Co-pending U.S. Appl. No. 18/365,839, inventors Tully; Stephen et al., filed Aug. 4, 2023.

EP20855369.3 Supplementary European Search Report dated Aug. 10, 2023.

U.S. Appl. No. 17/838,469 Notice of Allowance dated Jul. 20, 2023.

PCT/US2023/019457 International Search Report and Written Opinion dated Aug. 21, 2023.

(56) References Cited

OTHER PUBLICATIONS

Boas, et al. Laser speckle contrast imaging in biomedical optics. J Biomed Opt. Jan.-Feb. 2010;15(1):011109. doi: 10.1117/1.3285504. 12 pages.
U.S. Appl. No. 18/604,327, inventors Tully; Stephen et al., filed Mar. 13, 2024.
U.S. Appl. No. 18/630,502, inventors Tully; Stephen et al., filed Apr. 9, 2024.
EP20855369.3 Extended European Search Report dated Nov. 14, 2023.
EP20892307.8 Extended European Search Report dated Nov. 6, 2023.
PCT/US2020/026920 International Preliminary Report on Patentability dated Sep. 28, 2021.
PCT/US2020/062086 International Search Report and Written Opinion dated Feb. 10, 2021.
U.S. Appl. No. 17/673,324 Notice of Allowance dated Dec. 26, 2023.
U.S. Appl. No. 17/673,324 Office Action dated Sep. 8, 2023.
U.S. Appl. No. 17/752,617 Office Action dated Jul. 13, 2023.
U.S. Appl. No. 17/752,617 Office Action dated Mar. 6, 2023.
U.S. Appl. No. 17/752,617 Office Action dated Oct. 12, 2023.
Supplemental European Search Report, Jul. 22, 2025, EP application No. 23792607.6, 12 pages.

\* cited by examiner

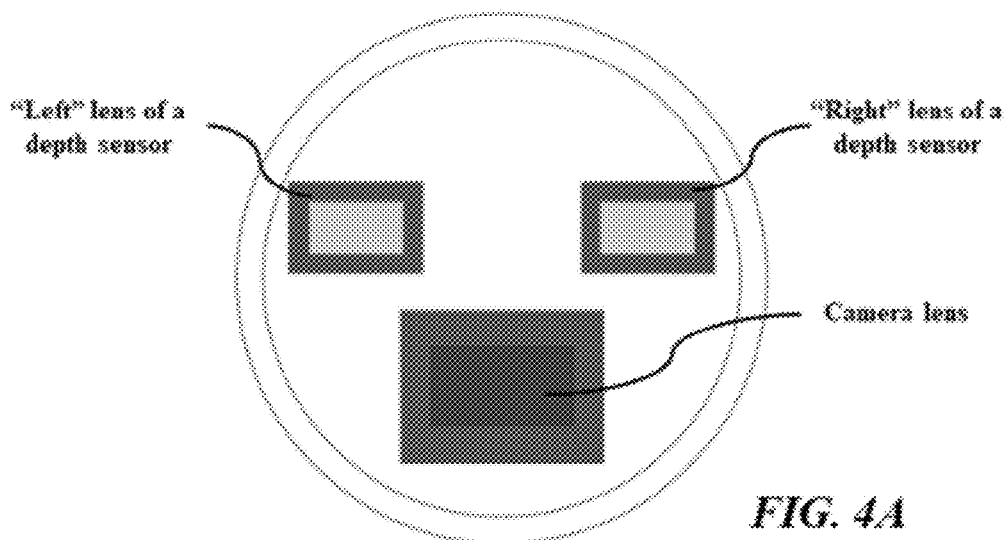
*FIG. 4A*
*FIG. 4B*
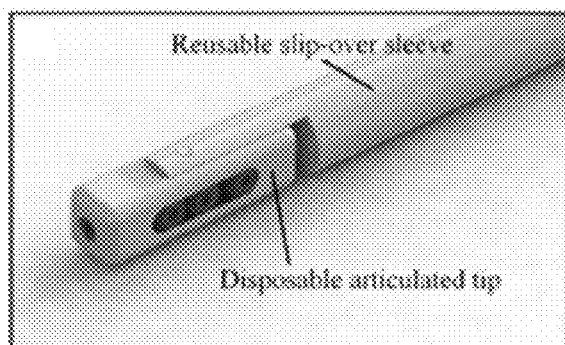
*FIG. 4C*
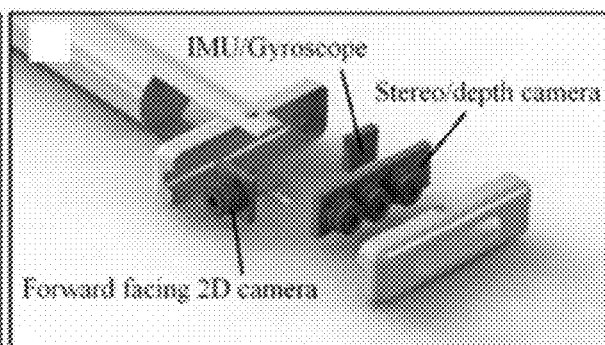
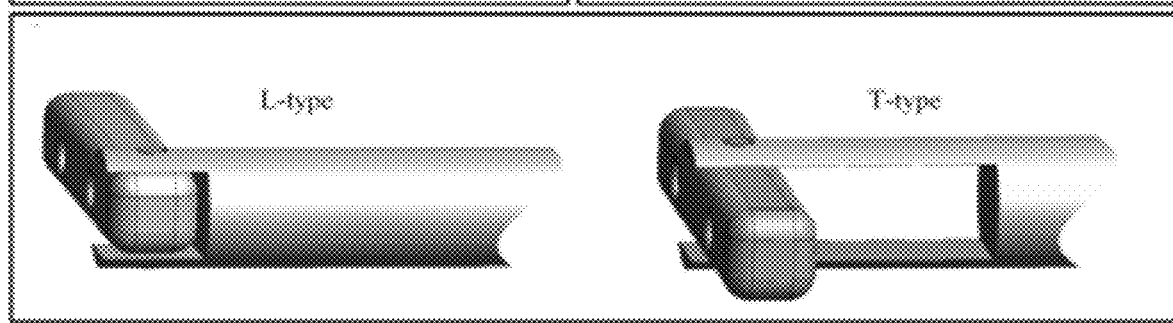
*FIG. 4D*

2810 — Provide a scope assembly comprising (i) a housing unit configured to enclose at least a portion of an elongated scope, and (ii) an imaging unit operably coupled to the housing unit, wherein the imaging unit comprises an optics assembly.

2820 — Receive, by the optics assembly, one or more light beams that are transmitted through the elongated scope, and use the optics assembly to direct at least a portion of the one or more light beams onto two or more locations within a subject's body, wherein at least one of the two or more locations comprises a target site.

2830 — Move the imaging unit via a rotational and/or translational motion relative to the housing unit to alter a field of view when imaging within the subject's body.

*FIG. 8*

2910 — Provide a scope assembly comprising (i) a housing unit configured to enclose at least a portion of an elongated scope, and (ii) an imaging unit operably coupled to the housing unit, wherein the imaging unit comprises an optics assembly.

2920 — Receive, by the optics assembly, one or more light beams that are transmitted through the elongated scope, and use the optics assembly to direct (1) a first portion of the one or more light beams onto a target site within a subject's body and (2) a second portion of the one or more light beams onto another site within the subject's body.

2930 — With aid of at least one depth sensor, receive a first light signal that is reflected from the target site and generate a first set of imaging data comprising depth maps.

2940 — With aid of a two-dimensional (2D) imaging camera, receive a second light signal that is reflected from the another site and generate a second set of imaging data comprising 2D photographic or video images.

*FIG. 9*

SYSTEMS AND METHODS FOR MEDICAL IMAGING

CROSS-REFERENCE

This application is a continuation of U.S. patent application Ser. No. 17/673,324 filed on Feb. 16, 2022, which is a continuation of International Patent Application No. PCT/US2020/047275, filed on Aug. 20, 2020, which claims the benefit of U.S. Provisional Patent Application No. 62/889,863 filed on Aug. 21, 2019, U.S. Provisional Patent Application No. 62/953,724 filed on Dec. 26, 2019, and U.S. Provisional Patent Application No. 62/960,897 filed on Jan. 14, 2020, each of which is entirely incorporated herein by reference for all purposes.

BACKGROUND

Medical imaging technology (e.g., a scope assembly, such as an endoscope) may be used to capture images or video data of internal anatomical features of a subject or patient during medical or surgical procedures. The images or video data captured may be processed and manipulated to provide medical practitioners (e.g., surgeons, medical operators, technicians, etc.) with a visualization of internal structures or processes within a patient or subject.

Images or video data of internal anatomical features by an endoscope may be limited and often fail to provide complex anatomy or critical structures beneath the tissue surface. The images or video data may be limited to two-dimensional (2D) representation of the tissue surface. As a result, incomplete or incorrect analysis of the target site may be dangerous and lead to unintended tissue damage during surgical procedures. In some cases, at least 2% of hysterectomies may result in surgical complications and unintended injuries, which may result in healthcare costs of at least $1 billion annually in the U.S.

SUMMARY

The present application relates generally to endoscopic devices and, more particularly, to an endoscopic device with an articulating sensor head that includes a plurality of sensors. The articulating sensor head may provide a medical operator with the ability to image a target region using a plurality of sensors or cameras while minimizing the size of the opening needed to insert the articulating sensor head into a surgical subject's body. The plurality of sensors may be configured to operate together on a single plane or on multiple different planes to improve visualization of a target area. The plurality of sensors may comprise a camera, an imaging sensor, a depth sensor, a time of flight (TOF) sensor, or any other sensor as described herein. The plurality of sensors may enhance endoscopic visualization capabilities by providing a medical operator with a wider field of view of the target area. The plurality of sensors may also be used to capture one or more high resolution images of the target area. The one or more high resolution images may be generated based on measurements or imaging data obtained using the plurality of sensors. Such high resolution images may provide a greater level of detail compared to other medical images obtainable using commercially available endoscopic imaging systems, and may allow medical operators to visualize and accurately quantify biological features or physiological phenomena within the target area.

An endoscopic device for medical imaging is disclosed herein. The endoscopic device of the present disclosure may comprise an elongated scope having a distal end insertable into a patient's body and an opposite proximal end that may be positioned outside the patient's body. An articulating sensor head may be connected to or may extend from the distal end of the elongated scope. The sensor head may comprise a plurality of sensors (e.g., cameras, imaging sensors, TOF sensors, depth sensors, etc.) disposed on a lateral side of the sensor head. The sensor head may be movable relative to the distal end of the elongated scope between (i) a first position wherein the sensor head is aligned, i.e., in-line, with the distal end such that the device can be more easily inserted or removed from the patient's body and (ii) one or more additional positions wherein the sensor head is angled relative to the distal end such that the one or more sensors are oriented to face and visualize a target region. In some embodiments, the one or more additional positions are part of a set of discrete spatial configurations of the sensor head. In some alternate embodiments, the sensor head can be moved or pivoted continuously (i.e., not in discrete steps) to one or more desired additional positions.

A method for using an endoscopic device is also disclosed herein. The endoscopic device may comprise (i) an elongated scope having a distal end insertable into a patient's body and an opposite proximal end adapted to remain outside the patient's body; and (ii) an articulating sensor head connected to or extending from the distal end of the elongated scope. The sensor head may comprise a plurality of cameras (or other sensors) spaced-apart on a lateral side of the sensor head. The sensor head may be pivotable relative to the distal end of the elongated scope between (i) a first position wherein the sensor head is aligned with the distal end and (ii) one or more additional positions wherein the sensor head is angled relative to the distal end. The method may comprise the steps of: (a) inserting the distal end of the elongated scope and the sensor head into the patient's body while the sensor head is oriented in the first position; (b) articulating the sensor head to a second position so that the sensor head is at an angle relative to the distal end such that the sensors are oriented to face a target in the patient's body; (c) visualizing the target region in the patient's body using the sensors on the sensor head while the sensor head is oriented in the second position; (d) articulating the sensor head back to the first position; and (e) retracting the distal end of the elongated scope and the sensor head from the patient's body while the sensor head is oriented in the first position. In one or more additional embodiments, the insertion angle, the insertion depth, and the angle of the sensor head can be concurrently modulated (e.g., while the sensor head is in the patient's body) to facilitate additional views of the target anatomy.

The present disclosure addresses at least the abovementioned shortcomings of conventional medical imaging systems. In one aspect, the present disclosure provides a scope assembly configured to provide depth perception of a target tissue. In some cases, the scope assembly may allow three-dimensional (3D) reconstruction imaging of one or more target tissues. In some cases, the scope assembly may be compatible with one or more medical imaging technologies (e.g., a scope assembly, such as a laparoscope).

In an aspect, the present disclosure provides a scope assembly, comprising: a housing unit configured to enclose at least a portion of an elongated scope, wherein the housing unit is releasably coupled to the at least the portion of the elongated scope; and an imaging unit operably coupled to a distal end of the housing unit, wherein the imaging unit comprises an optics assembly configured to direct one or more light beams that are transmitted through the elongated scope onto a target site within a subject's body, wherein the imaging unit is movable via a rotational or translational motion relative to the housing unit to alter a field of view.

In some embodiments, the optics assembly is configured to move via a rotational or translational motion relative to an optical path of the one or more light beams.

In some embodiments, the optics assembly is further configured to move relative to an optical path of the one or more light beams as the one or more light beams are transmitted through the elongated scope. In some embodiments, the optics assembly is movable to direct the one or more light beams to a different target site within the subject's body. In some embodiments, the optics assembly is configured to move out of the optical path when the imaging unit is oriented substantially parallel to a length of the elongated scope, thereby allowing the one or more light beams to travel through the imaging unit and towards the subject's body without being interrupted by the optics assembly.

In some embodiments, the optics assembly is configured to move relative to a position, an orientation, or a movement of the imaging unit. In some embodiments, the optics assembly is configured to move independent from a position, an orientation, or a movement of the imaging unit.

In some embodiments, the optics assembly comprises one or more mirrors.

In some embodiments of any scope assembly provided herein, the scope assembly further comprises a processor operatively coupled to the optics assembly, wherein the processor is configured to direct movement of the optics assembly.

In some embodiments of any scope assembly provided herein, the imaging unit comprises a camera or a depth sensor.

In another aspect, the present disclosure provides a scope assembly, comprising: a housing unit configured to enclose at least a portion of an elongated scope, wherein the housing unit is releasably coupled to the at least the portion of the elongated scope; and an imaging unit operably coupled to a distal end of the housing unit, wherein the imaging unit comprises a camera and a depth sensor on different sides of the imaging unit, such that the camera and the depth sensor have different optical axes, wherein the imaging unit is configured to move relative to the housing unit to alter a field of view of the camera or the depth sensor.

In some embodiments, an optical axis of the camera is oriented substantially parallel to a length of the elongated scope when the imaging unit is in a first configuration relative to the housing unit. In some embodiments, an optical axis of the depth sensor is oriented substantially parallel to the length of the elongated scope when the imaging unit is in a second configuration relative to the housing unit. In some embodiments, a distal end of the elongated scope is optically exposed through at least a portion of the imaging unit when the imaging unit is in the second configuration, such that the distal end of the elongated scope is optically in communication with a target site within a subject's body. In some embodiments, the at least the portion of the imaging unit comprises (i) an opening or (ii) an optically transparent or semi-transparent window. In some embodiments, the imaging unit is configured to deploy in the second configuration upon contact by a distal end of the elongated scope. In some embodiments, the imaging unit further comprises a spring mechanism configured to deploy the imaging unit in the second configuration.

In some embodiments of any scope assembly provided herein, the first configuration is a non-articulated configuration of the imaging unit, and the second configuration is one of a plurality of articulated configurations of the imaging unit.

In some embodiments of any scope assembly provided herein, an optical axis of the depth sensor and an optical axis of the camera are non-parallel to each other. In some embodiments, the optical axis of the depth sensor is substantially orthogonal to the optical axis of the camera.

In another aspect, the present disclosure provides a scope assembly, comprising: an elongated scope; and an imaging unit attached to a distal end of the elongated scope, wherein the imaging unit comprises a camera and separately a depth sensor, wherein the imaging unit is movable via a rotational or translational motion relative to the elongated scope to alter a field of view of the camera or the depth sensor.

In some embodiments, the camera comprises a first lens, and the depth sensor comprises two or more lenses that are different from the first lens.

In some embodiments, the camera and the depth sensor are on different sides of the imaging unit, such that the camera and the depth sensor have orthogonal optical axes. In some embodiments, an optical axis of the camera is oriented substantially parallel to a length of the elongated scope when the imaging unit is in a first configuration relative to the elongated scope. In some embodiments, an optical axis of the depth sensor is oriented substantially parallel to the length of the elongated scope when the imaging unit is in a second configuration relative to the elongated scope. In some embodiments, a distal end of the elongated scope is optically exposed through at least a portion of the imaging unit when the imaging unit is in the second configuration, such that the distal end of the elongated scope is optically in communication with a target site within a subject's body.

In some embodiments of any scope assembly provided herein, the first configuration is a non-articulated configuration of the imaging unit, and the second configuration is one of a plurality of articulated configurations of the imaging unit.

In another aspect, the present disclosure provides a scope assembly, comprising: an elongated scope; an imaging unit operably coupled to a distal end of the elongated scope, wherein the imaging unit is configured to (1) move relative to the elongated scope and (2) obtain a plurality of imaging data of a target site from a plurality of perspectives; one or more motion sensors operatively coupled to the imaging unit, wherein the one or more motion sensors are configured to provide spatial information of the imaging unit as the imaging unit moves relative to the elongated scope; and a processor operatively coupled to the imaging unit and the one or more sensor, wherein the processor is configured to generate a three-dimensional (3D) reconstruction of the target site based on the plurality of imaging data and the spatial information.

In some embodiments, the one or more motion sensors comprise an inertial measurement unit (IMU).

In some embodiments, the one or more motion sensors are further configured to provide spatiotemporal information of the imaging unit.

In some embodiments, the imaging unit is configured to move relative to the elongated scope via one or more joint mechanisms, and the one or more motion sensors are operatively coupled to the one or more joint mechanisms. In some embodiments, the imaging unit comprises a plurality of joint mechanisms, and an individual joint mechanism of the plurality of joint mechanisms comprises at least one motion sensor.

In another aspect, the present disclosure provides a scope assembly, comprising: an optical adapter that comprises: (i) a housing comprising a first end configured to releasably couple to an elongated scope, and a second end configured to releasably couple to a camera; (ii) a depth sensor coupled to the housing; and (iii) an optics unit disposed in the housing, wherein the optics unit is configured to (1) receive light signals that are reflected from a target site within a subject's body and transmitted through the elongated scope, and (2) reflect a first portion of the light signals onto one of the depth sensor or the camera, while permitting a second portion of the light signals to pass through to the other of the depth sensor or the camera.

In some embodiments, the image sensor is permanently coupled to the housing or releasably coupled to the housing.

In some embodiments, the optics unit is configured to reflect the first portion of the light signals onto the depth sensor, while permitting the second portion of the light signals to pass through to the camera. In some embodiments, the optics unit comprises a shortpass dichroic mirror.

In some embodiments, the optics unit is configured to reflect the first portion of the light signals onto the camera, while permitting the second portion of the light signals to pass through to the depth sensor. In some embodiments, the optics unit comprises a longpass dichroic mirror.

In some embodiments, one of the first portion or the second portion of the light signals directed to the depth sensor by the optics unit comprises reflected light that is generated when the target site is illuminated with one or more light beams comprising a coherent laser light. In some embodiments, the other of the first portion or the second portion of the light signals directed to the depth sensor by the optics unit comprises reflected light that is generated when the target site is illuminated with one or more light beams comprising a white light.

In some embodiments of any scope assembly provided herein, the imaging unit is configured to releasably couple to the housing unit.

In some embodiments of any scope assembly provided herein, the housing unit or the imaging unit is disposable and configured for single use in a medical imaging procedure. In some embodiments of any scope assembly provided herein, the housing unit or the imaging unit is configured to be reusable for a plurality of medical imaging procedures. In some embodiments of any scope assembly provided herein, the scope assembly is sterilized.

In some embodiments of any scope assembly provided herein, at least a portion of the imaging unit comprises (i) an opening or (ii) an optically transparent or semi-transparent window, thereby allowing at least a portion of the one or more light beams to be directed through the at least the portion of the imaging unit.

In some embodiments of any scope assembly provided herein, the imaging unit comprises an end portion and a side portion. In some embodiments, (i) the camera is mounted on the end portion of the imaging unit and (ii) the depth sensor is mounted on the side portion of the imaging unit. In some embodiments, (i) the camera is mounted on the side portion of the imaging unit and (ii) the depth sensor is mounted on the end portion of the imaging unit. In some embodiments, the side portion and the end portion of the imaging unit are not located on a same plane. In some embodiments, the side portion and the end portion of the imaging unit are not parallel to each other. In some embodiments, the side portion and the end portion of the imaging unit are substantially orthogonal to each other. In some embodiments, the end portion of the imaging unit is aligned with a longitudinal axis of the elongated scope.

In some embodiments of any scope assembly provided herein, the depth sensor is configured to receive a first light signal that is reflected from a target site upon exposure to at least a portion of one or more light beams transmitted through the elongated scope. In some embodiments of any scope assembly provided herein, the depth sensor is a stereoscopic camera. In some embodiments, the stereoscopic camera comprises a first lens adjacent to a second lens, wherein the first and second lenses are separated by a distance, and wherein the distance is indicative of a measurable depth of the stereoscopic camera. In some embodiments, the distance is at most 10 millimeters.

In some embodiments of any scope assembly provided herein, the depth sensor is a time of flight (ToF) sensor. In some embodiments, the ToF sensor uses heterodyne interferometry.

In some embodiments of any scope assembly provided herein, the camera is configured to receive a second light signal that is reflected from a target site upon exposure to at least a portion of one or more light beams transmitted through the elongated scope. In some embodiments of any scope assembly provided herein, the camera is a RGB camera.

In some embodiments of any scope assembly provided herein, the depth sensor is configured to generate a first set of imaging data comprising photographic or video images containing depth information. In some embodiments, the first set of imaging data comprises a depth map of the target site.

In some embodiments of any scope assembly provided herein, the camera is configured to generate a second set of imaging data comprising two-dimensional (2D) photographic or video images.

In some embodiments of any scope assembly provided herein, the imaging unit is configured to move relative to the housing or the elongated scope at an angle ranging from about 0 degrees to about 360 degrees.

In some embodiments of any scope assembly provided herein, the imaging unit is operably coupled to the housing unit or the elongated scope via one or more joint mechanisms that are configured to permit the imaging unit to move in one or more degrees of freedom. In some embodiments of any scope assembly provided herein, the one or more joint mechanisms are configured to permit the imaging unit to move in three or more degrees of freedom. In some embodiments of any scope assembly provided herein, the one or more joint mechanisms are configured to permit the imaging unit to move in six degrees of freedom. In some embodiments of any scope assembly provided herein, the one or more joint mechanisms comprise a pivot joint mechanism selected from the group consisting of pivot joint, hinge joint, saddle joint, condyloid joint, and ball and socket joint. In some embodiments of any scope assembly provided herein, the one or more joint mechanisms are operatively coupled to one or more actuators configured to direct the movement of the imaging unit.

In some embodiments of any scope assembly provided herein, the imaging unit is coupled to the housing unit or the elongated scope via a T-type joint. In some embodiments of any scope assembly provided herein, the imaging unit is coupled to the housing unit or the elongated scope via an L-type joint.

In some embodiments of any scope assembly provided herein, the scope assembly further comprises a processor operatively coupled to the imaging unit, wherein the processor is configured to direct movement of the imaging unit relative to the housing unit or the elongated scope.

In some embodiments of any scope assembly provided herein, the one or more light beams comprise white light or a coherent laser light. In some embodiments of any scope assembly provided herein, the white light is in a visible electromagnetic spectrum. In some embodiments of any scope assembly provided herein, the coherent laser light is in an invisible electromagnetic spectrum. In some embodiments of any scope assembly provided herein, the coherent laser light is provided from a single laser source having substantially a single wavelength. In some embodiments of any scope assembly provided herein, the coherent laser light is provided from a plurality of laser sources having a plurality of different wavelengths. In some embodiments of any scope assembly provided herein, the coherent laser light is for a time of flight (ToF) measurement.

In some embodiments of any scope assembly provided herein, the scope assembly further comprises a processor operatively coupled to the imaging unit, wherein the processor is configured to direct movement of the imaging unit relative to the housing or the elongated scope.

In some embodiments of any scope assembly provided herein, the scope assembly further comprises a processor operatively coupled to the depth sensor, wherein the processor is configured to quantify depth information of one or more target sites within the subject body based on an imaging data from the depth sensor.

In some embodiments of any scope assembly provided herein, the processor is controllable by a user of the scope assembly.

In another aspect, the present disclosure provides an imaging kit, comprising: any scope assembly provided herein; and an illumination source configured to transmit the one or more light beams to and through the elongated scope.

In another aspect, the present disclosure provides a method, comprising: (a) providing a scope assembly comprising (i) a housing unit configured to enclose at least a portion of an elongated scope, wherein the housing unit is releasably coupled to the at least the portion of the elongated scope, and (ii) an imaging unit operably coupled to a distal end of the housing unit, wherein the imaging unit comprises an optics assembly configured to direct one or more light beams that are transmitted through the elongated scope onto a target site within a subject's body; (b) receiving, by the optics assembly, the one or more light beams from the elongated scope; and (c) directing, by the optics assembly, the one or more light beams onto the target site within the subjects body.

In some embodiments, the method further comprises moving the imaging unit via a rotational or translational motion relative to the housing unit to direct the one or more light beams onto the target site within the subject's body.

In some embodiments, the method further comprises moving the optics assembly via a rotational or translational motion relative to an optical path of the one or more light beams.

In some embodiments, the method further comprises moving the optics assembly relative to an optical path of the one or more light beams as the one or more light beams are transmitted through the elongated scope.

In some embodiments, the method further comprises moving the optics assembly to direct the one or more light beams to a different target site within the subject's body.

In some embodiments, the method further comprises moving the optics assembly relative to a position, an orientation, or a movement of the imaging unit.

In some embodiments, the method further comprises moving the optics assembly independent from a position, an orientation, or a movement of the imaging unit.

In another aspect, the present disclosure provides a method, comprising: (a) providing a scope assembly comprising (i) a housing unit configured to enclose at least a portion of an elongated scope, wherein the housing unit is releasably coupled to the at least the portion of the elongated scope, and (ii) an imaging unit operably coupled to a distal end of the housing unit, wherein the imaging unit comprises a camera and a depth sensor on different sides of the imaging unit; (b) with aid of the camera, receiving a first light signal from a first optical axis; and (c) with aid of the depth sensor, receiving a second light signal from a second optical axis that is different from the first optical axis.

In some embodiments, the method further comprises moving the imaging unit via a rotational or translational motion relative to the housing unit to alter a field of view of the camera or the depth sensor.

In some embodiments, the method further comprises subjecting the imaging unit in a first configuration relative to the housing unit, such that the first optical axis of the camera is oriented substantially parallel to a length of the elongated scope. In some embodiments, the method further comprises subjecting the imaging unit in a second configuration relative to the housing unit, such that the second optical axis of the depth sensor is oriented substantially parallel to the length of the elongated scope. In some embodiments, the method further comprises, while the imaging unit is in the second configuration, directing one or more light beams from a distal end of the elongated scope, through (i) an opening or (ii) an optically transparent or semi-transparent window of at least a portion of the imaging unit, and towards a target site within a subject's body. In some embodiments, the method further comprises deploying the imaging unit in the second configuration upon contacting the imaging unit by a distal end of the elongated scope.

In some embodiments, the second optical axis of the depth sensor is substantially orthogonal to the first optical axis of the camera.

In another aspect, the present disclosure provides a method, comprising: (a) providing a scope assembly comprising (i) an elongated scope and (ii) an imaging unit attached to a distal end of the elongated scope, wherein the imaging unit comprises a camera and separately a depth sensor; (b) with aid of the camera, generating a first set of imaging data comprising two-dimensional (2D) photographic or video images; and (c) with aid of the depth sensor, generating a second set of imaging data comprising depth maps.

In some embodiments, the method further comprises moving the imaging unit via a rotational or translational motion relative to the elongated scope to alter a field of view of the camera or the depth sensor.

In some embodiments, the camera comprises a first lens, and the depth sensor comprises two or more lenses that are different from the first lens.

In some embodiments, the camera and the depth sensor are on different sides of the imaging unit, such that the camera and the depth sensor have orthogonal optical axes. In some embodiments, the method further comprises subjecting the imaging unit in a first configuration, such that an optical axis of the camera is oriented substantially parallel to a length of the elongated scope. In some embodiments, the method further comprises subjecting the imaging unit in a second configuration, such that an optical axis of the depth sensor is oriented substantially parallel to the length of the elongated scope. In some embodiments, the method further comprises, while the imaging unit is in the second configuration, directing one or more light beams from a distal end of the elongated scope, through (i) an opening or (ii) an optically transparent or semi-transparent window of at least a portion of the imaging unit, and towards a target site within a subject's body.

In another aspect, the present disclosure provides a method, comprising: (a) providing a scope assembly comprising (i) an elongated scope, (ii) an imaging unit operatively coupled to a distal end of the elongated scope, and (iii) one or more motion sensors operatively coupled to the imaging unit; (b) moving the imaging unit relative to the elongated scope to obtain a plurality of imaging data of a target site from a plurality of perspectives; (c) with aid of the one or more motion sensors, providing spatial information of the imaging unit as the imaging unit moves relative to the elongated scope; and (d) with aid of a processor, generating a three-dimensional (3D) reconstruction of the target site based on the plurality of imaging data and the spatial information.

In some embodiments, the one or more motion sensors comprise an inertial measurement unit (IMU).

In some embodiments, the method further comprises, in (c), providing spatiotemporal information of the imaging unit.

In some embodiments, the method further comprises, in (b), moving the imaging unit relative to the elongated scope via one or more joint mechanisms. In some embodiments, the imaging unit comprises a plurality of joint mechanisms, and an individual joint mechanism of the plurality of joint mechanisms comprises at least one motion sensor.

In another aspect, the present disclosure provides a method, comprising: (a) providing a scope assembly comprising an optical adapter, wherein the optical adapter comprises (i) a housing comprising a first end configured to releasably couple to an elongated scope, and a second end configured to releasably couple to a camera, (ii) a depth sensor coupled to the housing, and (iii) an optics unit disposed in the housing; and (b) with aid of the optics unit, (1) receiving light signals that are reflected from a target site within a subject's body and transmitted through the elongated scope, and (2) reflecting a first portion of the light signals onto one of the depth sensor or the camera, while permitting a second portion of the light signals to pass through to the other of the depth sensor or the camera.

In some embodiments, the image sensor is permanently coupled to the housing or releasably coupled to the housing.

In some embodiments, in step (b), the first portion of the light signals is reflected onto the depth sensor, while the second portion of the light signals is permitted to pass through to the camera.

In some embodiments, in step (b), the first portion of the light signals is reflected onto the camera, while the second portion of the light signals is permitted to pass through to the depth sensor.

In some embodiments, one of the first portion or the second portion of the light signals directed to the depth sensor by the optics unit comprises reflected light that is generated when the target site is illuminated with one or more light beams comprising a coherent laser light. In some embodiments, the other of the first portion or the second portion of the light signals directed to the depth sensor by the optics unit comprises reflected light that is generated when the target site is illuminated with one or more light beams comprising a white light.

In another aspect, the present disclosure provides a system for medical imaging, comprising (a) a plurality of light sources comprising (i) a time of flight (TOF) light source configured to generate a TOF light and optionally (ii) at least one of a white light source, a laser speckle light source, and a fluorescence excitation light source; (b) a scope configured to direct a plurality of light beams or light pulses generated by the plurality of light sources to a target region, wherein the plurality of light beams or light pulses comprise the TOF light generated using the TOF light source; (c) a TOF sensor configured to receive at least a portion of the plurality of light beams or light pulses that is reflected from the target region, wherein said portion comprises one or more TOF light beams or TOF light pulses reflected from the target region; and (d) an image processing unit configured to generate a depth map of the target region based at least in part on one or more TOF measurements obtained using the TOF sensor.

In some embodiments, the TOF light source comprises one or more lasers or light emitting diodes (LEDs). In some embodiments, the TOF light comprises an infrared or near infrared light having a wavelength from about 700 nanometers (nm) to about 1 millimeter (mm). In some embodiments, the TOF light comprises visible light having a wavelength from about 400 nm to about 700 nm. In some embodiments, the visible light comprises blue light having a wavelength from about 400 nm to about 500 nm. In some embodiments, the TOF light comprises a plurality of light beams or light pulses having a plurality of wavelengths from about 400 nm to about 1 mm.

In some embodiments, the TOF light source is located remote from the scope and operatively coupled to the scope via a light guide. In some embodiments, the TOF light source is located on the scope and configured to provide the TOF light to the scope via a scope-integrated light guide. In some embodiments, the TOF light source is configured to illuminate the target region through a rod lens. In some embodiments, the TOF light source is located at a tip of the scope. In some embodiments, the TOF light source is attached to a portion of a surgical subject's body, wherein the portion of the surgical subject's body is proximal to the target region being imaged. In some embodiments, the TOF light source is configured to provide the TOF light to the target region via one or more secondary illuminating scopes.

In some embodiments, the system may further comprise an optical element configured to separate the plurality of light beams or light pulses reflected from the target region into (i) a first set of light signals corresponding to the TOF light and (ii) a second set of light signals corresponding to white light, laser speckle light, or fluorescence excitation light. In some embodiments, the optical element comprises a beam splitter. In some embodiments, the optical element comprises a dichroic mirror. In some embodiments, the optical element is configured to direct the first set of light signals to the TOF sensor and the second set of light signals to one or more imaging devices. In some embodiments, the one or more imaging devices comprise a camera or a sensor configured for RGB imaging, laser speckle imaging, or fluorescence imaging.

In some embodiments, the TOF sensor is positioned along a common beam path of the plurality of light beams or light pulses reflected from the target region, wherein the common beam path is disposed between the target region and the optical element. In some embodiments, the TOF sensor is positioned along a discrete beam path of the first set of light signals. In some embodiments, the TOF sensor is positioned at a tip of the scope. In some embodiments, the TOF sensor is attached to a portion of a surgical subject's body, wherein the portion of the surgical subject's body is proximal to the target region being imaged.

In some embodiments, the system may further comprise a plurality of depth sensing devices configured to obtain the one or more TOF measurements used to generate the depth map of the target region. In some embodiments, the plurality of depth sensing devices are selected from the group consisting of a stereo imaging device, a structured light imaging device, and a TOF sensor. In some embodiments, the TOF sensor comprises an imaging sensor configured to implement heterodyning to enable depth sensing and to enhance TOF resolution.

In some embodiments, the TOF light source is configured to generate a plurality of TOF light pulses. In some embodiments, the TOF light source is configured to generate a continuous TOF light beam. In some embodiments, the continuous TOF light beam undergoes amplitude modulation to enable TOF measurements based on a phase difference between an emitted TOF light and a reflected TOF light.

In some embodiments, the system may further comprise an electromechanical shutter or gate configured to generate a plurality of TOF light pulses by chopping the continuous light beam into the plurality of TOF light pulses.

In some embodiments, the system may further comprise a TOF light modulator. In some embodiments, the TOF light modulator comprises a diverging lens that is positioned along a light path of the TOF light and configured to modulate an illumination intensity of the TOF light across the target region. In some embodiments, the TOF light modulator comprises a light diffusing element that is positioned along a light path of the TOF light and configured to modulate an illumination intensity of the TOF light across the target region. In some embodiments, the TOF light modulator comprises a beam steering element configured to illuminate the target region and one or regions proximal to the target region.

In some embodiments, the system may further comprise a TOF parameter optimizer configured to adjust one or more pulse parameters and one or more camera parameters, based at least in part on a desired application, depth range, tissue type, scope type, or procedure type, to improve a tolerance or an accuracy of TOF depth sensing.

In some embodiments, the one or more TOF measurements obtained using the TOF sensor are based at least in part on the one or more pulse parameters and the one or more camera parameters. In some embodiments, the one or more pulse parameters are selected from the group consisting of an illumination intensity, a pulse width, a pulse shape, a pulse count, a pulse on/off level, a pulse duty cycle, a TOF light pulse wavelength, a light pulse rise time, and a light pulse fall time. In some embodiments, the one or more camera parameters are selected from the group consisting of a number of shutters, shutter timing, shutter overlap, shutter spacing, and shutter duration.

In some embodiments, the TOF parameter optimizer is configured to adjust the one or more pulse parameters and the one or more camera parameters in real time. In some embodiments, the TOF parameter optimizer is configured to adjust the one or more pulse parameters and the one or more camera parameters offline. In some embodiments, the TOF parameter optimizer is configured to adjust the one or more pulse parameters and the one or more camera parameters based on a feedback loop. In some embodiments, the feedback loop comprises a real-time control loop that is configured to adjust the one or more pulse parameters or the one or more camera parameters based on a temperature of the TOF light source or the TOF sensor.

In some embodiments, the system may further comprise an image post processing unit configured to update the depth map based on an updated set of TOF measurements obtained using the one or more adjusted pulse parameters or camera parameters. In some embodiments, the system may further comprise an image post processing unit configured to update the depth map based on temperature fluctuations associated with an operation of the TOF light source or the TOF sensor, thereby enhancing depth sensing accuracy and surgical safety.

In some embodiments, the system may further comprise an image post processing unit configured to perform image post processing on the depth map to enhance depth sensing accuracy and surgical safety, wherein the image post processing comprises at least one of spatial filtering and temporal filtering based on a measured depth of a feature or a pixel within the depth map. In some embodiments, the image post processing comprises adjusting a size of a filtering kernel. In some embodiments, the size of the filtering kernel is adjustable based on a measured depth of one or more features in the target region in order to maintain a desired imaging resolution at said measured depth.

In some embodiments, the system may further comprise a calibration unit configured to perform at least one of (i) camera calibration to correct camera reprojection errors and distortions in an XY plane and (ii) depth calibration to correct for depth measurement distortions along a Z axis. In some embodiments, the calibration unit is configured to perform the camera calibration or the depth calibration using a calibration target.

In some embodiments, the calibration target is a target located on a static rig. In some embodiments, the calibration target is a target located on a movable rig.

In some embodiments, the calibration unit is configured to perform the camera calibration or the depth calibration using a video of the calibration target. In some embodiments, the calibration unit is configured to perform the camera calibration or the depth calibration using camera reconstruction quality as feedback. In some embodiments, the calibration unit is configured to perform the camera calibration or the depth calibration based at least in part on TOF light angle entry correction. In some embodiments, the calibration unit is configured to perform the camera calibration or the depth calibration based on IR intensity error calibration or RGB intensity error correction. In some embodiments, the calibration unit is configured to perform real time camera calibration and real time depth calibration based at least in part on prior depth sensing measurements or a desired application, depth range, tissue type, scope type, or procedure type.

In some embodiments, the TOF sensor comprises an imaging sensor configured for TOF imaging and at least one of RGB imaging, laser speckle imaging, and fluorescence imaging. In some embodiments, the imaging sensor is configured for TOF imaging and perfusion imaging. In some embodiments, the imaging sensor is configured to capture TOF depth signals and laser speckle signals during alternating or different temporal slots. In some embodiments, the imaging sensor is configured to simultaneously capture TOF depth signals and laser speckle signals to generate one or more medical images comprising a plurality of spatial regions corresponding to different imaging modalities.

In some embodiments, the system may further comprise an image post processing unit configured to normalize an RGB image of the target region, a fluorescent image of the target region, or speckle based flow and perfusion signals associated with the target region, based at least in part on one or more TOF measurements obtained using the TOF sensor. In some embodiments, the image post processing unit is configured to use an illumination profile of the target region and a distance between the scope and the target region being imaged to correct for image intensity at a periphery of one or more RGB or fluorescent images obtained using the scope. In some embodiments, the image post processing unit is configured to use a constant hematocrit concentration to estimate blood flow velocity through or proximal to the target region.

In some embodiments, the system may further comprise a processor configured to determine a translational and a rotational motion of the scope, based at least in part on (i) a known position or a known depth of the target region and (ii) a known velocity of the scope or scope assembly. In some embodiments, the processor is further configured to use the translational and rotational motion of the scope to reduce speckle motion artifacts, perform three-dimensional (3D) reconstruction of the target region, generate a minimap associated with the target region, or autonomously control a position or an orientation of a robotic camera. In some embodiments, the processor is further configured to use the translational and rotational motion of the scope to simulate binocular vision, perform image scaling, determine a proximity of objects or features to the scope, or perform grid overlays on one or more images obtained using the scope. In some embodiments, the processor is further configured to refine a computation of the translational and rotational motion of the scope based at least in part on one or more kinematic measurements obtained using a motion sensor or an inertial measurement unit.

In some embodiments, the system may further comprise a processor configured to control a motion of a robotic camera based at least in part on the one or more TOF measurements obtained using the TOF sensor.

In some embodiments, the system may further comprise a stereo imaging device configured to obtain a set of depth measurements of the target region. In some embodiments, the image processing unit is configured to generate the depth map based at least in part on the set of depth measurements obtained using the stereo imaging device and the one or more TOF measurements obtained using the TOF sensor. In some embodiments, the image processing unit is configured to use the one or more TOF measurements obtained using the TOF depth sensor to train a stereo imaging algorithm or a monocular depth algorithm, wherein said stereo imaging algorithm or said monocular depth algorithm is configured to process the set of depth measurements obtained using the stereo imaging device. In some embodiments, the image processing unit is further configured to generate one or more RGB images, laser speckle images, or fluorescence images of the target region, based at least in part on the plurality of light beams or light pulses reflected from the target region.

In another aspect, the present disclosure provides an endoscopic device, comprising: an elongated scope having a distal end insertable into a patient's body and an opposite proximal end adapted to remain outside the patient's body; and an articulating sensor head connected to or extending from the distal end of the elongated scope, said articulating sensor head comprising one or more sensors disposed on a lateral side of the articulating sensor head, wherein said articulating sensor head is movable relative to the distal end of the elongated scope between a first position wherein the articulating sensor head is aligned with the distal end and one or more additional positions wherein the articulating sensor head is angled relative to the distal end such that the one or more sensors are oriented to face and visualize a target in the patient's body.

In some embodiments, the one or more sensors comprise a camera, an imaging sensor, a TOF depth sensor, a stereoscopic imaging device, or a structured light scanner.

In some embodiments, a portion of the articulating sensor head is connected to or extends from the distal end of the articulating sensor head such that the endoscopic device has an L-shaped configuration when the articulating sensor head is pivoted about 90° relative to the distal end.

In some embodiments, a mid-portion of the articulating sensor head is connected to the distal end of the articulating sensor head such that the endoscopic device has a T-shaped configuration when the articulating sensor head is pivoted about 90° relative to the distal end.

In some embodiments, the articulating sensor head includes one or more light sources for illuminating the target. In some embodiments, the articulating sensor head further comprises a navigation camera disposed on or near a distal tip of the articulating sensor head. In some embodiments, the articulating sensor head comprises one or more cameras disposed on different sides of the articulating sensor head.

In some embodiments, the device may further comprise a mechanism for pivoting the articulating sensor head from the first position to the one or more additional positions. In some embodiments, the one or more additional positions correspond to a set of discrete spatial configurations of the articulating sensor head. In some embodiments, the articulating sensor head is continuously movable to any of the one or more additional positions.

In another aspect, the present disclosure provides a method of using an endoscopic device, the endoscopic device comprising (i) an elongated scope having a distal end insertable into a patient's body and an opposite proximal end adapted to remain outside the patient's body; and (ii) an articulating sensor head connected to or extending from the distal end of the elongated scope, said articulating sensor head including one or more sensors disposed on a lateral side of the articulating sensor head, wherein said articulating sensor head is movable relative to the distal end of the elongated scope between a first position wherein the articulating sensor head is aligned with the distal end and one or more additional positions wherein the articulating sensor head is angled relative to the distal end, the method comprising the steps of: (a) inserting the distal end of the elongated scope and the articulating sensor head into the patient's body while the articulating sensor head is oriented in the first position; (b) moving the articulating sensor head to a second position wherein said articulating sensor head is at an angle relative to the distal end such that the one or more sensors are oriented to face a target in the patient's body; (c) visualizing the target in the patient's body using the one or more sensors on the articulating sensor head while the articulating sensor head is oriented in the second position; (d) moving the articulating sensor head back to the first position; and (e) retracting the distal end of the elongated scope and the articulating sensor head from the patient's body while the articulating sensor head is oriented in the first position.

In some embodiments, the one or more sensors comprise a camera, an imaging sensor, a TOF depth sensor, a stereoscopic imaging device, or a structured light scanner.

In some embodiments, the method may further comprise, after step (c), rotating the distal end of the elongated scope to capture a plurality of images and panoramically stitch together said plurality of images to generate an extended view of a target region inside the patient's body.

In some embodiments, the plurality of images captured using the one or more sensors are used to generate a three-dimensional (3-D) point cloud.

In some embodiments, the articulating sensor head is in the first position when the distal end of the elongated scope is rotated. In some embodiments, the articulating sensor head is in the second position when the distal end of the elongated scope is rotated Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 4A-4F schematically illustrate example configurations of a scope assembly operatively coupled to an elongated scope, in accordance with some embodiments.

FIG. 8 illustrates an example flowchart of a method for medical imaging, in accordance with some embodiments.

FIG. 9 illustrates an example flowchart of another method for medical imaging, in accordance with some embodiments.

DETAILED DESCRIPTION

Figure 1A:
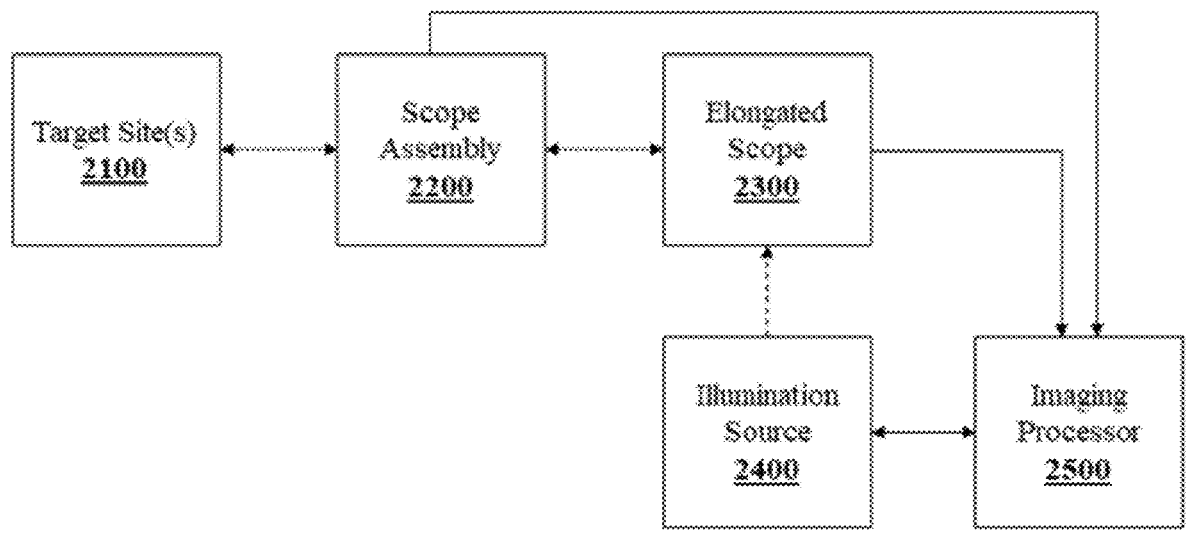
FIGS. 1A-1D schematically illustrate examples of a system for medical imaging, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "perfusion," as used herein, generally refers to passage of fluid through the circulatory system or lymphatic system to an organ or a tissue. In an example, perfusion may refer to the delivery of blood at the level of the arteries or capillaries, in which exchange of oxygen and/or nutrients between blood and tissue takes place. In some cases, perfusion may comprise flow rate of the fluid, volume of the fluid that is present or traversing across a target tissue site, a pattern of flow channels of the fluid at the target tissue site, or a combination thereof. In some cases, perfusion of the liquid of interest may be increasing, decreasing, or remaining substantially the same during one or more imaging processes. In some cases, any change in flow rate or volume of the perfusing fluid may be indicative of (i) one or more biological events or (ii) one or more surgical events occurring upstream of, downstream of, or substantially at the target tissue site. When quantified, perfusion may be measured as the rate at which blood is delivered to tissue, or volume of blood per unit time (blood flow) per unit tissue mass, in units of cubic meter per second per kilogram ($m^3/s/kg$) or milliliters per minute per grams (mL/min/g). Degree of perfusion may be indicative of one or more health conditions, e.g., cardiovascular disease such as coronary artery disease, cerebrovascular disease, peripheral artery disease, etc.

The term "real time" or "real-time," as used interchangeably herein, generally refers to an event (e.g., an operation, a process, a method, a technique, a computation, a calculation, an analysis, a visualization, an optimization, etc.) that is performed using recently obtained (e.g., collected or received) data. In some cases, a real time event may be performed almost immediately or within a short enough time span, such as within at least 0.0001 millisecond (ms), 0.0005 ms, 0.001 ms, 0.005 ms, 0.01 ms, 0.05 ms, 0.1 ms, 0.5 ms, 1 ms, 5 ms, 0.01 seconds, 0.05 seconds, 0.1 seconds, 0.5 seconds, 1 second, or more. In some cases, a real time event may be performed almost immediately or within a short enough time span, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

The terms "time of flight," "time-of-flight," "ToF," or "TOF," as used interchangeably herein, generally refers to one or more measurements of the time taken by a traveling moiety (e.g., an object, particle, or wave) to travel a distance through a medium (e.g., fluid, such as a liquid or gas). Examples of the wave may include acoustic wave and electromagnetic radiation. The time measurement(s) may be used to establish a velocity or path length of the travel moiety, as well as the medium's properties (e.g., density, composition, flow rate, etc.). In some cases, time of flight may refer to the time required for emitted electromagnetic radiation to travel from a source of the electronic radiation to a sensor (e.g., a camera). A time of flight may be the time required for the emitted electromagnetic radiation to reach a target tissue. Alternatively, a time of flight may be the time required for the emitted electromagnetic radiation to reach a target tissue and directed (e.g., reflected) to a sensor. Such sensor may be adjacent to the source of the emitted electromagnetic radiation, or may be at a different location than the source. In some cases, a camera may determine a time of flight based on the phase shift of emitted and received signal (e.g., electromagnetic radiation). Examples of time of flight cameras may include, but are not limited to, radio frequency (RF)-modulated light sources with phase detectors (e.g., Photonic Mixer Devices (PMD), Swiss Ranger™ CanestaVision™), range gated imagers (e.g., ZCam™), and direct time-of-flight images (e.g., light detection and ranging (LIDAR)).

Articulating Sensor Head

Various embodiments disclosed herein relate to endoscopic devices having an articulating sensor head for providing improved visualization of target areas in or on a patient's body.

Currently available endoscopes are effective for gross identification and navigation. However, they lack the ability to perform complex visualization, which requires larger cameras or sensors. Increasing the cross-sectional area of the endoscope's distal tip to include additional cameras would require an undesirably large opening leading into the patient's body cavity (e.g., in the abdominal wall of the patient) to accommodate the increased size of the distal tip.

The endoscopic devices of the present disclosure may comprise multiple cameras or other sensors mounted on the lateral sides of an articulating distal head of an endoscope. The lateral sides of the articulating distal head may provide a larger area to mount additional cameras or sensors on the scope, which greatly increases visualization capabilities while minimizing the need for a large opening into the body cavity. The distal end of the endoscopic device may be inserted through an opening in a surgical subject's body while in a straight orientation. Once in the body cavity, the sensor head may be articulated to a position that allows the multiple cameras or sensors on the lateral sides of the sensor head to face and visualize the target. In addition, the endoscope shaft can be rotated so that the cameras or sensors in the sensor head can capture a series of images of a target region from a plurality of different positions and/or orientations. In one or more embodiments, the series of images can be panoramically stitched together to create a picture that is larger than any one of the individual camera images. In one or more embodiments, the series of images can be used to compute a three dimensional (3-D) point cloud of the scene instantaneously or in real time as the images are being obtained. In one or more embodiments, the series of images can be used to synthesize a 3-D point cloud of the target anatomy, including parts that are not instantaneously in view.

It should be understood that while the application mentions use of cameras in endoscopic devices in various embodiments, such endoscopic devices can alternatively include other types of imaging and non-imaging sensors such as, for example, time of flight sensors and structured light sensors.

Figures 15A, 15B:
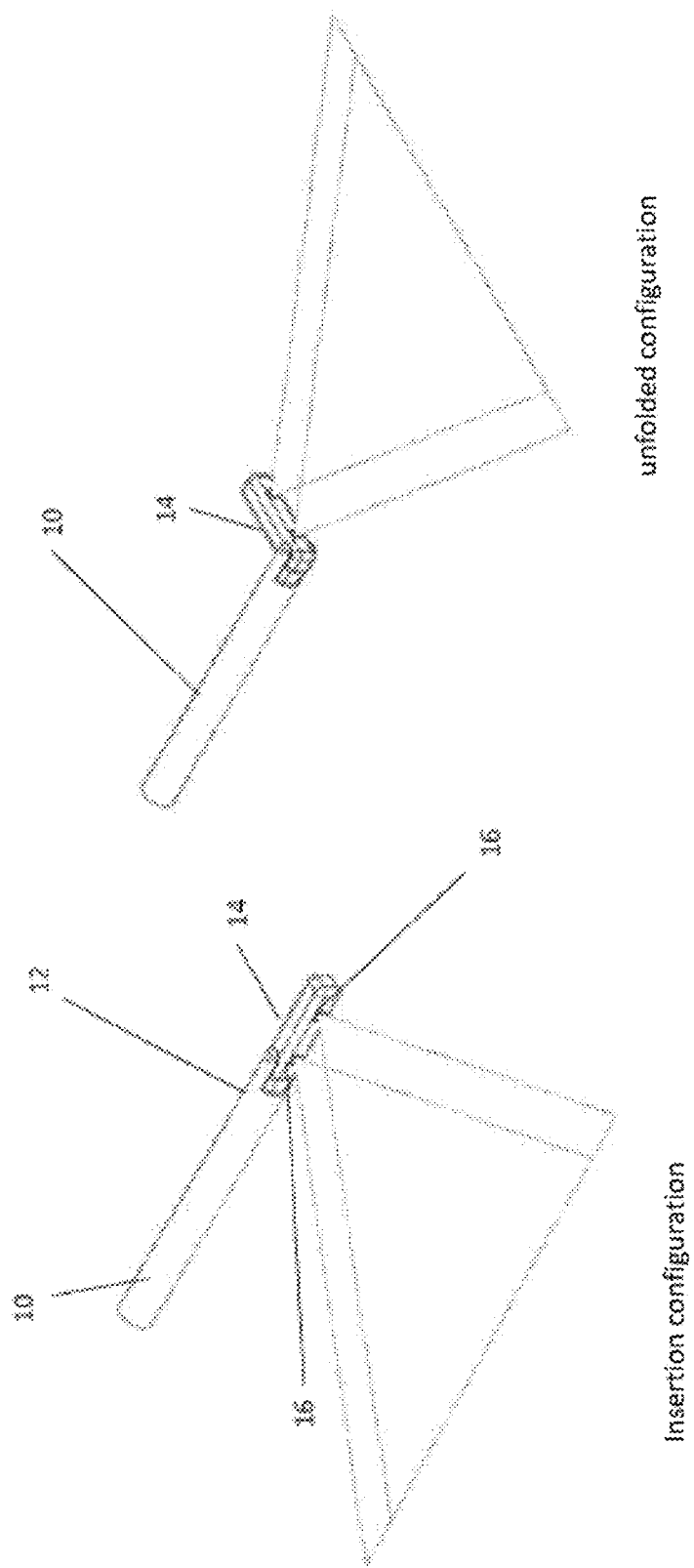
FIG. 15A and FIG. 15B schematically illustrate an exemplary L-shaped articulating sensor head of an endoscopic device in straight and articulated positions, respectively, in accordance with some embodiments.

FIGS. 15A and 15B illustrate an exemplary endoscopic device in accordance with one or more embodiments. The device includes an elongated scope 10 having a distal end 12 that is insertable into a patient's body. The opposite proximal end (not shown) remains outside the patient's body. The device also includes an articulating sensor head 14 having a first end pivotally connected to the distal end 12 and an opposite second free end. The sensor head 14 includes one or more cameras or sensors 16 spaced apart on a lateral side of the sensor head 14 between the first and second ends of the sensor head 14. In the exemplary embodiments illustrated in FIGS. 15A and 15B, there are two cameras or sensors 16 on the sensor head 14. However, any number of cameras or sensors may be used depending on the particular application involved.

The sensor head 14 may be pivotable relative to the distal end 12 of the elongated scope 10 between (i) a first straight orientation position (shown in FIG. 15A) wherein the sensor head 14 is aligned with the distal end 12 and (ii) one or more additional positions wherein the sensor head 14 is angled relative to the distal end 12 such that the cameras or sensors 16 are oriented to face and visualize a target to be imaged. While the FIG. 15B example shows the sensor head angled 90° relative to the distal end 12, it can be pivoted at any desired angle ranging from −90° to 90°.

The multiple cameras or sensors 16 on the sensor head 14 may be located on the same plane within the patient's body. The cameras or sensors 16 may be configured to operate in conjunction with one another such that a detailed representation of the target space can be stitched together from the different camera fields of view. The cameras or sensors 16 can be properly calibrated with each other to enable, e.g., stereoscopic depth computation, since their positions relative to one another are known and fixed to the same rigid plane relative to the sensor head 14. In one or more alternate embodiments, the cameras or sensors may be offset with respect to one another so that they are positioned and/or oriented on different planes.

Figure 16B:
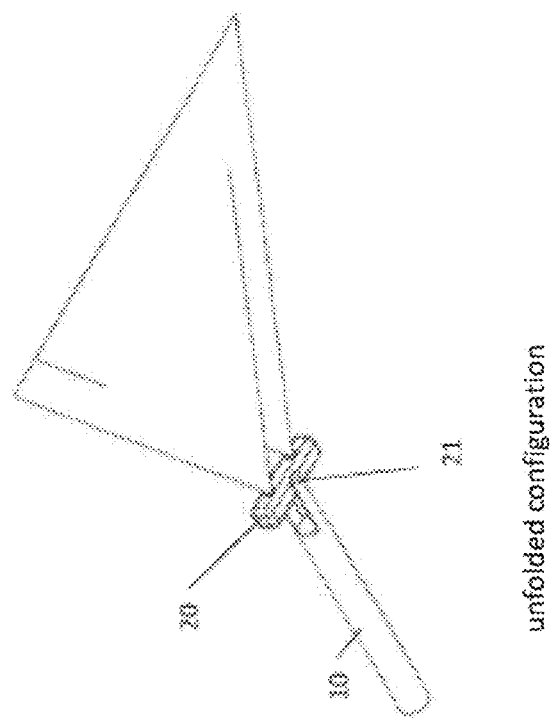
FIG. 16A and FIG. 16B schematically illustrate an exemplary T-shaped articulating sensor head in straight and articulated positions, respectively, in accordance with some embodiments.
Figure 16A:
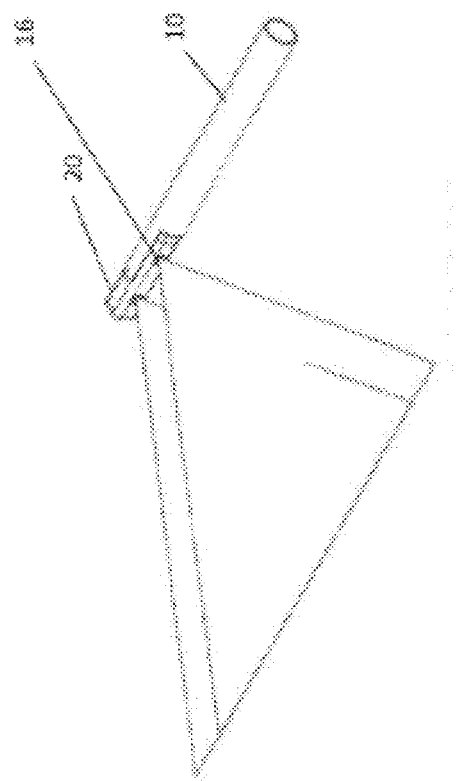

FIGS. 16A and 16B show an exemplary T-shaped articulating sensor head 20 in accordance with one or more embodiments. The sensor head 20 pivots about a central point 21 of the sensor head 20 relative to the endoscopic shaft 10 unlike the L-shaped articulating sensor head of FIGS. 15A and 15B, which pivots about one end of the sensor head.

Figure 19A:
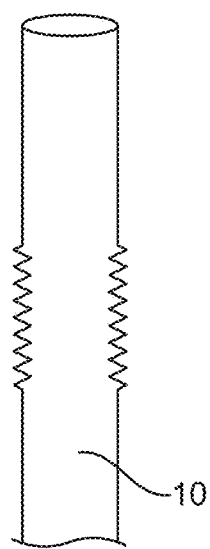
FIG. 19A and FIG. 19B schematically illustrate an exemplary L-shaped articulating sensor head with a flexible bending connection in straight and articulated positions, respectively, in accordance with some embodiments.
Figure 19B:
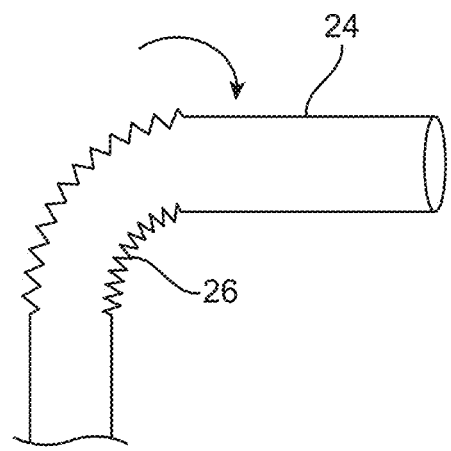

FIGS. 19A and 19B show an exemplary L-shaped articulating sensor head 24 flexibly connected to the distal portion of the endoscopic shaft 10 with a flexible connection 26 in accordance with one or more embodiments. The flexible connection may comprise a joint.

Figure 17B:
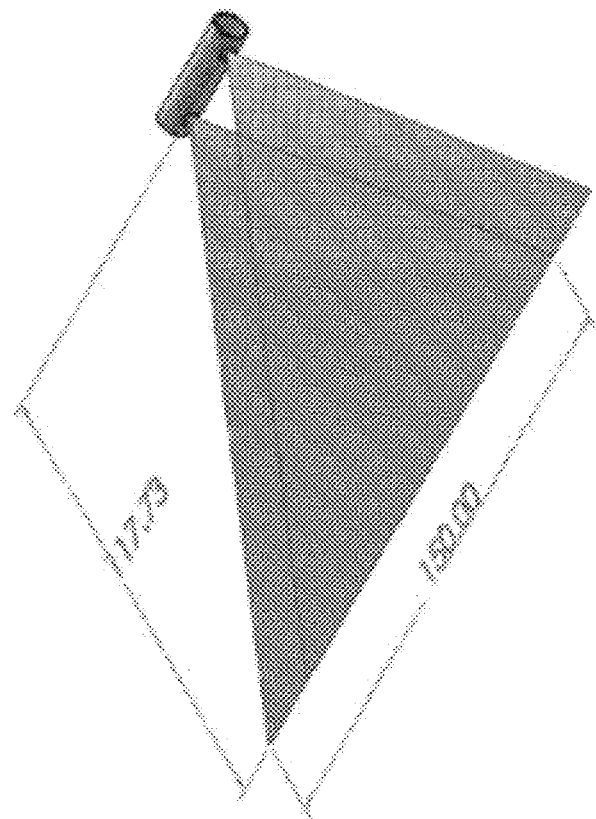
FIG. 17A and FIG. 17B schematically illustrate an increased field of view obtained by an endoscopic device having multiple cameras, in accordance with some embodiments.
Figure 17A:
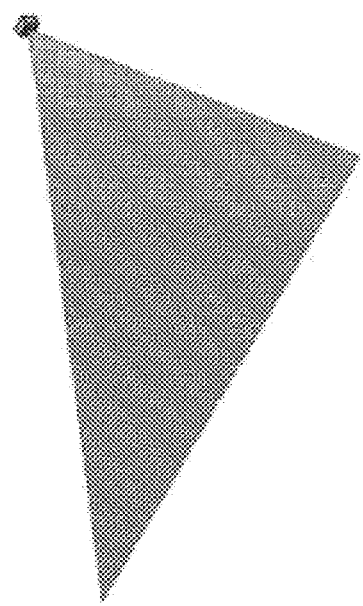

FIGS. 17A and 17B illustrate the increased field of view obtainable using an endoscopic device having multiple cameras or sensors located on the articulating sensor head, compared to an endoscopic device with just a single camera or sensor.

Figure 20:
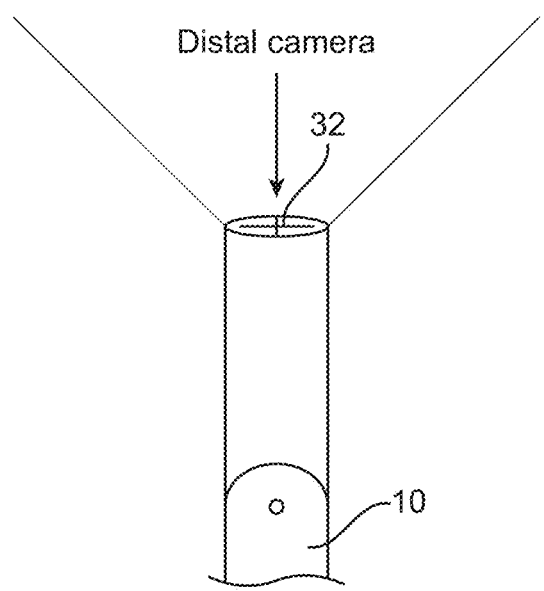
FIG. 20 schematically illustrates an exemplary articulating sensor head with an additional navigation camera at a distal tip of the sensor head, in accordance with some embodiments.

FIG. 20 shows an exemplary articulating sensor head with an additional navigation or guidance camera 32 at the distal tip of a sensor head in accordance with one or more embodiments. The additional navigation or guidance camera 32 at the distal tip of the sensor head may be oriented in a first direction that is different than a second direction in which one or more cameras or sensors located on the lateral sides of the sensor head are oriented.

Figure 21:
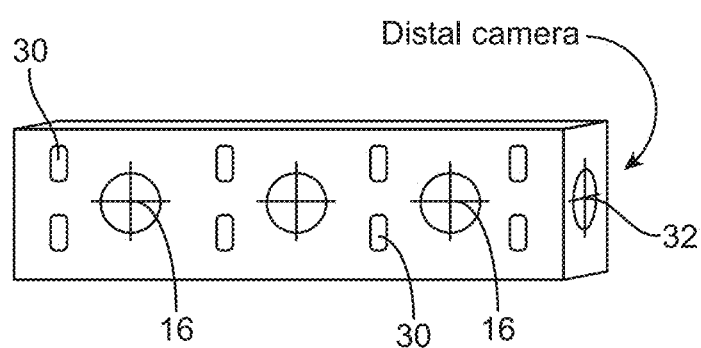
FIG. 21 schematically illustrates an exemplary articulating sensor head with multiple cameras, LED light sources to provide illumination, and an additional navigation camera at the distal tip of the sensor head, in accordance with some embodiments.
Figures 22A, 22B:
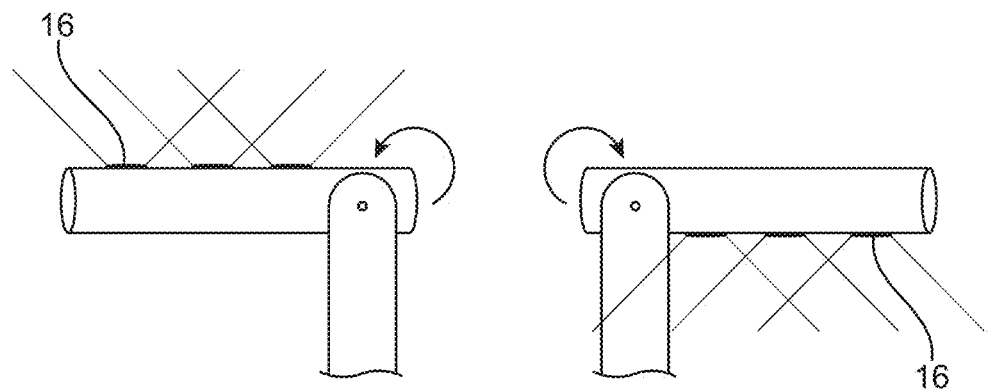
FIG. 22A-22D schematically illustrate an exemplary articulating sensor head with multiple cameras, in accordance with some embodiments.
Figures 22C, 22D:
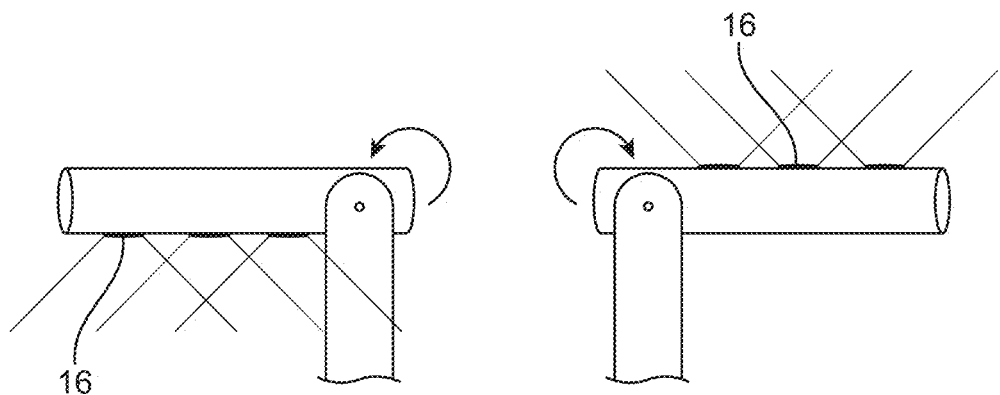

FIG. 21 shows an exemplary articulating sensor head with multiple cameras or sensors 16 and LED light sources 30 to provide illumination, and an additional navigation camera 32 at the distal tip of a sensor head, in accordance with one or more embodiments.

Figure 18A:
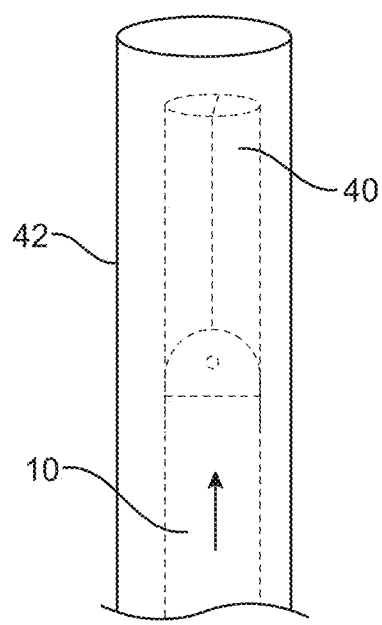
FIG. 18A and FIG. 18B schematically illustrate an exemplary T-shaped articulating sensor head with a mechanical blooming mechanism in straight and articulated positions, respectively, in accordance with some embodiments.
Figure 18B:
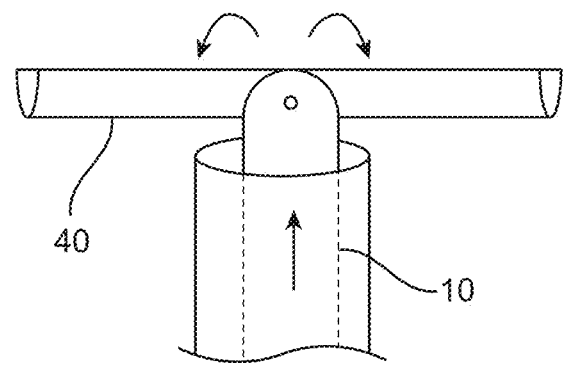

The sensor heads of the endoscopic devices can be pivoted using a variety of mechanisms. In one example, a cable pulley system in the endoscopic device drives an angulation wire to pivot the sensor head. In another example, FIGS. 18A and 18B illustrate a T-shaped articulating sensor head 40 with a mechanical blooming mechanism. The sensor head 40 can be spring loaded to articulate when linearly driven out of a constrictive sheath 42. Alternatively, the sensor head can be linearly driven forward such that a roller at the base of the sensor head becomes a pivot joint that can act as a fulcrum to articulate the sensor head. In yet another example, the sensor head can be attached to a 45-degree pivot block that is articulated by the rotation of a corresponding driven pivot block.

The following examples illustrate an operation of endoscopic devices in accordance with various embodiments:

1. Insertion—In its initial straight unarticulated orientation (e.g., FIG. 15A), the endoscopic shaft 10 with the articulating sensor head 14 may be inserted through a trocar into the patient's body, e.g., in the abdominal cavity. A small guiding camera 32 on the distal end of the articulating sensor head (as shown, e.g., in FIGS. 20 and 21) may be used to guide the endoscope to the proper depth and to ensure that it is safe for the scope to move through the trocar opening.

2. Articulation for imaging—Once the scope is in a predetermined or desired position in the body cavity, the sensor head 14 is articulated, e.g., at 90-degrees relative to the shaft 10 as shown in FIG. 15B. The lateral side of the sensor head 14 containing the main collection of cameras or sensors 16 is now positioned and oriented towards the target location.

3. Visualization—The side cameras or sensors 16 facing the target location can visualize the target area while a set of LEDs 30 surrounding the cameras or sensors 16 illuminates the target. In addition, the main endoscope shaft can be rotated and the resulting data captured by the cameras or sensors can be panoramically stitched together. The sensor head 14 can then be articulated to another angle, and the endoscope shaft can be rotated again to further map the target region or area. Finally, the scope can be articulated to face the side cameras or sensors away from the target location. The shaft may be rotated again to perform a comprehensive visualization of the target region or area. In this way, the sensor head can capture a series of images that may be panoramically stitched together to generate a full 3D point cloud providing a comprehensive digital representation of the target region or area.

Figure 23A:
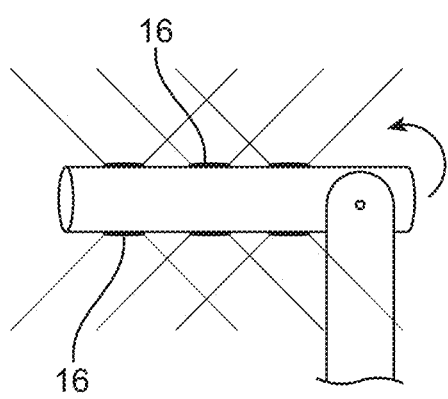
FIG. 23A and FIG. 23B schematically illustrate an exemplary articulating sensor head with multiple cameras mounted on opposite sides of the sensor head, in accordance with some embodiments.
Figure 23B:
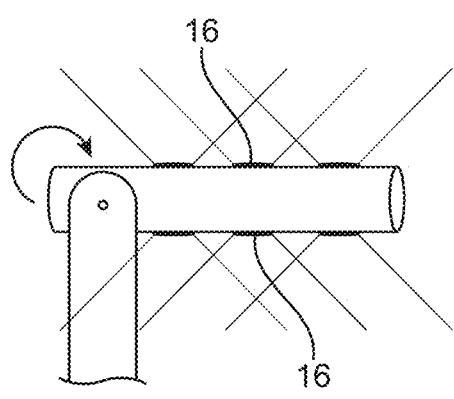

As shown in FIGS. 22A-22D, by rotating the endoscope shaft while the sensor head is in various articulated orientations, the scope is capable of capturing an entire 360-degree field of view of the target region or area in 3D space. FIGS. 23A and 23B illustrate an alternate embodiment in which the articulating sensor head has multiple cameras or sensors 16 mounted on opposite sides of the sensor head. By rotating the endoscope shaft while the sensor head is in various articulated orientations, the scope is capable of capturing an entire 360-degree field of view of the target region or area in 3D space. In any of the embodiments described herein, the endoscope shaft may be rotated while the sensor head is in an articulated orientation to enable the scope to observe the target anatomy from substantially every possible angle.

4. Articulation for removal—Once the visualization is complete, the scope may be articulated back to its straight starting position (e.g., FIG. 15A), rendering the shaft ready to be retracted through its insertion point.

5. Retraction—Now that the shaft is back to its neutral position, the endoscope can be retracted away from the surgical scene and/or removed from the patient's body.

The lateral sides of the articulating sensor heads may provide a large space on which stereo sensors may be arranged with a baseline separation distance that is wider than the baseline separation distance achievable using a conventional forward facing sensor design. The articulating sensor head structure is particularly useful for depth sensing, as a wider baseline separation distance for stereo sensors decreases depth estimation errors.

In accordance with one or more embodiments, the additional space provided by the lateral sides of the articulating sensor head allows for the incorporation of additional depth computation improvement technologies on the lateral sides of said sensor head. The additional depth computation improvement technologies may comprise, for example, a stereoscopic depth sensor, a structured light imaging sensor, and/or a time of flight sensor. In some cases, a pattern projector could be incorporated in the sensor head. The pattern projector can be used in active stereo sensor applications to allow depth computation of targets including, e.g., featureless targets.

In accordance with one or more embodiments, the additional space provided by the lateral sides of the articulating sensor head can accommodate other dedicated sensors, such as IR sensitive sensors, stereoscopic depth sensors, structured light imaging sensors, or time of flight sensors.

The articulation of sensor heads in accordance with various embodiments can also allow for observation of more of the internal environment from a single trocar site than possible with a rigid, non-articulating laparoscope.

Scope Assembly

Recognized herein are various limitations with medical imaging systems currently available. Conventional medical imaging systems (e.g., a scope such as an endoscope) may use a single light signal (e.g., a white light) to visualize a target site (e.g., an internal portion) within a subject. However, such visualization may be limited to two-dimensional representation of the surface of a target site (e.g., a tissue of interest).

The scope assembly of the present disclosure can allow visualization of structures or features of a target site (e.g., an internal tissue site) of a subject with depth perception (or 3D imaging). The scope assembly can work in conjunction, and can be compatible with already existing scope (e.g., a laparoscope) to provide such advanced imaging capacities. The scope assembly can comprise at least one sensor. In some embodiments, the scope assembly can comprise a first sensor (e.g., a 2D camera) for navigating towards a target site of a subject, and a second sensor (e.g., a depth sensor) for accurate imaging of one or more target sites. Thus, the scope assembly need not rely on a same single sensor to perform both 2D imaging and 3D imaging. Both 2D and 3D imaging modes can be capable of being performed concurrently. The scope assembly can be articulating (capable of being articulated) to provide a wide field of view for the sensor(s). The scope assembly can comprise a separate optics assembly to control (or fine-tune) how one or more light beams are directed for imaging, e.g., depth sensing of the target site(s). In addition, the images or videos of the one or more target sites under various wavelengths can be processed (e.g., in real-time or post-processed) to analyze one or more features of the target site(s), e.g., perfusion information of the target site(s). The systems and methods as provided herein are capable of generating a substantially accurate 3D reconstruction of the target site(s), e.g., one or more target tissues.

By enhancing the flexibility and use of existing medical imaging equipment, the scope assembly of the present disclosure need not require or incur expensive capital equipment upgrades in healthcare environments. The scope assembly need not require additional personnel (e.g., technicians or medical practitioners) on site to manage the components and processes, and may require minimal effort to operate. By replacing existing dye-based imaging systems, the scope assembly of the present disclosure may also help to reduce operating room footprint.

The scope assembly of the present disclosure may be useable for a number of medical applications, e.g., general surgery, neurosurgical procedures, orthopedic procedures, and spinal procedures. The scope assembly of the present disclosure may be applicable to a wide variety of endoscopy-based procedures, including, but are not limited to, cholecystectomy (e.g., 1,200,000 procedures per year), hysterectomy (e.g., 575,000 procedures per year), thyroidectomy (e.g., 150,500 procedures per year), and gastrectomy (e.g., 225,000 procedures per year).

In an aspect, the present disclosure provides a scope assembly. The scope assembly may comprise a housing unit configured to enclose at least a portion of an elongated scope, wherein the housing unit is releasably coupled to the at least the portion of the elongated scope. The scope assembly may comprise an imaging unit operably coupled to a distal end of the housing unit, wherein the imaging unit comprises an optics assembly configured to direct one or more light beams that are transmitted through the elongated scope onto a target site within a subject's body. In some cases, the imaging unit may be movable via a rotational or translational motion relative to the housing unit to alter a field of view.

In an aspect, the present disclosure provides a scope assembly. The scope assembly may comprise a housing unit configured to enclose at least a portion of an elongated scope, wherein the housing unit is releasably coupled to the at least the portion of the elongated scope. The scope assembly may comprise an imaging unit operably coupled to a distal end of the housing unit, wherein the imaging unit comprises a camera and a depth sensor on different sides of the imaging unit, such that the camera and the depth sensor have different optical axes. In some cases, the imaging unit may be configured to move relative to the housing unit to alter a field of view of the camera or the depth sensor.

In an aspect, the present disclosure provides a scope assembly. The scope assembly may comprise an elongated scope. The scope assembly may comprise an imaging unit attached to a distal end of the elongated scope, wherein the imaging unit comprises a camera and separately a depth sensor. In some cases, the imaging unit may be movable via a rotational or translational motion relative to the elongated scope to alter a field of view of the camera or the depth sensor.

In an aspect, the present disclosure provides a scope assembly. The scope assembly may comprise an elongated scope. The scope assembly may comprise an imaging unit operably coupled to a distal end of the elongated scope, wherein the imaging unit is configured to (1) move relative to the elongated scope and (2) obtain a plurality of imaging data of a target site from a plurality of perspectives. The scope assembly may comprise one or more motion sensors operatively coupled to the imaging unit, wherein the one or more motion sensors are configured to provide spatial information of the imaging unit as the imaging unit moves relative to the elongated scope. The scope assembly may comprise a processor operatively coupled to the imaging unit and the one or more sensor, wherein the processor is configured to generate a three-dimensional (3D) reconstruction of the target site based on the plurality of imaging data and the spatial information.

In an aspect, the present disclosure provides a scope assembly. The scope assembly may comprise an optical adapter. The optical adapter may comprise a housing comprising a first end configured to releasably couple to an elongated scope, and a second end configured to releasably couple to a camera. The optical adapter may comprise a depth sensor coupled to the housing. The optical adapter may comprise an optics unit disposed in the housing, wherein the optics unit is configured to (1) receive light signals that are reflected from a target site within a subject's body and transmitted through the elongated scope, and (2) reflect a first portion of the light signals onto one of the depth sensor or the camera, while permitting a second portion of the light signals to pass through to the other of the depth sensor or the camera.

In some optional embodiments, the scope assembly may comprise (1) an infrared sensitive monochrome imaging sensor housed within a reusable hardware agnostic adapter that is releasably couplable to (a) a standard 10 mm 0° or 300 rigid laparoscope and (b) any commercially available surgical camera head (e.g. Stryker 1588), and (2) a custom light source that combines white light with one or more coherent laser sources to illuminate the surgical field. Custom optics within the adapter may enable simultaneous imaging of (i) the infrared spectrum of light reflected from the surgical site using an imaging sensor and (ii) the visible spectrum of reflected light using a $3^{rd}$ party commercial camera. An optical element (e.g., a dichroic mirror) may be used to reflect the infrared spectrum of light to the imaging sensor and to direct the visible spectrum of light to the $3^{rd}$ party commercial camera. Proprietary algorithms may be implemented to combine the two images to provide a real-time overlay that provides an indication of blood flow and tissue perfusion to the user. The images and/or the real-time overlay may be further refined, augmented, or updated using one or more depth measurements obtained using any of the depth sensors or depth sensing devices described herein.

The depth-sensing endoscopic visualization systems described herein provide numerous advantages over existing endoscopic imaging systems (e.g., dye-based fluorescence imaging systems) used for intra-operative visualization of in vivo tissue perfusion and vasculature. For instance, the depth-sensing endoscopic visualization systems described herein may be used to (i) perform laser speckle contrast imaging (LSCI) of vasculature and perfusion and (ii) enhance said laser speckle contrast imaging with depth information to aid in the detection of any unrecognized and/or unintended injuries to tissue parenchyma and vascular supply. The depth-sensing endoscopic visualization systems of the present disclosure also provide substantial improvements in real-time imaging capabilities compared to traditional endoscopic visualization systems. During an in vivo test consisting of bowel anastomoses followed by serial devascularizations of the mesentery in a porcine model (n=14), the endoscopic imaging systems disclosed herein were able to detect real-time parenchymal perfusion and mesenteric blood flow with an average processing latency of about 150 ms. In contrast, commercial dye-based fluorescent systems have a processing latency that is about 200 times higher, excluding ICG preparation time (p<0.01). The tissue perfusion signals detected by the endoscopic imaging systems during the in vivo test correlated significantly with the perfusion data (blood pressure and flow) measured using a commercially available FDA-approved laser doppler system (r=0.87, p<0.001).

In addition to improving image processing efficiency and enabling real-time display with minimal latency, the depth-sensing endoscopic visualization systems described herein also provide an effective platform for accurately detecting and quantifying perfusion while minimizing the occurrence of false positive displays. Commercially available dye-based endoscopic imaging systems can only be used accurately once upon devascularization, and will consistently display 100% false positive fluorescent images following serial devascularization due to the retention of fluorescing dyes in certain ischemic segments. Further, variations in fluorescence intensity can further accentuate the false positive display in such commercially available systems. In contrast, the depth-sensing endoscopic imaging systems of the present disclosure display no such false positives associated with dye-based endoscopic imaging.

The depth-sensing endoscopic imaging systems described herein further enhance usability as compared to other commercially available endoscopic imaging systems. For example, the depth-sensing endoscopic imaging systems of the present disclosure can be used to streamline clinical workflow and reduce operational costs associated with dye administration, since no drug prep or dye injection is required.

In an aspect, the present disclosure provides an imaging kit comprising any one of the scope assembly disclosed herein, and an illumination source configured to transmit the one or more light beams to and through the elongated scope.

In an aspect, the present disclosure provides a method of using any one of the scope assembly disclosed herein.

In an aspect, the present disclosure provides a method comprising providing a scope assembly comprising (i) a housing unit configured to enclose at least a portion of an elongated scope, wherein the housing unit is releasably coupled to the at least the portion of the elongated scope, and (ii) an imaging unit operably coupled to a distal end of the housing unit, wherein the imaging unit comprises an optics assembly configured to direct one or more light beams that are transmitted through the elongated scope onto a target site within a subject's body. The method may further comprise receiving, by the optics assembly, the one or more light beams from the elongated scope. The method may further comprise directing, by the optics assembly, the one or more light beams onto the target site within the subject's body. In some cases, the method may further comprise moving the imaging unit via a rotational or translational motion relative to the housing unit to direct the one or more light beams onto the target site within the subject's body.

In an aspect, the present disclosure provides a method comprising providing a scope assembly comprising (i) a housing unit configured to enclose at least a portion of an elongated scope, wherein the housing unit is releasably coupled to the at least the portion of the elongated scope, and (ii) an imaging unit operably coupled to a distal end of the housing unit, wherein the imaging unit comprises a camera and a depth sensor on different sides of the imaging unit. The method may further comprise, with aid of the camera, receiving a first light signal from a first optical axis. The method may further comprise, with aid of the depth sensor, receiving a second light signal from a second optical axis that is different from the first optical axis. In some cases, the method may further comprise moving the imaging unit via a rotational or translational motion relative to the housing unit to alter a field of view of the camera or the depth sensor.

In an aspect, the present disclosure provides a method comprising providing a scope assembly comprising (i) an elongated scope and (ii) an imaging unit attached to a distal end of the elongated scope, wherein the imaging unit comprises a camera and separately a depth sensor. The method may further comprise, with aid of the camera, generating a first set of imaging data comprising two-dimensional (2D) photographic or video images. The method may further comprise, with aid of the depth sensor, generating a second set of imaging data comprising depth maps. In some cases, the method may further comprise moving the imaging unit via a rotational or translational motion relative to the elongated scope to alter a field of view of the camera or the depth sensor.

In an aspect, the present disclosure provides a method comprising providing a scope assembly comprising (i) an elongated scope, (ii) an imaging unit operatively coupled to a distal end of the elongated scope, and (iii) one or more motion sensors operatively coupled to the imaging unit. The method may further comprise moving the imaging unit relative to the elongated scope to obtain a plurality of imaging data of a target site from a plurality of perspectives. The method may further comprise, with aid of the one or more motion sensors, providing spatial information of the imaging unit as the imaging unit moves relative to the elongated scope. The method may further comprise, with aid of a processor, generating a three-dimensional (3D) reconstruction of the target site based on the plurality of imaging data and the spatial information.

In an aspect, the present disclosure provides a method comprising providing a scope assembly comprising an optical adapter, wherein the optical adapter comprises (i) a housing comprising a first end configured to releasably couple to an elongated scope, and a second end configured to releasably couple to a camera, (ii) a depth sensor coupled to the housing, and (iii) an optics unit disposed in the housing. The method may further comprise, with aid of the optics unit, (1) receiving light signals that are reflected from a target site within a subject's body and transmitted through the elongated scope, and (2) reflecting a first portion of the light signals onto one of the depth sensor or the camera, while permitting a second portion of the light signals to pass through to the other of the depth sensor or the camera.

In an aspect, the present disclosure provides a scope assembly, e.g., for medical imaging. The scope assembly may comprise a housing unit configured to enclose at least a portion of an elongated scope. The scope assembly may further comprise an imaging unit operably coupled to the housing unit. The imaging unit may comprise an optics assembly configured to (i) receive one or more light beams that are transmitted through the elongated scope and (ii) direct at least a portion of the one or more light beams onto one or more locations (e.g., two or more locations) within a subject's body. In some cases, at least one of the two or more locations may comprise a target site, e.g., a target tissue to be imaged or subjected to a surgical procedure.

The elongated scope may be at least a portion of a scope device configured to visualize external and/or inner surface of a tissue (e.g., skin or internal organ) of a subject. The scope device may be used to (i) examine (e.g., visually examine) the tissue of the subject and (ii) diagnose and/or assist in a medical intervention (e.g., treatments, such as a surgery). The scope device may be an already existing endoscope. Examples of the endoscope may include, but are not limited to, a cystoscope (bladder), nephroscope (kidney), bronchoscope (bronchus), arthroscope (joints) and colonoscope (colon), and laparoscope (abdomen or pelvis).

The scope assembly (or at least a portion of the scope assembly, e.g., the housing unit or the imaging unit) may be reused, and may be interchangeable with different scope devices. In some cases, the scope assembly may allow a scope from any existing scope device (e.g., a third-party laparoscope) to be operatively coupled to one or more additional sensors (e.g., a 2D camera and/or a depth sensor), thereby further diversifying imaging modalities of the existing scope device.

In some cases, the housing unit may be a sleeve (e.g., a hollow sleeve) configured to enclose at least a portion of the elongated scope. The housing unit may have a cross-section that is circular, triangular, square, rectangular, pentagonal, hexagonal, or any partial shape or combination of shapes thereof. The cross-sectional shape of the housing unit may be the same as a cross-sectional shape of the elongated scope. In other embodiments, the cross-sectional shape of the housing unit may not or need not be the same as the cross-sectional shape of the elongated scope.

In some cases, the housing unit may be configured to couple to the portion of the elongated scope. Examples of a coupling mechanism to couple the housing unit to the portion of the elongated scope may include, but are not limited to, magnets (e.g., electromagnet or permanent magnet), mechanical tethers (e.g., string or thread tethers), adhesives (e.g., solids, semi-solids, gels, viscous liquids, etc.), male-to-female fasteners (e.g., mating or interlocking fasteners, hooks and holes, hooks and loops such as Velcro™, a female nut threaded onto a male bolt, a male protrusion inserted into a female indentation in LEGO blocks, a male threaded pipe fitted into a female threaded elbow in plumbing, a male universal serial bus (USB) plug inserted into a female USB socket, etc.), screw-on coupling (e.g., with or without a coaxial connector), elastic coupling, gear coupling, hydrodynamic coupling, and other gasping mechanisms such as robotic arms that hold two or more components operatively relative to each other.

In some cases, the housing unit may be releasably coupled to the elongated scope via one or more quick release mechanisms (e.g., snap-fit, latches, etc.). The quick release mechanism may be configured to releasably couple the housing unit to various types of elongated scopes having different sizes. In an example, the housing unit (e.g., an end of the housing unit configured to couple to the elongated scope) may comprise different sections with varied dimensions (e.g., different radial dimensions) configured to releasably coupled to different elongated scopes having different sizes. In another example, the housing unit may comprise an adjustable aperture mechanism with adjustable aperture diameter to accommodate different elongated scopes having different sizes. The quick release mechanism may be configured to quickly move between a lock position (i.e., a coupled position) and a release position (i.e., a non-coupled position) in response to one or more movements of the quick release mechanism, such as a single, non-repetitious movement (e.g., lateral or rotational) of the quick release mechanism. The quick release mechanism may be configured to quickly move between a lock and a release position in response to a user instruction via a switch, e.g., a mechanical switch disposed on the housing unit or the elongated scope.

The quick release mechanism may be configured to permit the user to releasably couple the housing unit to the elongated scope without use of tools. Alternatively, the quick release mechanism may be configured to permit the user to releasably couple the housing unit to the scope with one or more tools, e.g., one or more keys to operatively coupled to the quick release mechanism to activate release of the quick release mechanism. The quick release mechanism may be configured to permit the user to releasably couple the housing unit to the elongated scope in less than 60 seconds. The quick release mechanism may be configured to permit the user to releasably couple the housing unit to the elongated scope in less than 60 seconds, 55 seconds, 50 seconds, 45 seconds, 40 seconds, 35 seconds, 30 seconds, 25 seconds, 20 seconds, 15 seconds, 10 seconds, 5 seconds, or less.

The quick release mechanism may allow for precise coupling of two members, such as that of the housing unit to the elongated scope. The precise coupling may provide an optimal optical path between the two members. The precise coupling may be achieved within an accuracy of less than about 20 micrometers (μm). In some cases, the precise coupling may be achieved within an accuracy of at most about 100 μm, 90 μm, 80 μm, 70 μm, 60 μm, 50 μm, 40 μm, 30 μm, 20 μm, 10 μm, 9 μm, 8 μm, 7 μm, 6 μm, 5 μm, μm, 3 μm, 2 μm, 1 μm, 900 nanometers (nm), 800 nm, 700 nm, 600 nm, 500 nm, 400 nm, 300 nm, 200 nm, 100 nm, 50 nm, or less.

In some cases, the coupling between the housing unit and the elongated scope may not or need not utilize a quick release mechanism. In some cases, the housing unit may be screwed on to the elongated scope, thereby preventing a quick release of the housing unit from the elongated scope. In an example, a coupling surface (e.g., an inner surface) of the housing unit may substantially mimic the structure of a coupling surface of the elongated scope.

In some cases, the housing unit may further comprise one or more grasping mechanisms to reduce (e.g., prevent) undesirable movement of the elongated scope within the housing unit during use of the scope assembly. In some cases, the one or more grasping mechanisms may be activated on demand, such that the initial insertion of the elongated scope into the housing unit is not prohibited. Examples of such grasping mechanism may include, but are not limited to, a mechanical handle, an expandable balloon, screws, etc. Alternatively or in addition to, an inner surface of the housing unit may be textured to reduce (e.g., prevent) such undesirable movement of the elongated scope within the housing unit.

In addition to the elongated scope, the housing unit of the scope assembly may be configured to enclose (or releasably couple to) at least one additional device. In some cases, the at least one additional device may comprise one or more endoscopic surgical tools. The one or more endoscopic surgical tool may be operated manually (e.g., by a medical practitioner, such as a surgeon or a specialist). Alternatively, the one or more endoscopic surgical tool may be operated automatically (e.g., da Vinci surgical instruments). By being coupled to the at least one additional device, functional modalities of the scope assembly of the present disclosure may be diversified into a number of applications, e.g., cholecystectomy, appendectomy, laparoscopic bariatric surgery, hernia repair, large and small intestine, colon and hemorrhoid surgery, and biopsy (e.g., liver biopsy, breast biopsy, tumor or cancer biopsy, etc.). Examples of the one or more endoscopic surgical tools may include, but are not limited to an arthroscopy forcep, grasping forcep, punch forcep, scissors, meniscus, meniscotome, knife, rasp, probe, curette, trocar, suction tube, etc.

Thus, in some cases, the housing unit of the scope assembly may be configured to enclose (or releasably couple to) an elongated scope and at least one endoscopic surgical tool, thereby allowing both visualization of a target tissue and surgical performance by a single instrumentation unit.

In some cases, the imaging unit may be coupled to the housing unit, via any one of the abovementioned coupling mechanisms. In some cases, the imaging unit may be releasably coupled to the housing unit, via any one of the abovementioned quick release mechanisms.

In some cases, the scope assembly may be articulating, such that at least a portion of the imaging unit is movable relative to the housing unit. In some cases, the imaging unit may be configured to move via a rotational and/or translational motion relative to the housing unit to alter a field of view when imaging within the subject's body. The imaging unit may be configured to move via a rotational motion relative to the housing unit. Alternatively, the imaging unit may be configured to move via a translational motion relative to the housing unit. In another alternative, the imaging unit may be configured to move via both rotational and translational motions relative to the housing unit.

In some cases, the imaging unit may be operably coupled to the housing unit via at least one joint mechanism that is configured to permit the imaging unit to move in one or more degrees of freedom. The joint mechanism may permit the imaging unit to move in at least 1, 2, 3, 4, 5, 6, 7, 8, 9, 10, or more degrees of freedom. The joint mechanism may permit the imaging unit to move in at most at most 10, 9, 8, 7, 6, 5, 4, 3, 2, or 1 degree of freedom. The imaging unit may be operatively coupled to the housing unit via at least 1, 2, 3, 4, 5, 6, 7, 8, 9, 10, or more joint mechanisms. The imaging unit may be operatively coupled to the housing unit via at most 10, 9, 8, 7, 6, 5, 4, 3, 2, or 1 joint mechanism. In some cases, the imaging unit may be operatively coupled to a plurality of joint mechanisms, and one or more individual joint mechanism of the plurality of joint mechanisms may be coupled to one another. In other embodiments, the imaging unit may be operatively coupled to a plurality of joint mechanisms, and one or more individual joint mechanism of the plurality of joint mechanisms may not or need not be coupled to one another. Such movement of the imaging unit may be a relative movement. Thus, a moving piece may be the imaging unit, the housing unit, or both the imaging unit and the housing unit.

A joint mechanism of the present disclosure (e.g., to permit movement of the imaging unit relative to the housing unit) may comprise, for example, a pivot joint, a hinge joint, a saddle joint, a condyloid joint, a ball and socket joint, variations thereof, or combinations thereof. In some cases, a joint mechanism may be operatively coupled to one or more actuators configured to direct the movement of the imaging unit. For example, a joint mechanism may comprise the one or more actuators. In another example, a joint mechanism may be directly coupled to the one or more actuators. In a different example, a joint mechanism may be indirectly coupled to the one or more actuators, wherein a movement of another object (e.g., another component of the scope assembly, such as a gearing mechanism) via the one or more actuators may effect movement of the imaging unit in one or more degrees of freedom. Examples of the one or more actuators may include, but are not limited to, a hydraulic actuator, a pneumatic actuator, an electric actuator (e.g., an electric motor), a twisted and coiled polymer (TCP) or supercoiled polymer (SCP) actuator, a thermal actuator, a magnetic actuator, a mechanical actuator, a piezoelectric actuator, variations thereof, and combinations thereof.

In some cases, the imaging unit may be extendable and retractable with respect to the housing unit. In some cases, the imaging unit may be disposable and replaceable with another imaging unit.

In an example, the scope assembly may have one joint mechanism, e.g., at a junction between the housing unit and the imaging unit. In other examples, the scope assembly may have two or more joint mechanisms at two or more different locations between the housing unit and the imaging unit, thereby to allow movement with more degrees of freedom. In such cases, the two or more joint mechanisms may be operated (e.g., manually or automatically) in unison (e.g., moving one joint mechanism may automatically move another joint mechanism), or each joint mechanism of the two or more joint mechanisms may be operated independently (e.g., manually or automatically).

Alternatively, the scope assembly may not or need not be articulating, and the imaging unit may not or need not be configured to move relative to the housing unit.

In some cases, the scope assembly may comprise a motion sensor (or a position sensor). The motion sensor may be operatively coupled to the housing unit, the imaging unit, or both the housing unit and the imaging unit. The motion sensor may be a part of the housing unit, the imaging unit, or both the housing unit and the imaging unit. The motion sensor may be able to measure (and record) a relative movement (e.g., rotational and/or translational) between the imaging unit and the housing unit. In some cases, the motion sensor may be able to measure (and record) a relative movement of the scope assembly (or one or more of its components, such as the imaging unit and/or the housing unit) to a portion of the elongated scope that is not enclosed by the housing unit. In some cases, the measured movements may comprise spatio-temporal movement data of the imaging unit during use of the scope assembly. The measured movements may be combined, e.g., by a computer processor, with imaging data (e.g., images or videos) from the imaging unit to produce a 3D reconstruction of the target site.

The scope assembly may comprise at least 1, 2, 3, 4, 5, 6, 7, 8, 9, 10, or more motion sensors. The scopes assembly may comprise at most 10, 9, 8, 7, 6, 5, 4, 3, 2, or 1 motion sensor. Examples of the motion sensor may include, but are not limited to, an inertial measurement unit (IMU), such as an accelerometer (e.g., a three-axes accelerometer), a gyroscope (e.g., a three-axes gyroscope), or a magnetometer (e.g., a three-axes magnetometer). The IMU may be configured to sense position, orientation, and/or sudden accelerations (lateral, vertical, pitch, roll, and/or yaw, etc.) of at least a portion of the scope assembly, such as the imaging unit.

The one or more light beams transmitted through the elongated scope may comprise a single light beam from a single light source. Alternatively, the one or more light beams may be a combined light beam comprising a plurality of light beams. The plurality of light beams may be directed from a single optical source or a plurality of optical sources. The plurality of light beams may include at least 2, 3, 4, 5, 6, 7, 8, 9, 10, or more light beams. The plurality of light beams may include at most 10, 9, 8, 7, 6, 5, 4, 3, or 2 light beams.

In some cases, the plurality of light beams may comprise (i) a white light and (ii) one or more laser beams (e.g., one or more coherent laser lights). The white light may comprise one or more wavelengths from a visible electromagnetic spectrum, ranging from about 400 nanometers (nm) (or 0.4 micrometers (μm)) to about 700 nm (or 0.7 μm). The one or more laser beams may include at least 1, 2, 3, 4, 5, 6, 7, 8, 9, 10, or more laser beams. The one or more laser beams may include at most 10, 9, 8, 7, 6, 5, 4, 3, 2, or 1 laser beam. The one or more laser beams may comprise one or more wavelengths from an invisible electromagnetic spectrum. The invisible spectrum may comprise wavelengths (i) greater than about 700 nm and/or (ii) less than about 400 nm. In some cases, the invisible spectrum may comprise wavelengths (i) greater than about 770 nm and/or (ii) less than about 390 nm.

In some cases, the white light may comprise one or more wavelengths from about 400 nm to about 700 nm. The white light may comprise one or more wavelengths from at least about 400 nm. The white light may comprise one or more wavelengths from at most about 700 nm. The white light may comprise one or more wavelengths from about 400 nm to about 450 nm, about 400 nm to about 500 nm, about 400 nm to about 550 nm, about 400 nm to about 600 nm, about 400 nm to about 650 nm, about 400 nm to about 700 nm, about 450 nm to about 500 nm, about 450 nm to about 550 nm, about 450 nm to about 600 nm, about 450 nm to about 650 nm, about 450 nm to about 700 nm, about 500 nm to about 550 nm, about 500 nm to about 600 nm, about 500 nm to about 650 nm, about 500 nm to about 700 nm, about 550 nm to about 600 nm, about 550 nm to about 650 nm, about 550 nm to about 700 nm, about 600 nm to about 650 nm, about 600 nm to about 700 nm, or about 650 nm to about 700 nm. The white light may comprise one or more wavelengths from about 400 nm, about 450 nm, about 500 nm, about 550 nm, about 600 nm, about 650 nm, or about 700 nm.

In some cases, the one or more laser beams may comprise one or more wavelengths from about 0.7 μm to about 1,000 μm. The one or more laser beams may comprise one or more wavelengths from at least about 0.7 μm. The one or more laser beams may comprise one or more wavelengths from at most about 1,000 μm. The one or more laser beams may comprise one or more wavelengths from about 0.7 μm to about 1 μm, about 0.7 μm to about 5 μm, about 0.7 μm to about 10 μm, about 0.7 μm to about 50 μm, about 0.7 μm to about 100 μm, about 0.7 μm to about 500 μm, about 0.7 μm to about 1,000 μm, about 1 μm to about 5 μm, about 1 μm to about 10 μm, about 1 μm to about 50 μm, about 1 μm to about 100 μm, about 1 μm to about 500 μm, about 1 μm to about 1,000 μm, about 5 μm to about 10 μm, about 5 μm to about 50 μm, about 5 μm to about 100 μm, about 5 μm to about 500 μm, about 5 μm to about 1,000 μm, about 10 μm to about 50 μm, about 10 μm to about 100 μm, about 10 μm to about 500 μm, about 10 μm to about 1,000 μm, about 50 μm to about 100 μm, about 50 μm to about 500 μm, about 50 μm to about 1,000 μm, about 100 μm to about 500 μm, about 100 μm to about 1,000 μm, or about 500 μm to about 1,000 μm. The one or more laser beams may comprise one or more wavelengths from about 0.7 μm, about 1 μm, about 5 μm, about 10 μm, about 50 μm, about 100 μm, about 500 μm, or about 1,000 μm.

In some cases, the white light and the one or more coherent laser lights may be directed through the elongated scope and towards the scope assembly via a plurality of optical paths, e.g., a first optical path for the white light and one or more second optical paths for the one or more coherent laser lights. In an example, the plurality of optical paths may comprise a plurality of optical fibers. Alternatively, the white light and the one or more coherent laser lights may be directed through the elongated scope and towards the scope assembly via a single optical path.

The optics assembly of the scope assembly may comprise one or more mirrors. In some cases, the mirror(s) may receive the one or more light beams from the elongated scope and reflect at least a portion of the light beam(s) towards a target direction. Thus, the one or more mirrors may change an optical axis of the at least the portion of the light beam(s), e.g., bend at least the portion of the light beam(s).

In some cases, the one or more mirrors may be configured to move relative to an optical path of the one or more light beams. In some cases, the one or more mirrors may be configured to move (e.g., flip down, fold over, rotate, etc.) out of the optical path, thereby allowing the one or more light beams to travel through the imaging unit and towards a subject's body without being interrupted by the optics assembly.

In some cases, the optics assembly may comprise a beam splitter. Examples of the beam splitter may include, but are not limited to, a half mirror, a dichroic beam splitter (e.g., a shortpass or longpass dichroic mirror), or a multi-band beam splitter. In an example, the beam splitter may be a cube comprising two prisms (e.g., two triangular glass prisms) disposed adjacent to each other. The beam splitter may be configured to receive the light beam(s) from the elongated scope, and reflect (or permit to pass through) a first portion of the light beam(s) to the target site, while permitting a second portion of the one or more light beams to pass through (or reflect) to another location of the two or more locations within the subject's body.

In an example, the beam splitter (e.g., comprising a shortpass dichroic mirror) may be configured to receive the light beam(s) from the elongated scope and (i) reflect a first portion of the light beam(s) (e.g., coherent laser beam(s)) toward the target site and (ii) permit a second portion of the light beam(s) (e.g., white light) to pass through to another location of the two or more locations within the subject's body. Alternatively, the beam splitter (e.g., comprising a longpass dichroic mirror) may be configured to receive the light beam(s) from the elongated scope and (i) reflect the second portion of the light beam(s) (e.g., white light) toward the target site, and (ii) permit the first portion of the light beam(s) (e.g., coherent laser beam(s)) to pass through to another location of the two or more locations within the subject's body.

In another example, the beam splitter may be a polarizing beam splitter, e.g., a Wollaston prism. The polarizing beam splitter may be configured to receive light signals from the target site and (i) reflect the first portion of the light signals that is in first polarization toward the target site, and (ii) permit the second portion of the light signals in second polarization to pass through toward another location of the two or more locations within the subject's body.

The optics assembly may not or need not comprise any focusing device (e.g., an optical aperture, such as an objective lens) ahead of the beam splitter (e.g., before the light signals reach the beam splitter). Alternatively, the optics assembly may comprise one or more focusing devices ahead of the beam splitter. The optics assembly may comprise at least 1, 2, 3, 4, 5, or more focusing devices disposed ahead of the beam splitter. The optics assembly may comprise at most 5, 4, 3, 2, or 1 focusing device disposed ahead of the beam splitter.

A focusing device, as used herein in the present disclosure, may comprise any lens (e.g., fish-eye, elliptical, conical, etc.), reflector, optic, concentrator, or other device that is capable of reflecting or focusing light. In an example, the focusing device may be a relay lens. The optics assembly may comprise at least one focusing device (e.g., at least 1, 2, 3, 4, 5, or more focusing devices). The at least one focusing device may be disposed between (i) the beam splitter and elongated scope and/or (ii) the beam splitter and the one or more locations of the imaging unit.

In some cases, an angle of the optics assembly within the imaging unit may be fixed. In such case, the angle of the optics assembly may be stationary regardless of any relative movement between the housing unit and the imaging unit.

In some cases, the angle of the optics assembly within the imaging unit may be adjustable. The optics assembly may be adjusted by tilting, rotating, and/or moving translationally. In some cases, the optics assembly may be disposed within a body (or an enclosure) of the imaging unit or within the housing unit, such that a relative movement between the imaging unit and the housing unit may respectively adjust the angle of the optics assembly. In some examples, the optics assembly may be disposed within the imaging unit at a fixed angle to direct a first portion of the light beam(s) towards a first section of the imaging unit and a second portion of the light beam(s) towards a second section of the imaging unit. The first portion of the light beam(s) may be directed through the first section of the imaging unit and towards a first location within the subject's body. The second portion of the light beam(s) may be directed through the second section of the imaging unit and towards a second location within the subject's body. Any articulation (or movement) of the imaging unit relative to the housing unit may thus adjust the angle of the optics assembly relative to the housing unit, respectively, such that the optical axis (e.g., positioning, angle, distance, etc.) between (i) the optics assembly and the first section and (ii) the optics assembly and the second section may remain substantially the same as prior to the relative movement between the imaging unit and the housing unit.

Alternatively, the angle of the optics assembly may be adjustable independent of the movement of the imaging unit. For example, the angle of the optics assembly (e.g., one or more mirrors) may be adjustable (e.g., mechanically or electronically) relative to the imaging unit (e.g., the first and/or second section of the imaging unit, any sensor within the imaging unit) and/or the housing unit. The angle of the optics assembly may be adjusted (e.g., manually or automatically) independent of the movement of the imaging unit (and/or the housing unit) prior to, concurrent with, and/or subsequent to use of the scope assembly. In some examples, the angle of the optics assembly may be adjusted independently for calibration of optical path(s) from and towards the optics assembly, e.g., (i) between the optics assembly and the first section of the imaging unit and (ii) between the optics assembly and the second section of the imaging unit.

The imaging unit may comprise at least one sensor configured to detect visualization (e.g., images or videos) of one or more locations within the subject's body. The at least one sensor may be a 2D camera. The at least one sensor may be a depth sensor. The imaging unit may comprise at least 1, 2, 3, 4, 5, 6, 7, 8, 9, 10, or more sensors. The imaging unit may comprise at most 10, 9, 8, 7, 6, 5, 4, 3, 2, or 1 sensor. The imaging unit may comprise a plurality of sensors at a same section within the imaging unit. Alternatively, the imaging unit may comprise a plurality of sensors at different sections within the imaging unit. The at least one sensor may be communicatively coupled to a processor (e.g., an imaging processor) to generate one or more imaging data of the one or more locations within the subject's body. The at least one sensor may communicatively couple to the processor. The at least one sensor may be wired to the processor. Alternatively, the at least one sensor may comprise at least one communications device (e.g., RFID, NFC, Bluetooth, Wi-Fi, etc.) to communicate with the processor.

In some cases, the imaging unit may comprise a first sensor (e.g., a 2D camera) at a first section (e.g., a distal end) of the imaging unit. The first sensor may be used to navigate within the subject's body towards a target site. The target site may be a site of interest for imaging, obtaining a biopsy sample, and/or a surgical procedure. Once a first portion of the light beam(s) is directed by the optics assembly through the first section of the imaging unit and towards a first location within the subject's body, a first light signal may be reflected or emitted by the first location and towards the first sensor for imaging. Additionally, the imaging unit may comprise a second sensor (e.g., a depth sensor) at a second section (e.g., a side different than the distal end) of the imaging unit. Once the scope assembly has reached the target site, the second sensor may be used to visualize the target site. Once a second portion of the light beam(s) is directed by the optics assembly through the second section of the imaging unit and towards a second location (e.g., the target site) within the subject's body, a second light signal may be reflected or emitted by the second location and towards the second sensor for imaging.

The first sensor may generate a first set of imaging data, and the second sensor may generate a second set of imaging data. The second set of imaging data may comprise more information (e.g., higher resolution, depth imaging, 3D imaging, reconstruction of the target site, laser speckle imaging, ToF, etc.) than the first set of imaging data (e.g., 2D images and/or videos). In some cases, the first sensor and the second sensor may be used concurrently for multi-imaging. In some cases, the first set and the second set of imaging data may be combined to analyze one or more locations within the subject's body. In some cases, one or more of the first set and the second set of imaging data may be combined with the spatio-temporal movement data of the motion sensor to generate a 3D reconstruction of the one or more locations within the subject's body.

In some cases, the imaging unit may further comprise a depth sensor configured to receive a first light signal that is reflected from the target site upon exposure to the at least the portion of the one or more light beams directed by the optics assembly. The depth sensor may utilize one or more imaging techniques including, but are not limited to, stereo triangulation (e.g., stereoscopic imaging), sheet of light triangulation, structured light imaging, time-of-flight, interferometry, and coded aperture. In an example, the depth sensor may be a stereoscopic camera having at least two lenses. The stereoscopic camera may comprise a first lens adjacent to a second lens. The first and second lenses may be separated by a distance. The distance may be indicative of a measurable depth of the stereoscopic camera. The distance may be at least 0.1 μm, 0.5 μm, 1 μm, 5 μm, 10 μm, 50 μm, 100 μm, 500 μm, 1 mm, 5 mm, 10 mm, 50 mm, or more. The distance may be at most 50 mm, 10 mm, 5 mm, 1 mm, 500 μm, 100 μm, 50 μm, 10 μm, 5 μm, 1 μm, 0.5 μm, 0.1 μm, or less.

In some cases, the depth sensor may be a ToF sensor. The ToF sensor displaced on a surface of the imaging unit may be referred to as a chip-on-top ToF sensor. The ToF sensor may communicatively couple to a processor. The processor may be configured to perform one or more functions. The processor may be configured to operatively couple the ToF sensor to an optical source for the ToF light. In an example, the optical source may accept white light from a $3^{rd}$ party surgical light source, combine the white light with the ToF light, and directing the resulting combined light beams through the extended scope and towards the optics assembly (e.g., using an optical light guide to fiber bundle of the extended scope). Alternatively or in addition to, the processor may be configured to receive imaging data from the ToF sensor compute the depth of the imaged target site within the subject's body. Alternatively or in addition to, the processor may be configured to combine the depth information with a different imaging data set, e.g., from a third party sensor in communication with the elongated scope or from another sensor (e.g., a 2D camera) of the imaging unit of the scope assembly.

One of more wavelengths of the ToF light may be selected such that the wavelength(s) do not interfere with third party sensor or another sensor of the imaging unit. For example, the white light illumination for the party sensor or another sensor may be peaked instead of uniform. The ToF light wavelength(s) may be selected to correspond to one of the valleys in the spectrum of the white light. The beam splitter would then receive combined light beams comprising the white light and the ToF light wavelength(s), and redirect (reflect or transmit) the ToF light wavelengths towards the ToF sensor, while directing the rest of the combined light beams towards the third party video camera or another sensor of the imaging unit.

In some cases, the ToF wavelength(s) may be chosen to either penetrate the target site of the subject (e.g., for subsurface depth measurement) or to be reflected by the most superficial surface of the target site (e.g., for high accuracy surface depth measurement).

In some cases, the accuracy of ToF imaging may depend on a total distance traveled by the ToF light. An optical source of the ToF light may be connected to the extended scope by means of a light guide. Alternatively, the optical source may be placed within the scope assembly, thereby to decrease the distance traveled by the ToF light, providing potentially greater depth resolution.

The ToF sensor may be a low resolution ToF sensor. The low resolution ToF sensor may be smaller in size than higher resolution ToF sensors. Alternatively, the ToF sensor may be a high resolution ToF sensor.

In some cases, the ToF sensor may be a traditional camera sensor (e.g., not originally intended for ToF imaging) that uses heterodyne interferometry. While traditional ToF sensors may be capable of sensing light at high frequency (e.g., within in the megahertz (MHz) range, such ToF sensors may be bulky. In comparison, heterodyne interferometry may allow a traditional camera sensor to be used for ToF depth sensing, by sensing a slower interference wave and back-calculating the phase of the original ToF light. One or more aspects of heterodyne interferometry can be used for ToF imaging, as described in A. Kadambi et al., *IEEE Access*, vol. 5, November 2017 and Li et al., *IEEE ICCP,* 2018: 1-10.

In some cases, the imaging unit may further comprise a camera configured to receive a second light signal that is reflected from the target site or another location of the two or more locations within the subject's body. The camera may be a 2D camera. An example of the camera may be a red, green, and blue (RGB) camera.

In some case, an optical axis of the depth sensor and an optical axis of the camera may be different. The optical axis of the depth sensor may be an optical axis between the target site and the depth sensor. The optical axis of the depth sensor may be substantially parallel to an optical axis between the optics assembly and the target site. The optical axis of the camera may be an optical axis between a different location within the subject's body and the camera. The optical axis of the camera may be substantially parallel to an optical axis between the optics assembly and the different location within the subject's body. In some cases, the optical axis of the depth sensor and the optical axis of the camera may be non-parallel to each other. The optical axis of the depth sensor and the optical axis of the camera may be different by at least 1, 2, 3, 4, 5, 6, 7, 8, 9, 10, 20, 30, 40, 50, 60, 70, 80, 90, or more degrees. The optical axis of the depth sensor and the optical axis of the camera may be different by at most 90, 80, 70, 60, 50, 40, 30, 20, 10, 9, 8, 7, 6, 5, 4, 3, 2, or 1 degree. In an example, the optical axis of the depth sensor may be substantially orthogonal to the optical axis of the camera. Alternatively, the optical axis of the depth sensor and the optical axis of the camera may have parallel but different longitudinal optical axes.

The optical axis of the depth sensor and the optical axis of the camera may intersect at an angle of at least 1 degree, 2 degrees, 3 degrees, 4 degrees, 5 degrees, 6 degrees, 7 degrees, 8 degrees, 9 degrees, 10 degrees, 20 degrees, 30 degrees, 40 degrees, 50 degrees, 60 degrees, 70 degrees, 80 degrees, 90 degrees, or more. The optical axis of the depth sensor and the optical axis of the camera may intersect at an angle of at most 90 degrees, 80 degrees, 70 degrees, 60 degrees, 50 degrees, 40 degrees, 30 degrees, 20 degrees, 10 degrees, 9 degrees, 8 degrees, 7 degrees, 6 degrees, 5 degrees, 4 degrees, 3 degrees, 2 degrees, 1 degree, or less.

In some cases, the depth sensor may be configured to generate a first set of imaging data from the first light signal, and the camera may be configured to generate a second set of imaging data from the second light signal. The first set of imaging data may comprise photographic or video images containing depth information, and the second set of imaging data comprises two-dimensional photographic or video images. The first set of imaging data may comprise a depth map of the target site. The depth map (or a disparity map) may be a 2D representation of the 3D visual scene (e.g., the target site within the subject's body), wherein a value of each element (e.g., pixel) of the 2D representation may be indicative of the distance between the depth sensor and the respective position of the target site within the subject's body. In some cases, the first set and the second set of imaging data may be used separately or may be combined for analysis of one or more locations within the subject's body.

The scope assembly may be disposable and configured for single use in a medical imaging procedure. Alternatively, the scope assembly may be configured to be reusable for a plurality of medical imaging procedures. The plurality of medical imaging procedures may be for the same subject (e.g., the same patient) or for a plurality of different subjects. The scope assembly may be reusable for at least 2, 3, 4, 5, 6, 7, 8, 9, 10, or more medical imaging procedures. The scope assembly may be reusable for at most 10, 9, 8, 7, 6, 5, 4, 3, or 2 medical imaging procedures. In some cases, the scope assembly may be autoclavable for a sterile subsequent use.

The scope assembly of the present disclosure (e.g., the housing unit and/or the imaging unit) may include one or more biologically acceptable and/or compatible materials suitable for medical applications, depending on the particular application and/or preference of a medical practitioner. For example, components of the scope assembly may include or be fabricated from materials such as polyvinyl chloride, polyvinylidene chloride, low density polyethylene, linear low density polyethylene, polyisobutene, poly(ethylene-vinylacetate) copolymer, lightweight aluminum foil and combinations thereof, stainless steel alloys, commercially pure titanium, titanium alloys, silver alloys, copper alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaS04 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, glass, variations thereof, and combinations thereof.

At least a portion of the scope assembly may be opaque, semi-transparent, or transparent. In some cases, the scope assembly may be opaque and configured to block any external light from (i) entering through the scope assembly into one or more components within the scope assembly (e.g., the imaging unit) and (ii) interfering with the one or more light signals directed to or directed from the target site of the subject.

Pressure inside the scope assembly may be approximately the same as ambient pressure (e.g., atmospheric pressure). Alternatively, the pressure inside the scope assembly may be controlled (or regulated, e.g., manually or automatically) such that the inner pressure of the scope assembly is lower or higher than the ambient pressure. Temperature inside the scope assembly may be approximately the same as ambient temperature (e.g., room temperature). Alternatively, the temperature inside the scope assembly may be controlled (or regulated, e.g., manually or automatically) such that the inner temperature of the scope assembly is lower or higher than the ambient temperature. Humidity inside the scope assembly may be approximately the same as ambient humidity. Alternatively, the humidity inside the scope assembly may be controlled (or regulated, e.g., manually or automatically) such that the inner humidity of the scope assembly is lower or higher than the ambient humidity. In some examples, the pressure, temperature, and/or humidity of the scope assembly may be regulated for optimal function of the scope assembly.

In some cases, the scope assembly of the present disclosure may be operatively coupled to an optical adapter.

The optical adapter of the present disclosure may allow visualization of structures or features (e.g., blood flow) that are beneath the surface of the target site, which structures or features would ordinarily be invisible to the human eye or other scope assemblies. The optical adapter of the present disclosure may make the invisible, visible. The optical adapter of the present disclosure may help visualize the invisible. The optical adapter, as a single setup with an existing scope assembly (e.g., an endoscope with an off-the-shelf camera), may enable a plurality of different imaging modalities. For example, the optical adapter may provide speckle imaging capabilities as well as photographic images and/or video in a single setup. In such case, the optical adapter may allow users to switch between different visualization modes, e.g., (i) white-light based video only, (ii) laser speckle imaging only, and (iii) both white-light based video and laser speckle imaging.

The optical adapter may be configured to be operatively coupled to an elongated scope and a third-party camera for medical imaging. The optical adapter may enhance one or more functions (e.g., imaging functions) of the elongated scope and the third part camera. The optical adapter may introduce one or more additional functions (e.g., imaging functions) to the elongated scope and the third part camera. The optical adapter may allow a user (e.g., a medical practitioner such as a physician, nurse practitioner, nurse, imaging specialist, etc.) to visualize and/or analyze a target site of a subject, such as internal tissue of a patient, in one or more ways that any traditional scope assembly alone cannot.

In some cases, the optical adapter may comprise a housing comprising (1) a first end configured to releasably couple to a scope and (2) a second end configured to releasably couple to a camera. The optical adapter may comprise an image sensor in the housing. The optical adapter may comprise an optics assembly disposed in the housing. The optics assembly is configured to (1) receive light signals that are reflected from a target site within a subject's body and transmitted through the scope, and (2) reflect a first portion of the light signals onto one of the image sensor or the camera, while permitting a second portion of the light signals to pass through to the other of the image sensor or the camera. In some cases, the image sensor may be a ToF sensor, as provided in the present disclosure.

In some cases, the scope assembly and the optical adapter may be operatively coupled to each other. The scope assembly and the optical adapter may be configured to transmit imaging data from each other.

Imaging Kit

Any subject scope assembly of the present disclosure can be incorporated as part of an imaging kit. In an aspect, the present disclosure provides an imaging kit comprising any of the subject scope assembly of the present disclosure and one or more illumination sources configured to transmit one or more light beams to and through the elongated scope. The kit may comprise at least 1, 2, 3, 4, 5, 6, 7, 8, 9, 10, or more illumination sources. The kit may comprise at most 10, 9, 8, 7, 6, 5, 4, 3, 2, or 1 illumination source. In some cases, a single illumination source may be configured to transmit at least 1, 2, 3, 4, 5, 6, 7, 8, 9, 10, or more light beams to the scope. The single illumination source may be configured to transmit at most 10, 9, 8, 7, 6, 5, 4, 3, 2, or 1 light beam to the scope. In some cases, a plurality of illumination sources may be configured to transmit at least 2, 3, 4, 5, 6, 7, 8, 9, 10, or more light beams to the scope. The plurality of illumination sources may be configured to transmit at most 10, 9, 8, 7, 6, 5, 4, 3, or 2 light beams to the scope. In an example, the illumination source may be configured to transmit a combined light beam to the elongated scope for directing at least a portion of the combined light beam onto a plurality of locations within the subject's body.

FIG. 1A schematically illustrates an example ecosystem for medical imaging. The ecosystem may comprise one or more target sites 2100 of a subject (e.g., one or more tissue sites of interest of a patient). The ecosystem may comprise a scope assembly 2200. The scope assembly 2200 may be operatively coupled to (or may enclose at least a portion of) an elongated scope 2300. The ecosystem may comprise an illumination source 2400 in optical communication with the elongated scope 2300. The illumination source 2400 may be configured to provide one or more light beams (e.g., a combined light beam) through the elongated scope 2300, through the scope assembly 2200, and toward the target site(s) 2100. The target site(s) 2100 may be in optical communication with the scope assembly 2200, such that (i) the target site(s) 2100 may be illuminated by the one or more light beams from the scope assembly 2200 and (ii) at least one sensor (e.g., a 2D camera or a depth sensor) of the scope assembly 2200 may detect one or more light signals reflected or emitted by the target site(s) 2100 upon such illumination. The scope assembly 2200 may be configured to capture at least one image or video of the target site based on at least a portion of the one or more light signals from the target site(s) 2100. The scope assembly 2200, the elongated scope 2300, and/or the illumination source 2400 may be operatively coupled to an imaging processor 2500. The imaging processor 2500 may be configured to regulate one or more processes of the medical imaging.

Figure 1B:
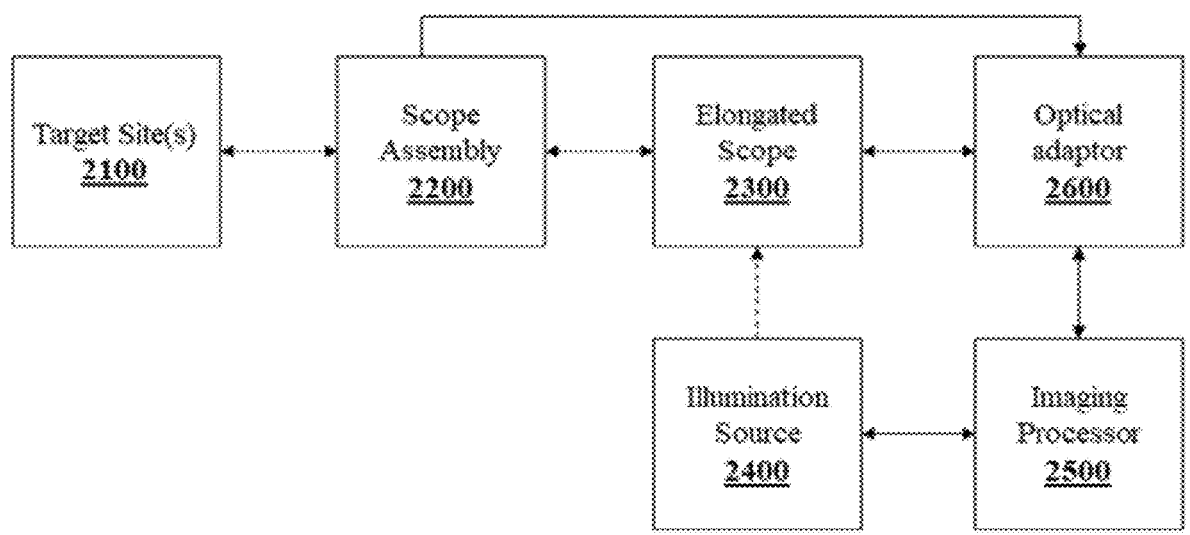

FIG. 1B schematically illustrates a different example ecosystem for medical imaging. The ecosystem of FIG. 1B may comprise the target site(s) 2100, the scope assembly 2200, the elongated scope 2300, the illumination source 2400, and the imaging processor 2500 as shown in FIG. 1A. Referring to FIG. 1B, the ecosystem may further comprise an optical adapter 2600 that is operatively coupled to one or more components of the scope assembly 2200. The optical adapter 2600 may be in optical communication with the scope assembly 2200 and the elongated scope 2300, such that the optical adapter 2600 may receive one or more light signals from the scope assembly 2200 and/or the elongated scope 2300. The optical adapter 2600 may be configured to generate data (e.g., images, videos, lase speckle imaging, etc.) based on the received one or more light signals. The imaging processor 2500 may be configured to analyze or combine data, image(s), or video(s) generated by the scope assembly 2200 and the optical adapter 2600.

Figure 1C:
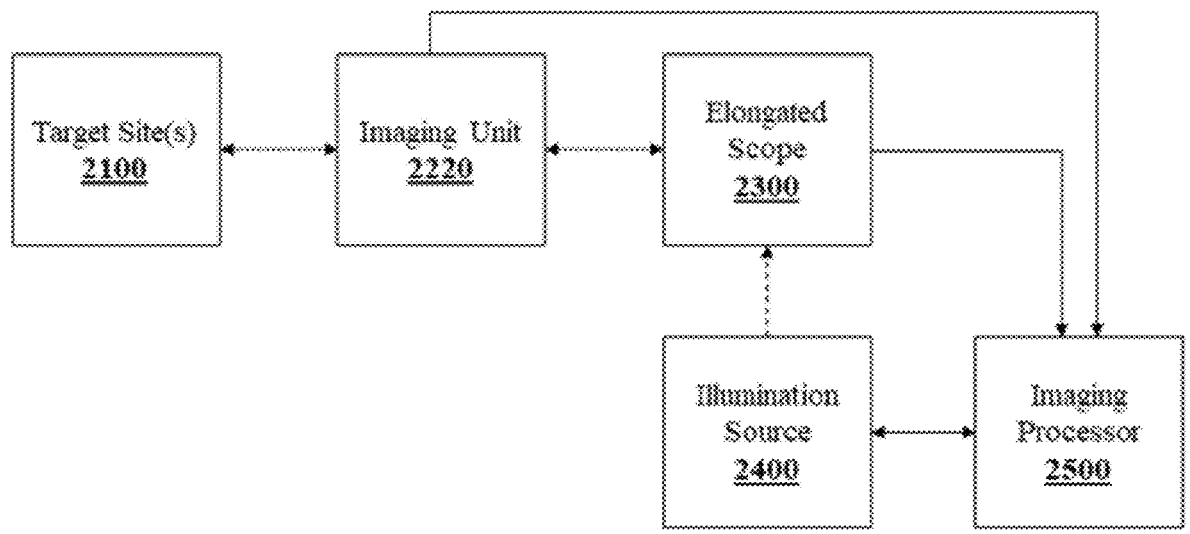

FIG. 1C schematically illustrates an example ecosystem for medical imaging. The ecosystem may comprise one or more target sites 2100 of a subject (e.g., one or more tissue sites of interest of a patient). The ecosystem may comprise a scope assembly. The scope assembly may comprise an imaging unit 2220 comprising one or more sensors (e.g., a camera, a depth sensor, or both) that is operatively coupled to (e.g., connected to) an elongated scope 2300. The ecosystem may comprise an illumination source 2400 in optical communication with the elongated scope 2300. The illumination source 2400 may be configured to provide one or more light beams (e.g., a combined light beam) through the elongated scope 2300, optionally through the imaging unit 2220, and toward the target site(s) 2100. The target site(s) 2100 may be in optical communication with the scope assembly, such that (i) the target site(s) 2100 may be illuminated by the one or more light beams from the scope assembly and (ii) at least one sensor (e.g., a 2D camera or a depth sensor) of the imaging unit 2220 may detect one or more light signals reflected or emitted by the target site(s) 2100 upon such illumination. The imaging unit 2220 may be configured to capture at least one image or video of the target site based on at least a portion of the one or more light signals from the target site(s) 2100. The imaging unit 2220, the elongated scope 2300, and/or the illumination source 2400 may be operatively coupled to an imaging processor 2500. The imaging processor 2500 may be configured to regulate one or more processes of the medical imaging.

Figure 1D:
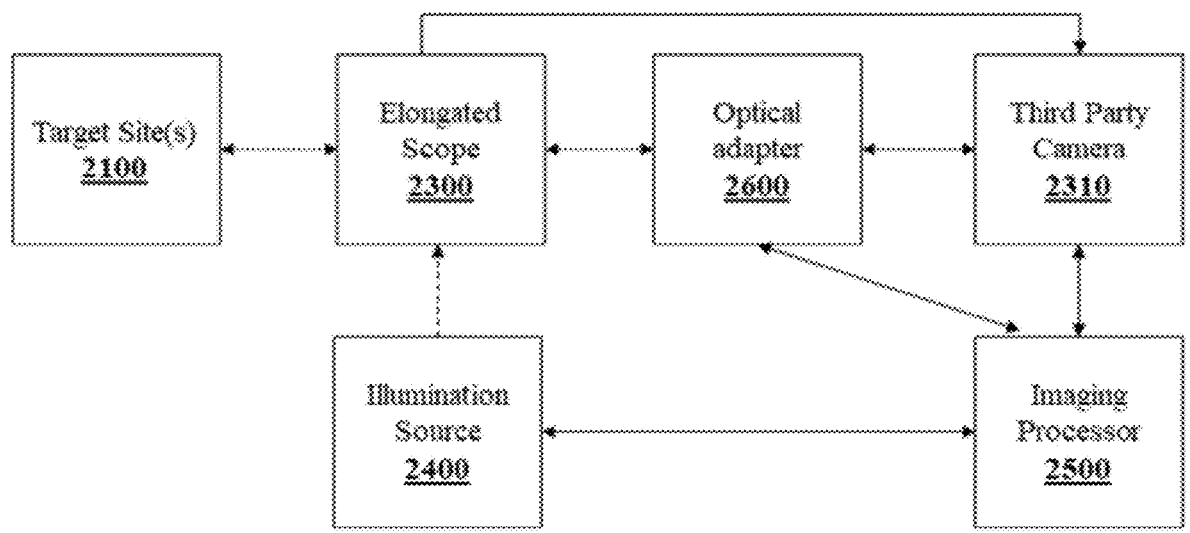

FIG. 1D schematically illustrates an example ecosystem for medical imaging. The ecosystem may comprise one or more target sites 2100 of a subject (e.g., one or more tissue sites of interest of a patient). The ecosystem may comprise an elongated scope 2300. The scope assembly may comprise an optical adapter 2600 comprising at least one sensor (e.g., a depth sensor). The optical adapter 2600 may be operatively coupled to (e.g., releasably coupled to) the elongated scope 2300. The ecosystem may comprise a third party camera 2310 (e.g., a two-dimensional camera) that is operatively coupled to (e.g., releasably coupled to) the optical adapter 2600. The ecosystem may comprise an illumination source 2400 in optical communication with the elongated scope 2300. The illumination source 2400 may be configured to provide one or more light beams (e.g., a combined light beam) through the elongated scope 2300 and toward the target site(s) 2100. The optical adapter 2600 may comprise an optics unit (e.g., one or more mirrors) configured to (1) receive light signals that are reflected from the target site 2100 and transmitted through the elongated scope 2300, and (2) reflect a first portion of the light signals onto one of the depth sensor of the optical adapter 2600 or the third party camera 2310, while permitting a second portion of the light signals to pass through to the other of the optical adapter 2600 or the third party camera 2310. The optical adapter 2600 (e.g., the depth sensor of the optical adapter 2600), the third party camera 2310, and/or the illumination source 2400 may be operatively coupled to an imaging processor 2500. The imaging processor 2500 may be configured to regulate one or more processes of the medical imaging.

Figure 2:
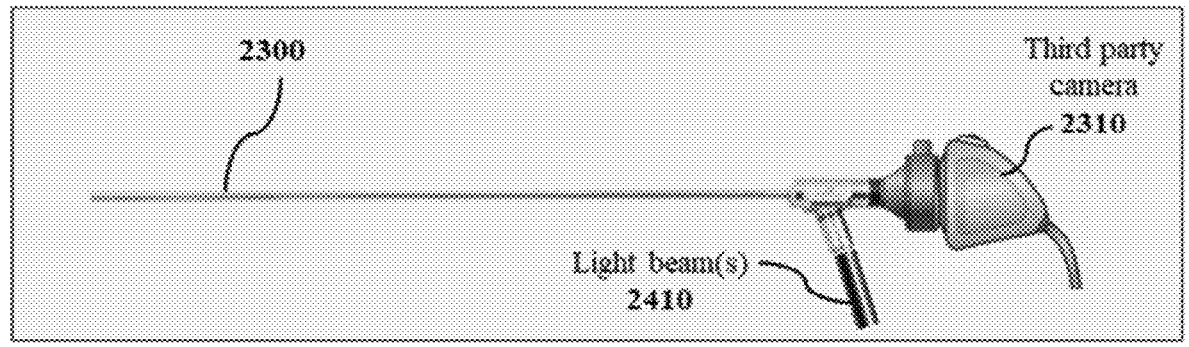
FIG. 2 schematically illustrates an elongated scope, in accordance with some embodiments.

FIG. 2 schematically illustrates an existing scope. The existing scope may comprise an elongated scope 2300 operatively coupled to a third party camera 2310. The elongated scope 2300 may receive one or more light beams 2410 from an illumination source 2400 and direct the light beam(s) 2410 towards a target site within a subject's body. Upon exposure to the light beam(s) 2410, the target site may reflect or emit a light signal, which light signal may be directed via the elongated scope 2300 towards the third party camera 2310. The third party camera 2310 may generate images or videos of the target site based on the received light signal.

Figure 3A:
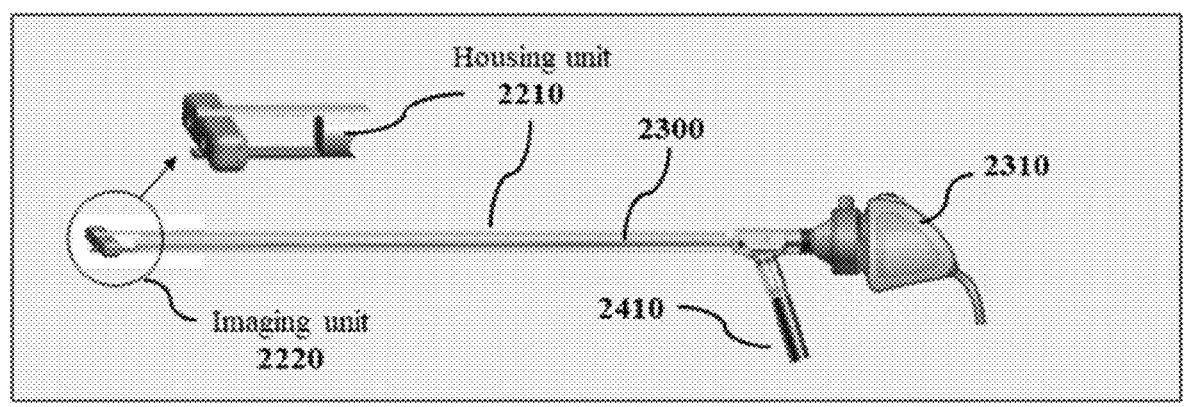
FIGS. 3A-3D schematically illustrate examples of a scope assembly operatively coupled to an elongated scope, in accordance with some embodiments.

FIG. 3A schematically illustrates an example of a scope assembly 2200 of the present disclosure. The scope assembly 2200 may be operatively coupled to an existing scope, e.g., the existing scope illustrated in FIG. 2. Referring to FIG. 3A, the scope assembly 2200 may comprise a housing unit 2210 configured to enclose (or releasably couple to) at least a portion of the elongated scope 2300. The scope assembly 2200 may comprise an imaging unit 2220, as described herein the present disclosure. For example, the imaging unit 2220 may be configured to move translationally and/or rotationally with respect to the housing unit 2210 to increase a field of view of the imaging unit 2220. In some cases, the imaging unit 2220 may comprise at least two separate sensors disposed on different sides of the imaging unit 2220. The imaging unit 2220 may comprise one or more openings to allow one or more light beams transmitted through the elongated scope 2300 through the imaging unit 2220 and to one or more locations within the subject's body.

Figure 3B:
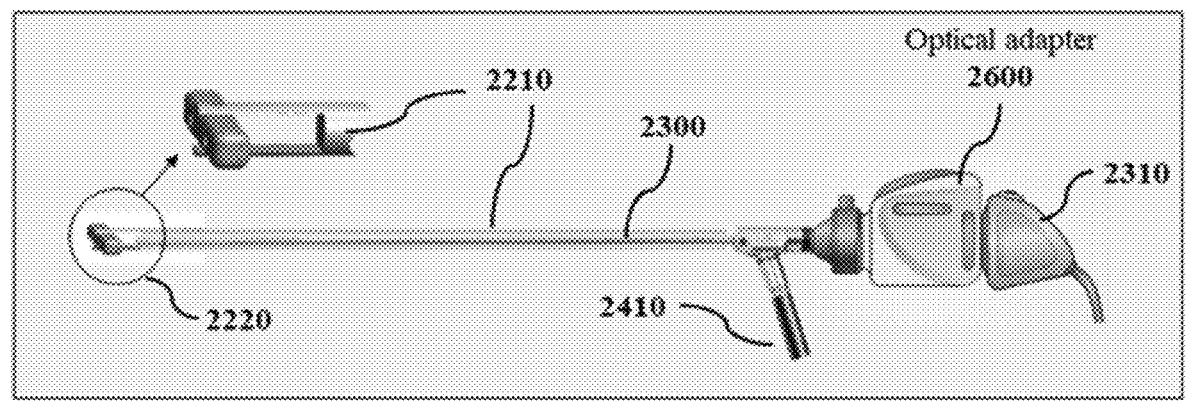

FIG. 3B schematically illustrates another example of a scope assembly 2200 of the present disclosure. The scope assembly 2200 may be operatively coupled to an existing scope, e.g., the existing scope illustrated in FIG. 2. Referring to FIG. 3B, the scope assembly 2200 may comprise a housing unit 2210 configured to enclose (or releasably couple to) at least a portion of the elongated scope 2300. The scope assembly 2200 may comprise an imaging unit 2220, as described herein the present disclosure. In some cases, the imaging unit 2220 may comprise at least two separate sensors disposed on different sides of the imaging unit 2220. In some cases, the elongated scope 2300 may be coupled to an optical adapter 2600. The optical adapter may be coupled to the third party camera 2310. The optical adapter 2600 may be configured to receive one or more light signals reflected or emitted by one or more locations within the subject's body (via the imaging unit 2220 and/or the elongated scope 2300). The optical adapter 2600 may direct a first portion of the received light signal(s) towards a sensor within the optical adapter 2600, and direct a second portion of the received light signal(s) towards the third party camera 2310.

Figure 3C:
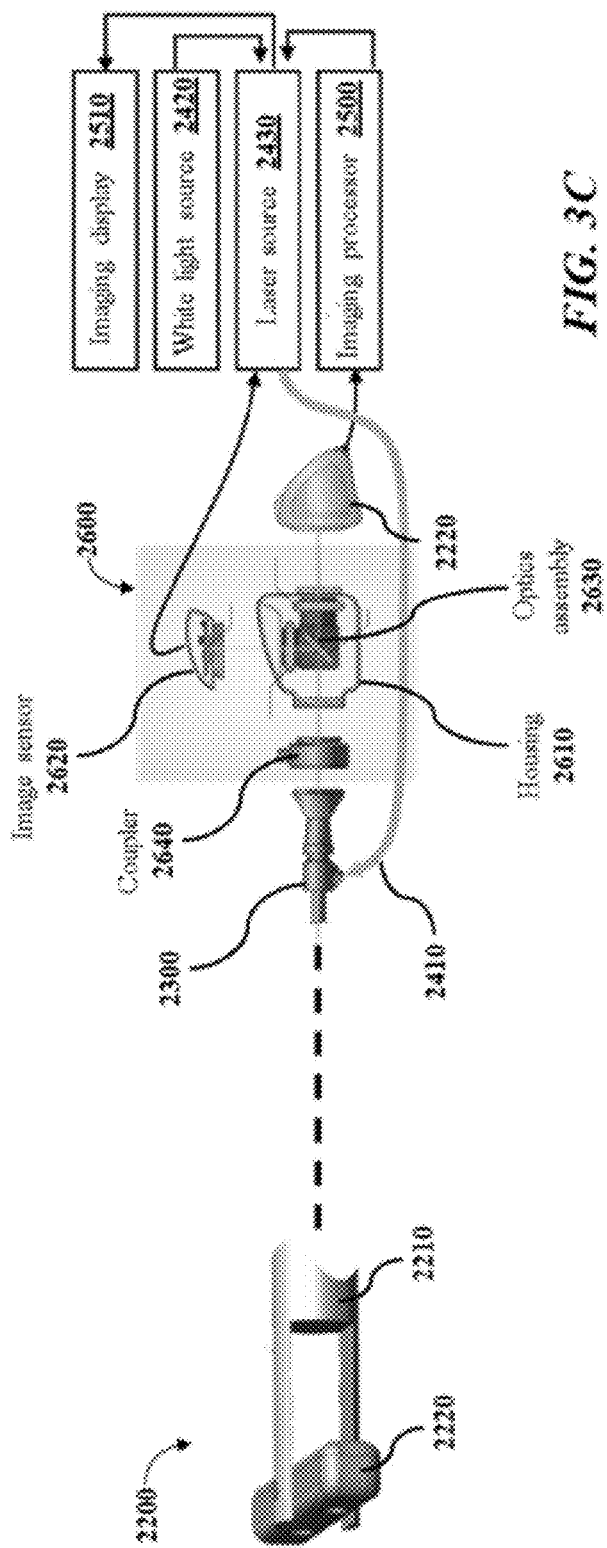

FIG. 3C schematically illustrates an embodiment of the medical imaging ecosystem illustrated in FIG. 3B. Referring to FIG. 3C, a white light source 2420 and a laser source 2430 may be operatively (e.g., optically) in communication with each other. The laser light source 2430 may combine the white light and one or more laser wavelengths beams into a combine light beam 2410, and direct the combined light beam 2410 towards the elongated scope 2300. The combined light beam 2410 may be directed towards the imaging unit 2220 of the scope assembly 2200 to visualize one or more locations within the subject's body. One or more sensors of the imaging unit 2220 (e.g., 2D camera, depth sensor) may receive light signals reflected or emitted by the one or more locations, and transmit such imaging data (e.g., wirelessly) to the imaging processor 2500. Additionally, at least a portion of the light signals from the one or more locations may be transmitted via the elongated scope 2300 and towards the optical adapter 2600. The optical adapter 2600 may be coupled to the elongated scope 2300 via a coupler 2640. The optical adapter 2600 may comprise an optics assembly 2630 within a housing 2610. The optics assembly 2630 may direct a portion of a received light signal towards an image sensor 2620. The image sensor (e.g., depth sensor) may then generate an imaging data and transmit such imaging data to the laser source 2430. The optics assembly 2630 may direct a different portion of the received light signal towards the third party camera (e.g., a 2D camera) 2220. The camera 2220 may then generate an imaging data and transmit such imaging data to the imaging processor 2500. The laser source 2430 and the imaging processor 2500 may be operatively coupled to each other to analyze and/or combine the plurality of imaging data. Any analysis (e.g., images, videos, 3D reconstructions) may be displayed on the imaging display 2510, e.g., in real time during the medical imaging procedure.

Figure 3D:
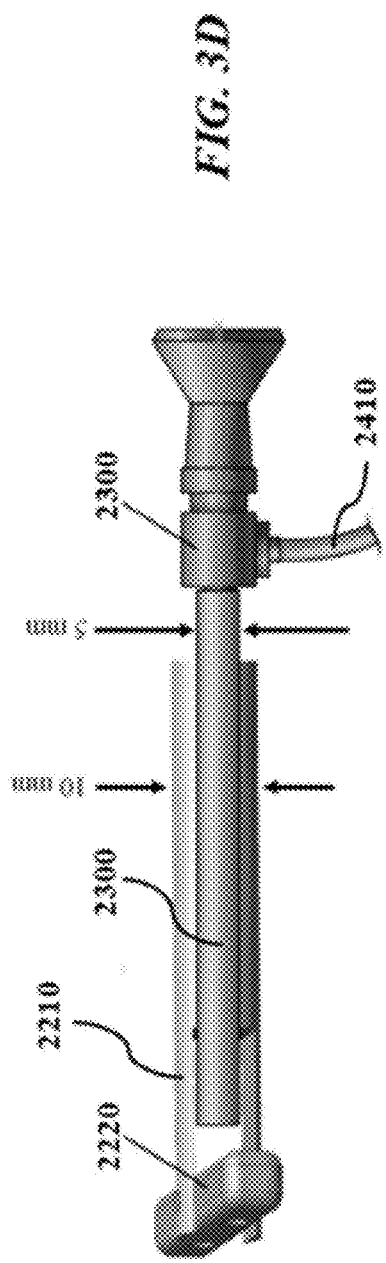

FIG. 3D schematically illustrates an example configuration of the scope assembly 2200 with respect to the elongated scope 2300. The housing unit 2210 of the scope assembly 2200 may enclose at least a portion of a distal end of the elongated scope 2300. The imaging unit 2220 of the scope assembly 2200 may be configured to translate and/or rotate with respect to the housing unit 2210 without touching any portion of the elongated scope 2300. In an example, a cross-sectional dimension of the elongated scope 2300 may be about 5 mm. As such, a cross-sectional dimension of the housing unit 2210 may be greater than about 5 mm, e.g., about 10 mm, to be capable of enclosing the distal end of the elongated scope 2300. An inner surface of the housing unit 2210 and an outer surface of the elongated scope 2300 may be in contact with one another. In other embodiments, the inner surface of the housing unit 2210 and the outer surface of the elongated scope 2300 may not or need not be in contact with one another.

FIG. 4A schematically illustrates an example of the scope assembly of the present disclosure. A distal end of the imaging unit of the scope assembly is illustrated in FIG. 4A. The distal end of the imaging unit may comprise a camera and separately a depth sensor (e.g., a stereo sensor). The camera may comprise a first lens, and the depth sensor may comprise a plurality of lenses (e.g., a left lens and a right lens) that are different from the first lens of the camera. The lenses of the camera and the depth sensor may be disposed on a same side of the imaging unit, as shown in FIG. 4A. In other embodiments, the first lens of the camera may be disposed on a different side than the plurality of lenses of the depth sensor. In some cases, a distance between the left and right lenses of the depth sensor may be indicative of a measurable depth between the depth sensor and the location within the subject's body.

Figure 4E:
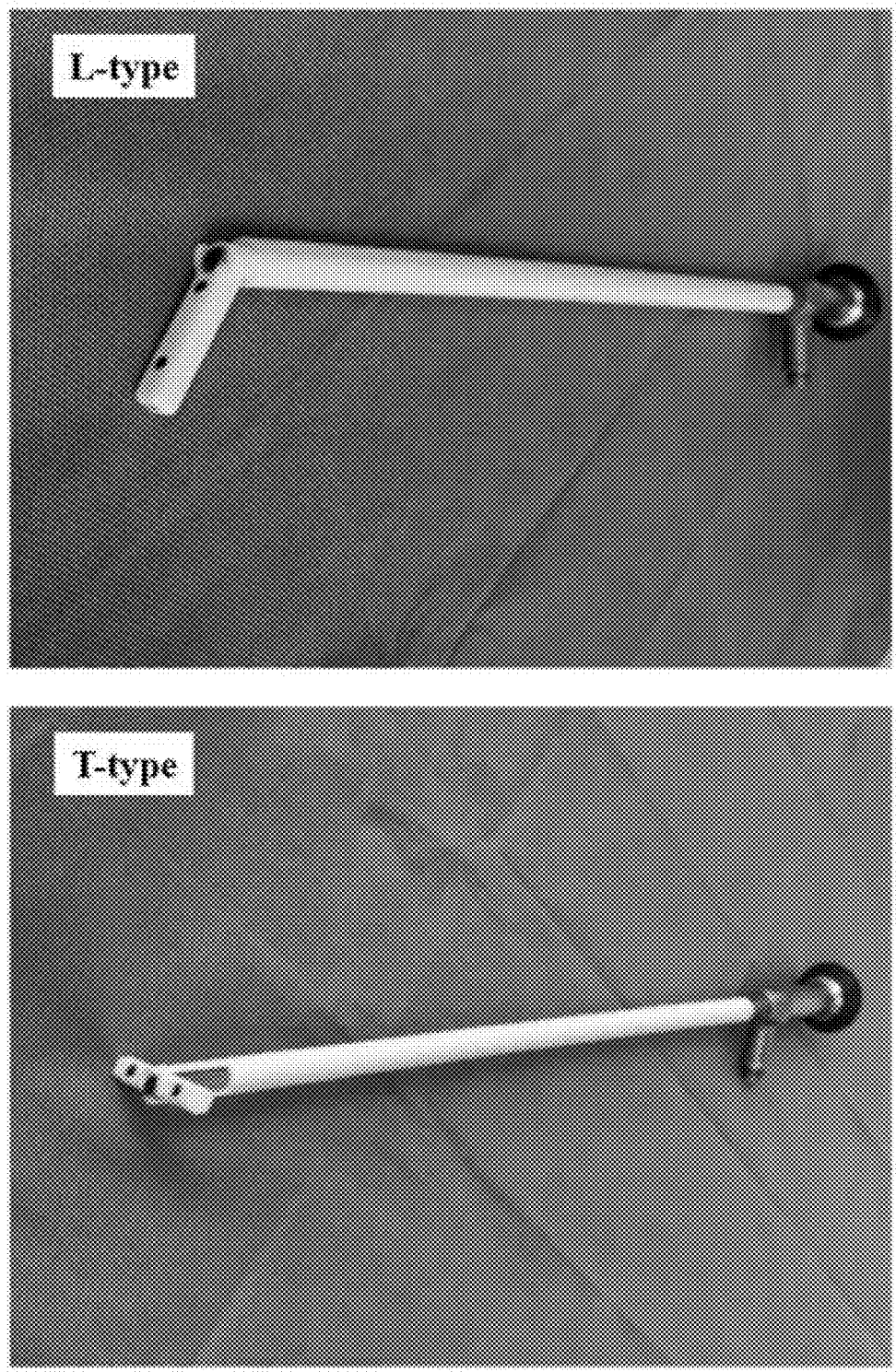

FIGS. 4B-4F schematically illustrate different examples of the scope assembly of the present disclosure. Referring to FIG. 4B, the scope assembly may comprise a housing unit, which may be a reusable slip-over sleeve to enclose a distal end of an elongated scope. The scope assembly may further comprise an imaging unit, which may be a disposable articulated tip. The imaging unit may comprise a forward facing 2D camera at a distal end for navigating through the subject's body to find a target site. The imaging unit may comprise a depth sensor (e.g., a stereo camera or a ToF camera) to provide depth perception imaging of the target site. Optionally, perfusion data of a target site within the subject's body may be used for the depth perception. The imaging unit may be articulated with respect to the housing unit. As shown in FIG. 4C, the imaging unit may further comprise one or more motion sensors (e.g., an IMU) configure to sense position, orientation, and/or sudden accelerations of the imaging unit during the medical imaging. As shown in FIGS. 4B-4C, the forward facing 2D camera and the depth sensor may be substantially orthogonal to each other.

Referring to FIG. 4D, the imaging unit of the scope assembly may be disposed in different configurations with respect to the housing unit of the scope assembly. In an example, the imaging unit may be coupled to the housing unit via an L-type junction, wherein an end of the imaging unit is coupled to the housing unit and configured to move transitionally and/or rotationally. In another example, the imaging unit may be coupled to the housing unit via a T-type junction, wherein a middle portion of the imaging unit is coupled to the housing unit and configured to move transitionally and/or rotationally. Example models of the L-type imaging unit and the T-type imaging unit is shown in FIG. 4E. As depicted in FIG. 4E, a distal end of the elongated scope can be optically exposed through at least a portion of the imaging unit (e.g., L-type or T-type), such that the distal end of the elongated scope is optically in communication with a target site within a subject's body. When in such optical communication, the distal end of the elongated scope may be configured to direct one or more light beams directly to the target site. To achieve this, at least a portion of the imaging unit may comprise (i) an opening or (ii) a transparent or semi-transparent window to optically expose the distal end of the elongated scope.

Figure 4F:
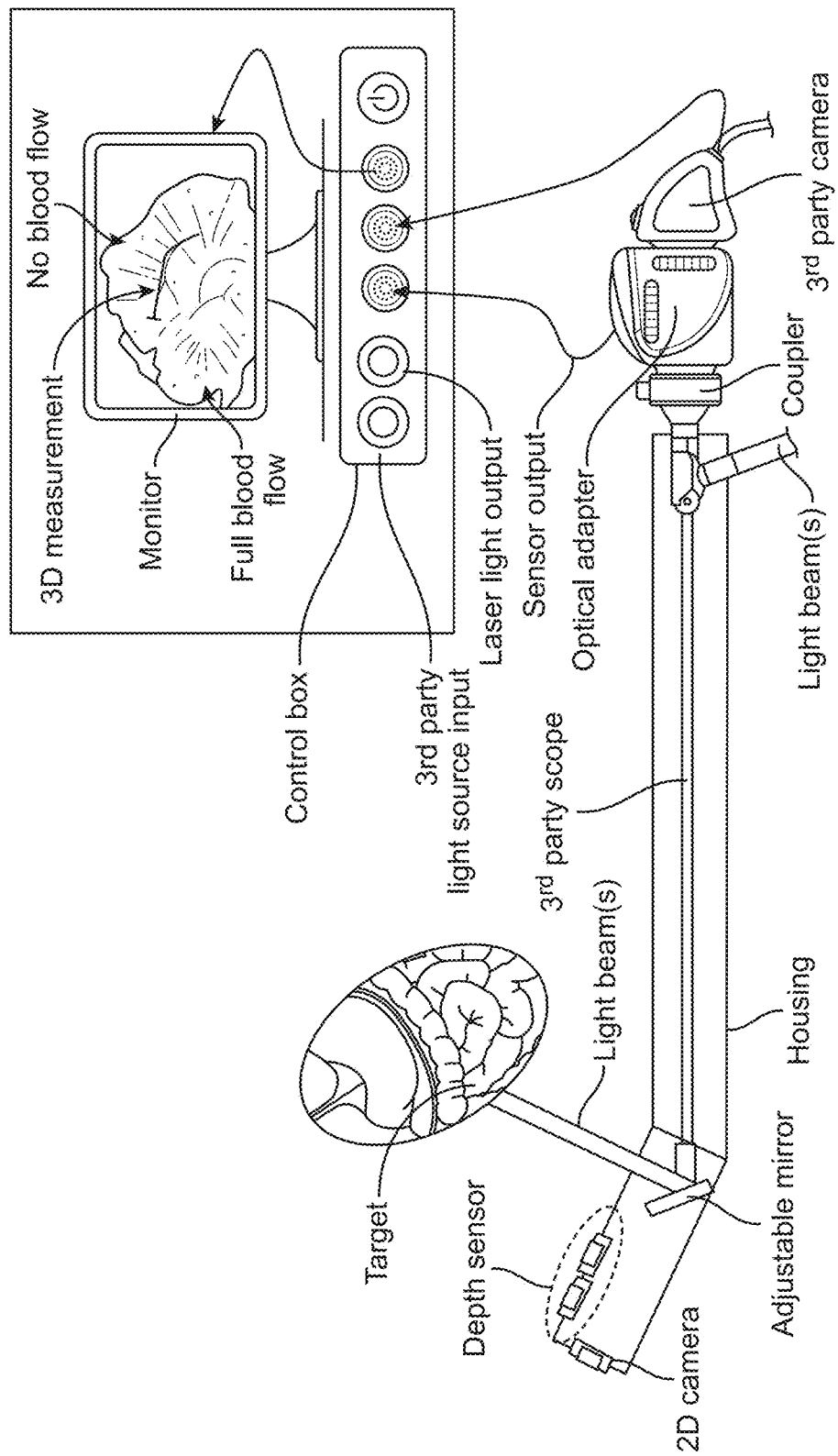

FIG. 4F schematically illustrates a detailed schematic of the scope assembly that is operatively coupled to an elongated scope. A control box may be configured to receive a white light from a third party light source, one or more laser beams from a laser light source, a third party camera signal, and imaging data from one or more sensors of the imaging unit of the scope assembly. The control box may be configured to deliver (e.g., by directing one or more optical sources) a combined light of the white light and one or more laser beams to the third party scope (e.g., an elongated scope). After imaging, the control box (e.g., comprising a processor) and a monitor may display depth (and optionally perfusion) imaging of a target site within the subject's body based on at least the imaging data from the depth sensor of the imaging unit of the scope assembly. The imaging unit may provide a side facing depth perception of a target site (and optionally perfusion within the target site) using a chip-on-tip stereo camera (or a ToF sensor) and by projecting one or more light beams (e.g., laser light beams) to the target site. In an example, the one or more light beams may comprise 5 laser wavelengths and a standard laparoscopic white light. The imaging unit may also utilize a forward facing 2D camera, disposed substantially orthogonal to the stereo camera. The forward facing 2D camera may facilitate the insertion of the scope assembly into the subject's body and navigating within the subject's body, while the side-view stereo camera may function as a primary vision system with a wider field of view as the imaging unit is articulated in one or more degrees of freedom. As an angle of the imaging unit (or distal head of the scope assembly) is changed, an adjustable mirror within the imaging unit may be adjusted accordingly to ensure that the re-directed light beam(s) (e.g., the laser beam(s)) remain at a proper angle relative to the optical axis of the stereo camera (e.g., substantially parallel to the optical axis of the stereo camera). Any imaging data generated by the 2D camera of the depth sensor of the imaging unit may be transmitted (e.g., wirelessly) to the control box for image processing and analysis.

Figure 5:
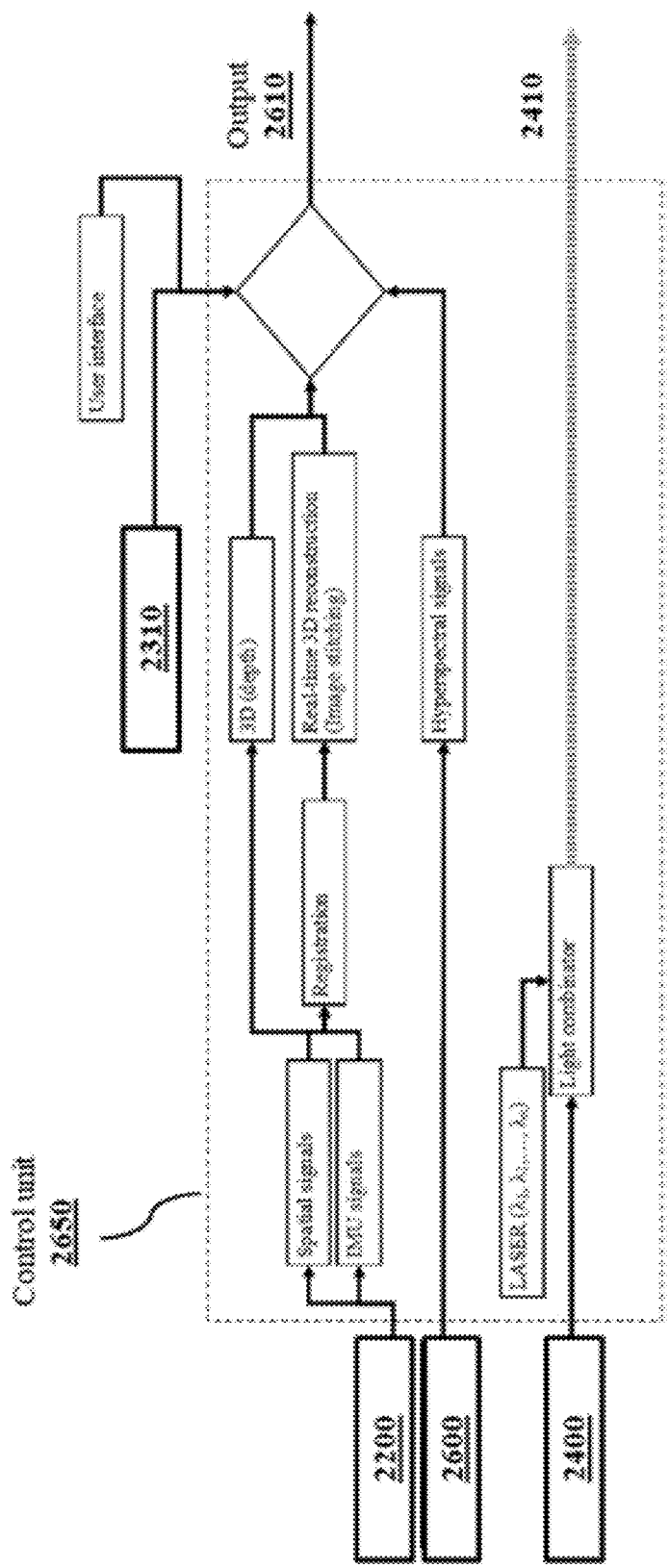
FIG. 5 schematically illustrates a control unit for a scope assembly, in accordance with some embodiments.

FIG. 5 schematically illustrates a control unit for a scope assembly. The scope assembly 2200 may generate one or more spatial signals from one or more sensors, such as a depth sensor. The scope assembly 2200 may further generate one or more IMU signals from one or more motion sensors. The spatial signals may be used to provide 3D imaging comprising depth perception. The spatial signals may be combined with the IMU signals (registered) for real-time 3D reconstruction of the target site within the subject's body. Image or video stitching may be used for the real-time 3D reconstruction. The 3D imaging, the 3D reconstruction, or any 2D images/videos from a third party camera 2310 may be transmitted as an output 2610, e.g., to be displayed on a monitor or stored in a database in communication with the control unit of the scope assembly. In addition, the scope assembly may be operatively coupled to an optical adapter that is disposed in between the elongated scope and the third party camera 2310. The optical adapter may comprise yet another sensor to detect at least a portion of a light signal that is reflected or emitted by the target site (e.g., hyperspectral signals) to generate imaging data indicative of one or more anatomical structures of the target site in real-time and without the use of dyes. Such imaging data may also be a part of the output 2610. The control unit 2650 may also be operatively coupled to the illumination source 2400 to direct a combined light (e.g., a white light and one or more laser wavelengths) 2410 towards the elongated scope.

Figure 6A:
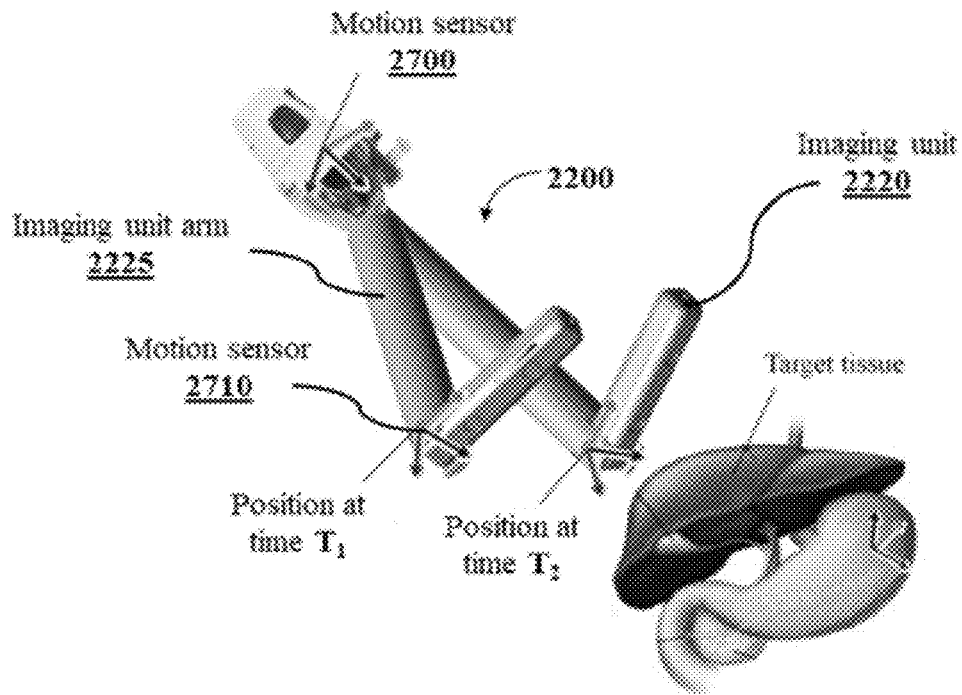
FIGS. 6A-6B schematically illustrate an example of a scope assembly comprising a motion sensor.
Figure 6B:
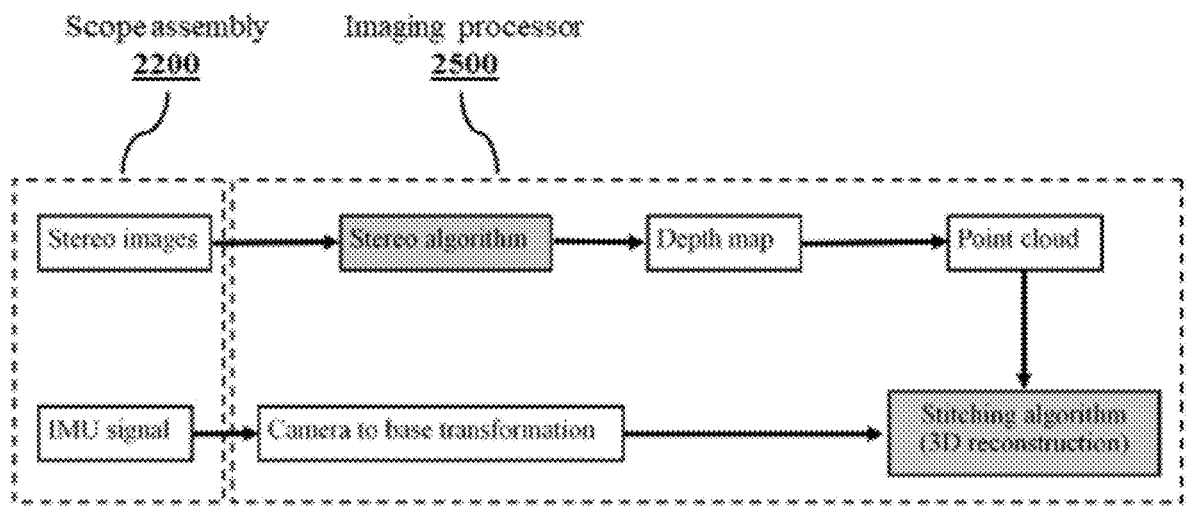

FIGS. 6A-6B schematically illustrate an example of a scope assembly comprising a motion sensor. One or more motion sensors of the scope assembly may allow real-time registration and stitching of a plurality of images (e.g., 2D or 3D images) to reconstruct a 3D view of the target site. The plurality of images in camera space may be registered in base space (e.g., space with respect to the subject's body) using the one or more motion sensors. Referring to FIG. 6A, the scope assembly may comprise a first motion sensor 2700 (e.g., IMU) at a first hinge of the imaging unit arm 2225. The first hinge may allow movement of the imaging unit arm 2225 in 3 degrees of freedom, and the first motion sensor 2700 may detect and record position, orientation, and/or sudden acceleration of the imaging unit arm 2225. The scope assembly may further comprise a second motion sensor 2710 (e.g., IMU) at a second hinge of the imaging unit 2220. The second hinge may allow movement of the imaging unit 2220 in 3 degrees of freedom, and the second motion sensor 2710 may detect and record position, orientation, and/or sudden acceleration of the imaging unit 2220.

Referring to FIG. 6B, the scope assembly 2200 may generate a plurality of stereo images (e.g., by using a depth sensor, such as a stereo camera or a ToF sensor) and a plurality of IMU signals indicative of movements of one or more portions of the scope assembly (e.g., movements of the imaging unit). The imaging processor 2500 may use one or more stereo algorithms (e.g., using one or more machine learning algorithms) to generate a depth map of the target site within the subject's body based on the plurality of stereo images. Each depth map may be a point cloud (e.g., a set of data points in space). The imaging processor 2500 may use the plurality of IMU signals to transform the plurality of images in camera space to base space, thus allowing stitching of the depth map for 3D reconstruction. One or more stitching algorithms (e.g., using more or more machine learning algorithms) may be used for the 3D reconstruction.

Figure 7A:
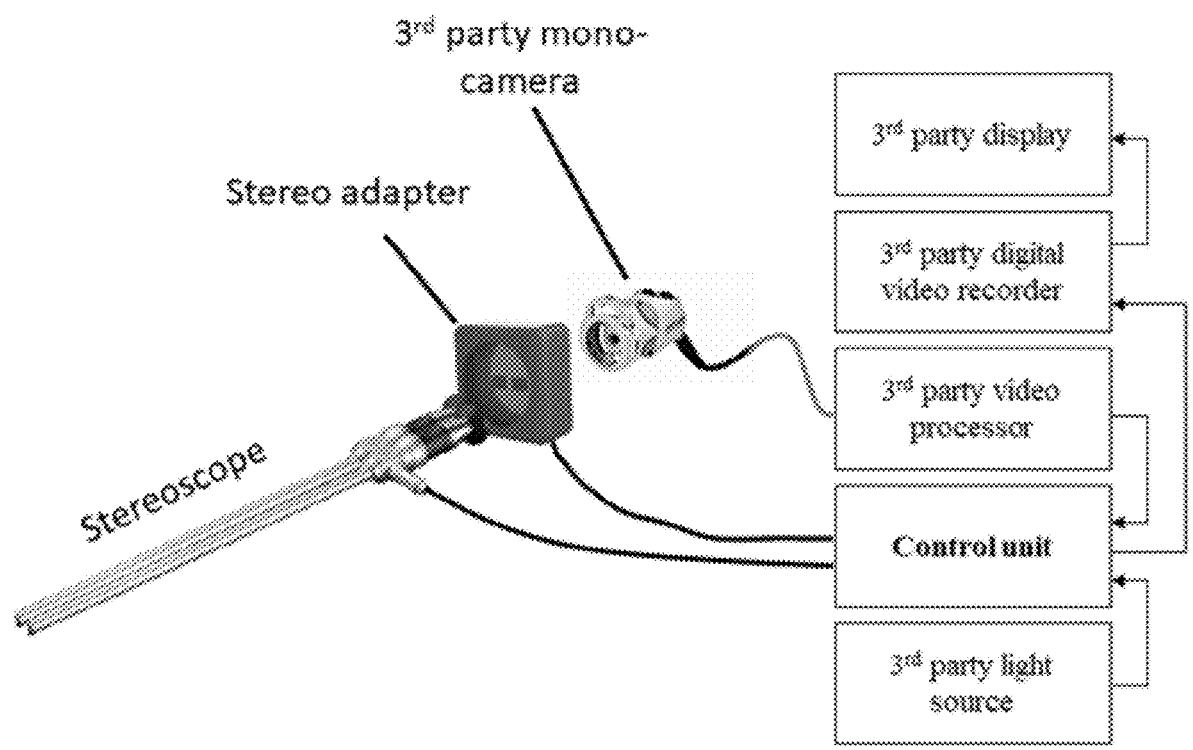
FIGS. 7A-7D schematically illustrate example imaging systems for depth sensing, in accordance with some embodiments.

FIGS. 7A-7D schematically illustrate example imaging systems for depth sensing. FIG. 7A schematically illustrates an example of a stereoscope adapter. The stereo adapter may be configured to be coupled in between a third party stereoscope and a third party camera (e.g., a 2D mono-camera). The stereo adapter may comprise one or more sensors to (i) receive at least a portion of light signals reflected (or emitted) by a target site within the subject's body and transmitted via the stereoscope and (ii) generate imaging data including depth imaging and perfusion imaging. The control unit may direct one or more light beams to the stereoscope to expose the target site to the one or more light beams. The third party camera may be configured to receive a different portion of the light signals to generate, for example, a color video. The control unit may be configured to overlay the color video and the imaging data from the sensor(s) of the stereo adapter to calibrate the stereo adapter prior to, concurrently with, or subsequent to the medical imaging procedure. The stereoscope adapter may not or need not contact the patient. The stereoscope adapter may induce minimal disruption of any existing operation room equipment. However, in some cases, the stereoscope adapter may be difficult to align, and require an existing stereoscope.

Figure 7B:
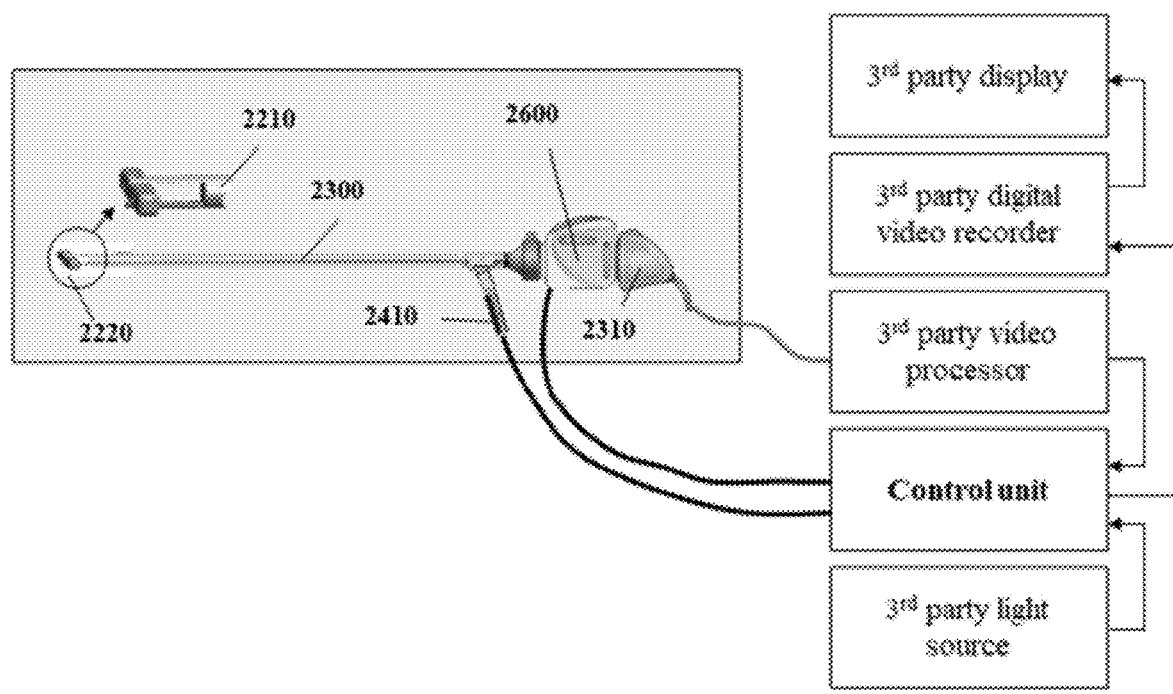

Referring to FIG. 7B, the housing unit 2210 of the scope assembly 2200 may be a deployable, non-articulating sleeve configured to fit over (or enclose) a 5 mm thick elongated scope 2300. The outer diameter of the housing unit 2210 of the scope assembly 2200 may be 10 mm, which may be within an acceptable size range for endoscope procedures. One or more sensors on the top and/or sides of the distal end (e.g., the articulating imaging unit 2220) of the scope assembly 2200 may collect depth and/or perfusion data of a target site within the subject's body. The one or more sensors may comprise a stereo sensor or a ToF sensor. Separately, color images and/or videos of the target site may be collected by a third party camera 2310. The control unit may be configured to overlay the color images/videos and the imaging data from the sensor(s) of the scope assembly 2200 to calibrate the scope assembly 2200 prior to, concurrently with, or subsequent to the medical imaging procedure. In some cases, the scope assembly may collect higher resolution depth imaging than the stereoscope adapter as provided in the present disclosure. The scope assembly may be compatible with one or more existing elongated scopes (e.g., existing laparoscopes). However, in some cases, the scope assembly may come in contact with the subject's body, and may require pre-procedure calibration. Additionally, the scope assembly may require a different workflow and an additional equipment set up to any existing elongated scopes.

Figure 7C:
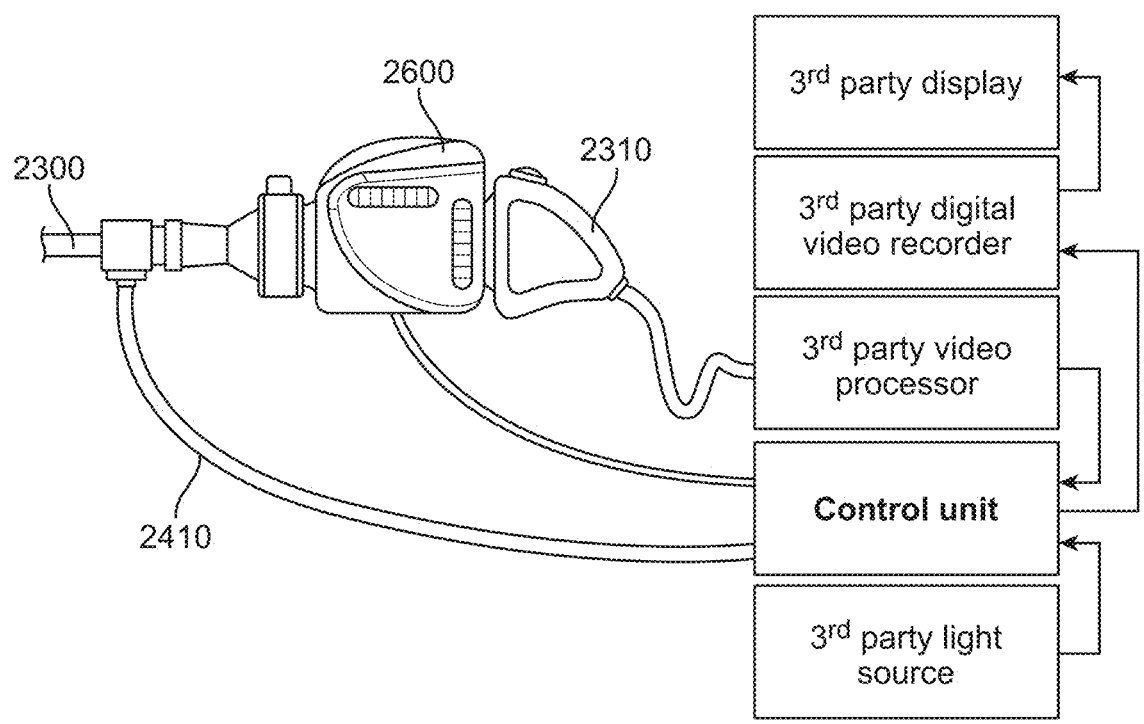

Referring to FIG. 7C, the optical adapter 2600 may comprise a ToF sensor to collect depth and/or perfusion data of the target site within the subject's body. The control unit may direct one or more optical sources to direct at least a ToF light (e.g., strobed amplitude modulated ToF light) through the elongated scope and to the target site. Any light signals reflected and emitted by the target site may be re-directed by the elongated scope to the optical adapter 2600. The ToF sensor in the optical adapter 2600 may collect depth data of the target site based on at least a portion of the re-directed light. The ToF sensor or a different sensor of the optical adapter 2600 may collect perfusion data of the target site based on the at least the portion of the re-directed light. Furthermore, color image and/or video of the target site may be collected by a third party camera 2310 based on a different portion of the re-directed light. The control unit may be configured to overlay the color images/videos and the imaging data (depth data and/or perfusion data) from the sensor(s) of the optical adapter 2600 to calibrate the optical adapter 2600 prior to, concurrently with, or subsequent to the medical imaging procedure. The optical adapter may not or need not contact the patient. The optical adapter may be compatible with one or more existing elongated scopes (e.g., existing laparoscopes). The optical adapter may not or need not require any different workflow than existing elongated scopes.

Figure 7D:
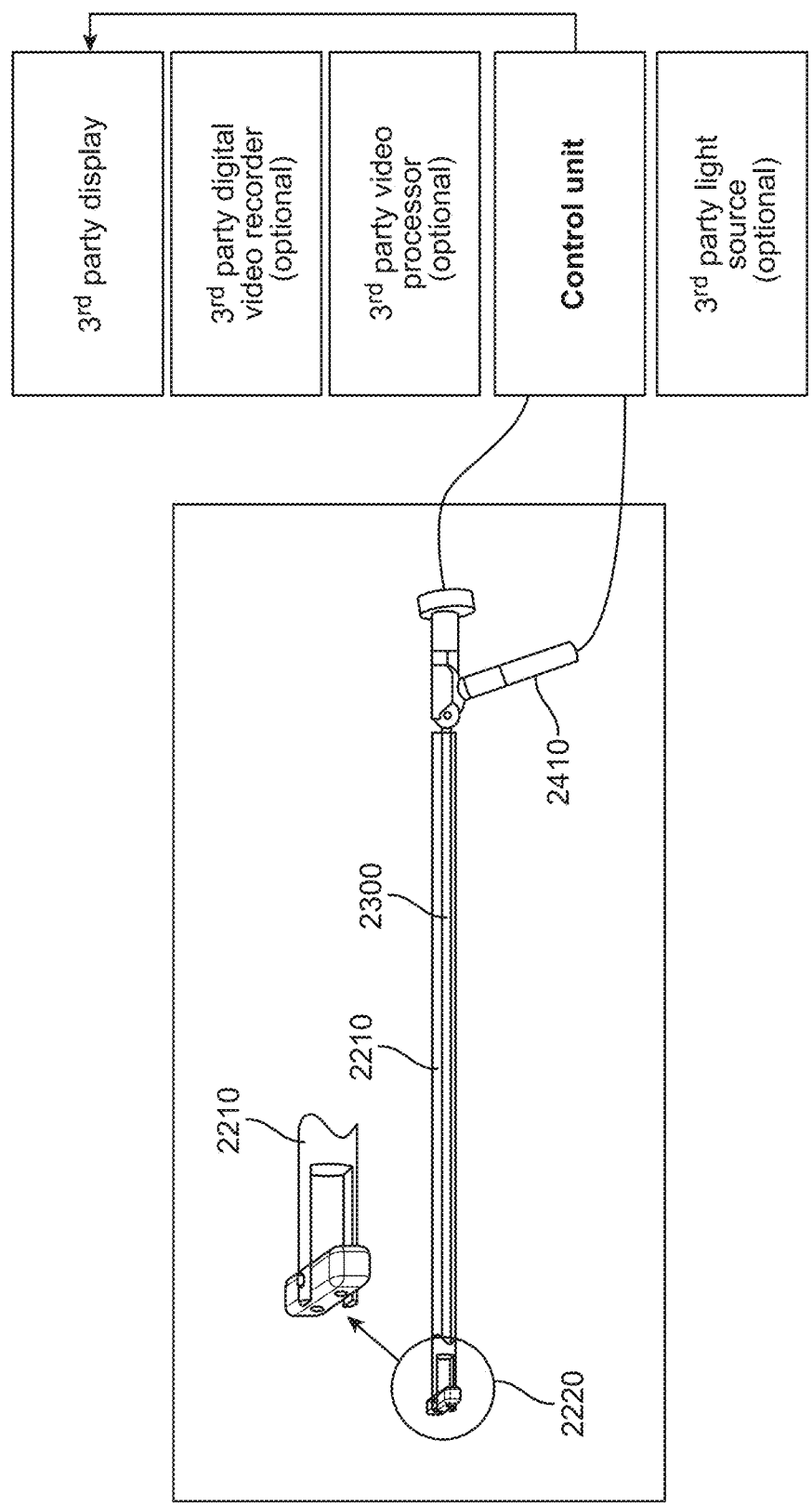

Referring to FIG. 7D, the housing unit 2210 of the scope assembly 2200 may be a deployable, non-articulating sleeve configured to fit over (or enclose) an elongated scope 2300. One or more sensors on the top and/or sides of the distal end (e.g., the articulating imaging unit 2220) of the scope assembly 2200 may collect depth and/or perfusion data of a target site within the subject's body. The one or more sensors may comprise a stereo sensor or a ToF sensor. The one or more sensors may further comprise a 2D sensor. The medical imaging system shown in FIG. 7D may not or need not require a third party camera. Instead, the sensor(s) on the scope assembly 2200 may collect color data in addition to depth and/or perfusion data. Thus, in contrast to other imaging systems illustrated in FIGS. 7A-7C, the medical imaging system illustrated in FIG. 7D may not or need not require the third party digital image/video recorder, a third party digital image/video processor, and a third party light source (for white light). Instead the control unit may direct a plurality of light beams (e.g., laser light beams) to the elongated scope 2300. The control unit may also be configured to receive imaging data collected by the scope assembly 2200 for analysis and display of the results on a third part display.

Methods of Use of Scope Assembly

Any subject scope assembly of the present disclosure can be used for medical imaging of a target site of a subject. In an aspect, the present disclosure provides a method of using a scope assembly for medical imaging. FIG. 8 shows an example flow chart of the method of using the scope assembly for medical imaging. The method may comprise providing a scope assembly comprising (i) a housing unit configured to enclose at least a portion of an elongated scope, and (ii) an imaging unit operably coupled to the housing unit, wherein the imaging unit comprises an optics assembly (process 2810). The method may further comprise receiving, by the optics assembly, one or more light beams that are transmitted through the elongated scope, and using the optics assembly to direct at least a portion of the one or more light beams onto two or more locations within a subject's body, wherein at least one of the two or more locations comprises a target site (process 2820). The method may further comprise moving the imaging unit via a rotational and/or translational motion relative to the housing unit to alter a field of view when imaging within the subject's body (process 2830).

FIG. 9 shows an additional example flow chart of the method of using the scope assembly for medical imaging. The method may comprise providing a scope assembly comprising (i) a housing unit configured to enclose at least a portion of an elongated scope, and (ii) an imaging unit operably coupled to the housing unit, wherein the imaging unit comprises an optics assembly (process 2910). The method may further comprise receiving, by the optics assembly, one or more light beams that are transmitted through the elongated scope, and using the optics assembly to direct (1) a first portion of the one or more light beams onto a target site within a subject's body and (2) a second portion of the one or more light beams onto another site within the subject's body (process 2920). The method may further comprise, with aid of at least one depth sensor, receiving a first light signal that is reflected from the target site and generating a first set of imaging data comprising depth maps (process 2930). The method may further comprise, with aid of at least one depth sensor, receiving a second light signal that is reflected from the another site and generating a second set of imaging data comprising 2D photographic or video images (process 2940).

Any one of the subject scope assembly of the present disclosure can be used to image, measure, and/or analyze depth of the target site within the subject's body. Examples of the depth sensing applications of the scope assembly disclosed herein may include, but are not limited to, depth scale, 3D measurement, 3D overlay (e.g., depth and laser speckle information), 3D reconstruction, indication or suggestion of what has been imaged vs. what has not been imaged, mini-map features to give an operator of the scope assembly a sense of direction when viewing (e.g., zoomed into) a particular feature, switching between a first-person and a third-person point of view, etc.

Any one of the subject scope assembly of the present disclosure can be used to visualize anatomy, morphology, one or more physiological features, and/or one or more pathological features of a target site within a subject's body. Examples of the physiological and/or pathological feature(s) can include, but are not limited to oxygenation, deoxygenation, artery-vein (A-V) classification, flow rate and/or flow volume of a body fluid (e.g., blood, lymph, tissue fluid, milk, saliva, semen, bile, etc.) such as blood perfusion or infarction, angiogenesis, cell density, inflammation, tissue swelling (e.g., brain swelling), tissue death, tissue dimension (e.g., diameter, area, volume), viral infection, bacterial infection, tumor dimension (e.g., diameter, area, volume), tumor margin after a tumor dissection, metastatic growth, etc.

Examples of the target site within the subject's body can include, but are not limited to, thyroid gland, adrenal gland, mammary gland, prostate gland, testicle, trachea, superior vena cava, interior vena cava, lung, liver, gallbladder, kidney, ureter, appendix, bladder, urethra, heart, esophagus, diaphragm, aorta, spleen, stomach, pancreas, small intestine, large intestine, rectum, vagina, ovary, bone, thymus, skin, adipose, eye, brain, fetus, arteries, veins, nerves, ureter, bile duct, healthy tissue, and diseased tissue.

In some cases, a diseased tissue may be affected by a tumor or cancer selected from the group consisting of. Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof.

Time of Flight

In another aspect, the present disclosure provides a system for medical imaging. The system may comprise a TOF adapter unit configured for time of flight (TOF) imaging. The TOF adapter unit may comprise a TOF depth sensor and/or a TOF imaging unit. In some cases, the TOF adapter unit may be operatively coupled to a TOF depth sensor and/or a TOF imaging unit that is located remote from the TOF adapter unit. The TOF adapter unit, the TOF depth sensor, and/or the TOF imaging unit may be used in combination with any of the medical imaging systems and methods disclosed herein. The TOF adapter unit, the TOF depth sensor, and/or the TOF imaging unit may be compatible with any of the chip-on-tip TOF systems described above.

The TOF depth sensor may comprise a depth sensor as described elsewhere herein. The depth sensor may be configured to obtain one or more TOF measurements based on an amount of time it takes for TOF light to travel from a first location to a second location. In some cases, the first location may correspond to a location of a TOF light source or a location within the surgical scene. In some cases, the second location may correspond to a location of the TOF depth sensor or a tip of the scope. In any of the embodiments described herein, the first location and/or the second location may correspond to any one or more arbitrary locations in real space that lie along an optical pathway of the TOF light. The optical pathway of the TOF light may correspond to a distance and a direction in which the TOF light travels after being transmitted by the TOF light source and before being received or detected by the TOF depth sensor. In some cases, the one or more TOF measurements may be derived based on an amount of time it takes for TOF light to travel between a plurality of locations in real space. The plurality of locations may comprise three or more locations in real space that lie along an optical pathway of the TOF light. In some cases, the TOF measurements may be derived in part based on a phase shift that is observed between the TOF light directed to the target region and the TOF light reflected from the target region.

The TOF imaging unit may comprise an imaging device or an imaging sensor configured to generate one or more depth maps or depth images of a target region or a surgical scene, using TOF light transmitted through the scope.

The TOF adapter unit may be positioned between a scope and at least one imaging device that is configured to generate one or more medical images using light beams or light pulses transmitted through at least a portion of the scope. The scope may be a commercially available off-the-shelf scope. The imaging device may be a commercially available off-the-shelf imaging device. In some alternative embodiments, the TOF adapter unit may be operably coupled to the scope and the at least one imaging device.

The scope may comprise a laparoscope, an endoscope, a borescope, a videoscope, or a fiberscope. The scope may be optically coupled to or in optical communication with an imaging device (e.g., a TOF imaging device). The imaging device may be configured to generate one or more medical images using light beams or light pulses transmitted through a hollow inner region of the scope. In some cases, the imaging device may be a TOF imaging device configured to generate one or more depth maps or depth images of a target region or surgical scene using TOF light transmitted through the scope.

In some cases, the scope may be optically coupled to or in optical communication with a plurality of imaging devices. The plurality of imaging devices may comprise, for example, an RGB imaging device, a laser speckle imaging device, a fluorescence imaging device, and/or a TOF imaging device. In some cases, the scope may be configured to transmit a combined light beam to a target region. The combined light beam may comprise a plurality of light beams or light pulses generated using a plurality of light sources (e.g., a white light source, a laser speckle light source, a TOF light source, and/or a fluorescence excitation light source). The combined light beam may be reflected from the target region and transmitted back through the scope. The plurality of imaging devices may be configured to (i) receive at least a subset of the light beams or light pulses transmitted through the scope and (ii) generate one or more medical images based on said subset of light beams or light pulses transmitted through the scope. In some cases, the plurality of imaging devices may be configured for different types of imaging modalities (e.g., RGB imaging, laser speckle imaging, fluorescence imaging, TOF imaging, etc.). As described in greater detail below, the combined light beam may be split using an optical element (e.g., a beam splitter or a dichroic mirror) so that different portions or subsets of the combined light beam are provided to different imaging devices or sensors.

The imaging devices may comprise any imaging device configured to generate one or more medical images using light beams or light pulses transmitted through the scope. For example, the imaging devices may comprise a camera, a video camera, a three-dimensional (3D) depth camera, a stereo camera, a depth camera, a Red Green Blue Depth (RGB-D) camera, a time-of-flight (TOF) camera, an infrared camera, a charge coupled device (CCD) image sensor, and/or a complementary metal oxide semiconductor (CMOS) image sensor.

The TOF adapter unit and/or the TOF depth sensor may be used to obtain one or more TOF measurements of a target region. The target region may comprise one or more biological materials (e.g., tissue). The target region may be on or within a surgical subject's body. In some cases, the target region may not or need not be on or within a surgical subject's body. The TOF measurements may correspond to an amount of time required for a transmitted TOF light pulse to be received by the TOF depth sensor. The TOF light pulse may be directed towards the target region and reflected from the target region before reaching the TOF depth sensor. The TOF measurements may be used to generate a depth map of the target region. The depth map may comprise an image or an image channel (i.e., a data set comprising one or more numerical values associated with the pixels of an image) that contains information relating to a distance or a depth of one or more points, features, and/or surfaces within the surgical scene, relative to a reference viewpoint. The reference viewpoint may correspond to a location of a TOF depth sensor relative to one or more portions of the surgical scene. The depth map may comprise depth values for a plurality of points or locations within the surgical scene. The depth values may correspond to a distance between (i) a TOF depth sensor or a TOF imaging device and (ii) a plurality of points or locations within the surgical scene.

In some cases, the depth map may be generated using a time of flight (TOF) sensor. The TOF sensor may be integrated with or operatively coupled to the TOF imaging device. The TOF sensor may be configured to obtain TOF depth measurements based in part on a time it takes for light (e.g., a light wave, a light pulse, or a light beam) to travel from the surgical scene to a detector of the TOF sensor after being reflected off of one or more features present or visible within the surgical scene. The TOF imaging device may be configured to use the TOF depth measurements to generate one or more depth maps. In some cases, the depth map may be refined, updated, corrected, modified, or verified using a stereoscopic camera. The one or more depth maps may be used to provide a medical operator with a more accurate real-time visualization of a distance between a tool and a particular point or feature within the surgical scene. In some cases, the one or more depth maps may provide a surgeon with spatial information about the surgical scene to optimally maneuver a scope, robotic camera, robotic arm, or surgical tool relative to one or more features within the surgical scene.

The system may comprise a plurality of light sources comprising (i) a time of flight (TOF) light source configured to generate a TOF light. In some cases, the plurality of light sources may further comprise (ii) at least one of a white light source, a laser speckle light source, and a fluorescence excitation light source. In other cases, the plurality of light sources may not or need not comprise a white light source, a laser light source, or a fluorescence excitation light source.

The TOF light source may comprise a laser or a light emitting diode (LED). The laser or the light emitting diode (LED) may be configured to generate a TOF light. The TOF light may comprise an infrared or near infrared light having a wavelength from about 700 nanometers (nm) to about 1 millimeter (mm). In some cases, the TOF light may comprise visible light having a wavelength from about 400 nm to about 700 nm. In some cases, the visible light may comprise blue light having a wavelength from about 400 nm to about 500 nm. Advantages of visible light for TOF applications include low penetration of tissue surfaces, which can improve the reliability and accuracy of TOF measurements. In contrast, IR light, which penetrates tissue surfaces deeper and induces multi-reflections, can (a) cause ambiguity as to which internal surface or subsurface is reflecting the IR light, and (b) introduce errors in any TOF measurements obtained. In some cases, the TOF light may comprise a plurality of light beams and/or light pulses having a plurality of wavelengths from about 400 nm to about 1 mm.

In some embodiments, the TOF light source may be used to generate a plurality of TOF light pulses. In such cases, the TOF light source may be pulsed (i.e., switched ON and OFF at one or more predetermined intervals). In some cases, such pulsing may be synced to an opening and/or a closing of one or more TOF camera shutters.

In some embodiments, the TOF light source may be used to generate a continuous TOF light beam. In some cases, the TOF light source may be continuously ON, and a property of the TOF light may be modulated. For example, the continuous TOF light beam may undergo an amplitude modulation. The amplitude modulated TOF light beam may be used to obtain one or more TOF measurements based on a phase difference between the emitted TOF light and the reflected TOF light. The TOF depth measurements may be computed based at least in part on a phase shift observed between the TOF light directed to the target region and the TOF light reflected from the target region. In other cases, when the TOF light source is used to generate a continuous TOF light beam, one or more movable mechanisms (e.g., an optical chopper or a physical shuttering mechanism such as an electromechanical shutter or gate) may be used to generate a series of TOF pulses from the continuous TOF light beam. The plurality of TOF light pulses may be generated by using a movement of the electromechanical shutter or gate to chop, split, or discretize the continuous light beam into the plurality of TOF light pulses. The advantage of having the TOF light beam continuously on is that there are no delays in ramp-up and ramp-down (i.e., no delays associated with powering the beam on and off).

In some embodiments, the TOF light source may be located remote from the scope and operatively coupled to the scope via a light guide. For example, the TOF light source may be located on or attached to a surgical tower. In other embodiments, the TOF light source may be located on the scope and configured to provide the TOF light to the scope via a scope-integrated light guide. The scope-integrated light guide may comprise a light guide that is attached to or integrated with a structural component of the scope. The light guide may comprise a thin filament of a transparent material, such as glass or plastic, which is capable of transmitting light signals through successive internal reflections. Alternatively, the TOF light source may be configured to provide the TOF light to the target region via one or more secondary illuminating scopes. In such cases, the system may comprise a primary scope that is configured receive and direct light generated by other light sources (e.g., a white light source, a laser speckle light source, and/or a fluorescence excitation light source). The one or more secondary illuminating scopes may be different than the primary scope. The one or more secondary illuminating scopes may comprise a scope that is separately controllable or movable by a medical operator or a robotic surgical system. The one or more secondary illuminating scopes may be provided in a first set of positions or orientations that is different than a second set of positions or orientations in which the primary scope is provided. In some cases, the TOF light source may be located at a tip of the scope. In other cases, the TOF light source may be attached to a portion of the surgical subject's body. The portion of the surgical subject's body may be proximal to the target region being imaged using the medical imaging systems of the present disclosure. In any of the embodiments described herein, the TOF light source may be configured to illuminate the target region through a rod lens. The rod lens may comprise a cylindrical lens configured to enable beam collimation, focusing, and/or imaging. In some cases, the TOF light source may be configured to illuminate the target region through a series or a combination of lenses (e.g., a series of relay lenses).

The white light source may be configured to generate one or more light beams or light pulses having one or more wavelengths that lie within the visible spectrum. The white light source may comprise a lamp (e.g., an incandescent lamp, a fluorescent lamp, a compact fluorescent lamp, a halogen lamp, a metal halide lamp, a fluorescent tube, a neon lamp, a high intensity discharge lamp, or a low pressure sodium lamp), a light bulb (e.g., an incandescent light bulb, a fluorescent light bulb, a compact fluorescent light bulb, or a halogen light bulb), and/or a light emitting diode (LED). The white light source may be configured to generate a white light beam. The white light beam may be a polychromatic emission of light comprising one or more wavelengths of visible light. The one or more wavelengths of light may correspond to a visible spectrum of light. The one or more wavelengths of light may have a wavelength between about 400 nanometers (nm) and about 700 nanometers (nm). In some cases, the white light beam may be used to generate an RGB image of a target region.

The laser speckle light source may comprise one or more laser light sources. The laser speckle light source may comprise one or more light emitting diodes (LEDs) or laser light sources configured to generate one or more laser light beams with a wavelength between about 700 nanometers (nm) and about 1 millimeter (mm). In some cases, the one or more laser light sources may comprise two or more laser light sources that are configured to generate two or more laser light beams having different wavelengths. The two or more laser light beams may have a wavelength between about 700 nanometers (nm) and about 1 millimeter (mm). The laser speckle light source may comprise an infrared (IR) laser, a near-infrared laser, a short-wavelength infrared laser, a mid-wavelength infrared laser, a long-wavelength infrared laser, and/or a far-infrared laser. The laser speckle light source may be configured to generate one or more light beams or light pulses having one or more wavelengths that lie within the invisible spectrum. The laser speckle light source may be used for laser speckle imaging of a target region.

In some cases, the plurality of light sources may comprise a fluorescence excitation light source. The fluorescence excitation light source may be used for fluorescence imaging. As used herein, fluorescence imaging may refer to the imaging of any fluorescent or fluorescing materials (e.g., dyes comprising a fluorescent substance like fluorescein, coumarin, cyanine, rhodamine, or any chemical analog or derivative thereof). The fluorescence excitation light source may be configured to generate a fluorescence excitation light beam. The fluorescence excitation light beam may cause a fluorescent dye (e.g., indocyanine green) to fluoresce (i.e., emit light). The fluorescence excitation light beam may have a wavelength of between about 600 nanometers (nm) and about 900 nanometers (nm). The fluorescence excitation light beam may be emitted onto a target region. In some cases, the target region may comprise one or more fluorescent dyes configured to absorb the fluorescence excitation light beam and re-emit fluorescent light with a wavelength between about 750 nanometers (nm) and 950 nanometers (nm). In some cases, the one or more fluorescent dyes may be configured to absorb the fluorescence excitation light beam and to re-emit fluorescent light with a wavelength between about 700 nanometers (nm) and about 2.5 micrometers ($\mu$m).

In any of the embodiments described herein, the plurality of light sources may be configured to generate one or more light beams. In such cases, the plurality of light sources may be configured to operate as a continuous wave light source. A continuous wave light source may be a light source that is configured to produce a continuous, uninterrupted beam of light with a stable output power.

In some cases, the plurality of light sources may be configured to continuously emit pulses of light and/or energy at predetermined intervals. In such cases, the light sources may only be switched on for limited time intervals, and may alternate between a first power state and a second power state. The first power state may be a low power state or an OFF state. The second power state may be a high power state or an ON state.

Alternatively, the plurality of light sources may be operated in a continuous wave mode, and the one or more light beams generated by the plurality of light sources may be chopped (i.e., separated or discretized) into a plurality of light pulses using a mechanical component (e.g., a physical object) that blocks the transmission of light at predetermined intervals. The mechanical component may comprise a movable plate that is configured to obstruct an optical path of one or more light beams generated by the plurality of light sources, at one or more predetermined time periods.

The system may comprise a scope. The scope may comprise a light port configured to receive one or more light beams or light pulses generated by the plurality of light sources. The scope may be in optical communication with the plurality of light sources via one or more light guides. The scope may be attached or releasably coupled to the TOF adapter unit described above.

The scope may be configured to direct a plurality of light beams or light pulses generated by the plurality of light sources to a target region. The plurality of light beams or light pulses may comprise the TOF light generated using the TOF light source.

The plurality of light beams or light pulses generated by the plurality of light sources may be reflected off of the target region. The reflected light beams or light pulses may be transmitted back through the scope via the tip of the scope. The scope may be configured to receive the reflected light beams or light pulses and to direct the reflected light beams or light pulses to one or more imaging devices. The plurality of reflected light beams or light pulses may comprise TOF light beams or TOF light pulses reflected off of the target region.

The system may comprise a TOF sensor configured to receive at least a portion of the plurality of light beams or light pulses that are reflected from the target region. The portion may comprise one or more TOF light beams or TOF light pulses reflected from the target region.

The TOF sensor may be used to obtain one or more TOF measurements of the target region. The one or more TOF measurements may be computed based at least in part on an amount of time taken by a traveling moiety (e.g., an object, particle, or wave) to travel a distance through a medium (e.g., fluid, such as a liquid or gas). The time measurement(s) may be used to establish a velocity or path length of the travel moiety, as well as the medium's properties (e.g., density, composition, flow rate, etc.). In some cases, the time of flight measurements may correspond to the time required for emitted electromagnetic radiation to travel from a source of the electronic radiation to a sensor (e.g., a camera). In other cases, the time of flight measurements may correspond to the time required for the emitted electromagnetic radiation to reach a target tissue. Alternatively, the time of flight measurements may correspond to the time required for the emitted electromagnetic radiation to reach a target tissue and be directed (e.g., reflected back) to a TOF sensor.

In some cases, the TOF sensor may be positioned along a common beam path of the plurality of light beams or light pulses reflected from the target region. The common beam path may be disposed between the target region and an optical element that can be used to split the plurality of light beams or light pulses into different sets of light signals. In some cases, the plurality of light beams or light pulses reflected from the target region may be split into (i) a first set of light signals corresponding to the TOF light and (ii) a second set of light signals corresponding to white light, laser speckle light, or fluorescence excitation light. In such cases, the TOF sensor may be positioned along a discrete beam path of the first set of light signals (i.e., downstream of the optical element).

In some cases, the TOF sensor may be positioned at a tip of the scope. In other cases, the TOF sensor may be attached to a portion of the surgical subject's body. The portion of the surgical subject's body may be proximal to the target region being imaged.

In some embodiments, the system may comprise a plurality of depth sensing devices. Each of the plurality of depth sensing devices may be configured to obtain the one or more TOF measurements used to generate the depth map of the target region. The plurality of depth sensing devices may be selected from the group consisting of a stereo imaging device (e.g., a stereoscopic camera), a structured light imaging device, and a TOF depth sensor.

In some embodiments, the TOF sensor may comprise an imaging sensor configured to implement heterodyning to enable depth sensing and to enhance TOF resolution. Heterodyning can enable a slower sensor to sense depth, and may permit the use of regular camera sensors, instead of dedicated TOF hardware sensors, for TOF sensing.

The system may comprise an image processing unit configured to generate a depth map of the target region based at least in part on one or more TOF measurements obtained using the TOF sensor. The image processing unit may comprise any of the imaging devices or imaging sensors described herein. In some cases, the image processing unit may be integrated with one or more imaging devices or imaging sensors. As described above, the depth map may comprise an image or an image channel that contains information relating to a distance or a depth of one or more surfaces within the target region, relative to a reference viewpoint. The reference viewpoint may correspond to a location of a TOF depth sensor relative to one or more portions of the target region. The depth map may comprise depth values for a plurality of points or locations within the target region. The depth values may correspond to a distance between (i) a TOF depth sensor or a TOF imaging device and (ii) a plurality of points or locations within the target region.

In some embodiments, the system may further comprise an optical element configured to separate the plurality of light beams or light pulses reflected from the target region into (i) a first set of light signals corresponding to the TOF light and (ii) a second set of light signals corresponding to white light, laser speckle light, or fluorescence excitation light. The optical element may be configured to direct the first set of light signals to the TOF sensor and the second set of light signals to one or more imaging devices or sensors (e.g., an RGB imaging sensor, a laser speckle imaging sensor, and/or a fluorescence imaging sensor). In some cases, the one or more imaging devices may comprise a camera or a sensor configured for TOF imaging, RGB imaging, laser speckle imaging, and/or fluorescence imaging. In some cases, the optical element may comprise a beam splitter. In other cases, the optical element may comprise a dichroic mirror.

In some embodiments, the system may further comprise a TOF light modulator. The TOF light modulator may be configured to adjust one or more properties (e.g., illumination intensity, direction of propagation, travel path, etc.) of the TOF light generated using the TOF light source. In some cases, the TOF light modulator may comprise a diverging lens that is positioned along a light path of the TOF light. The diverging lens may be configured to modulate an illumination intensity of the TOF light across the target region. In other cases, the TOF light modulator may comprise a light diffusing element that is positioned along a light path of the TOF light. The light diffusing element may likewise be configured to modulate an illumination intensity of the TOF light across the target region. Alternatively, the TOF light modulator may comprise a beam steering element configured to illuminate the target region and one or regions proximal to the target region. The beam steering element may be used to illuminate a greater proportion of a scene comprising the target region. In some cases, the beam steering element may comprise a lens or a mirror (e.g., a fast steering mirror).

In some embodiments, the system may further comprise a TOF parameter optimizer configured to adjust one or more pulse parameters and one or more camera parameters, based at least in part on a desired application, depth range, tissue type, scope type, or procedure type. The one or more TOF measurements obtained using the TOF sensor may be based at least in part on the one or more pulse parameters and the one or more camera parameters. For example, the TOF parameter optimizer may be used to implement a first set of pulse parameters and camera parameters for a first procedure, and to implement a second set of pulse parameters and camera parameters for a second procedure. In some cases, the first procedure and the second procedure may have different depth ranges of interest. The TOF parameter optimizer may be configured to adjust the one or more pulse parameters and/or the one or more camera parameters to improve a resolution, accuracy, or tolerance of TOF depth sensing, and to increase the TOF signal to noise ratio for TOF applications. In some cases, the TOF parameter optimizer may be configured to determine the actual or expected performance characteristics of the TOF depth sensing system based on a desired selection or adjustment of one or more pulse parameters or camera parameters. Alternatively, the TOF parameter optimizer may be configured to determine a set of pulse parameters and camera parameters required to achieve a desired resolution, accuracy, or tolerance for a desired depth range or surgical operation.

In some cases, the TOF parameter optimizer may be configured to adjust the one or more pulse parameters and the one or more camera parameters in real time. In other cases, the TOF parameter optimizer may be configured to adjust the one or more pulse parameters and the one or more camera parameters offline. In some cases, the TOF parameter optimizer may be configured to adjust the one or more pulse parameters and/or camera parameters based on a feedback loop. The feedback loop may be implemented using a controller (e.g., a programmable logic controller, a proportional controller, a proportional integral controller, a proportional derivative controller, a proportional integral derivative controller, or a fuzzy logic controller). In some cases, the feedback loop may comprise a real-time control loop that is configured to adjust the one or more pulse parameters and/or the one or more camera parameters based on a temperature of the TOF light source or the TOF sensor. In some embodiments, the system may comprise an image post processing unit configured to update the depth map based on an updated set of TOF measurements obtained using the one or more adjusted pulse parameters or camera parameters.

The TOF parameter optimizer may be configured to adjust one or more pulse parameters. The one or more pulse parameters may comprise, for example, an illumination intensity, a pulse width, a pulse shape, a pulse count, a pulse on/off level, a pulse duty cycle, a TOF light pulse wavelength, a light pulse rise time, and a light pulse fall time. The illumination intensity may correspond to an amount of laser power needed to provide a sufficient detectable TOF light signal during a laparoscopic procedure. The pulse width may correspond to a duration of the pulses. The TOF system may require a time of flight laser pulse of some minimal or maximal duration to guarantee a certain acceptable depth resolution. The pulse shape may correspond to a phase, an amplitude, or a period of the pulses. The pulse count may correspond to a number of pulses provided within a predetermined time period. Each of the pulses may have at least a predetermined amount of power (in Watts) in order to enable single pulse time of flight measurements with reduced noise. The pulse on/off level may correspond to a pulse duty cycle. The pulse duty cycle may be a function of the ratio of pulse duration or pulse width (PW) to the total period (T) of the pulse waveform. The TOF pulse wavelength may correspond to a wavelength of the TOF light from which the TOF light pulse is derived. The TOF pulse wavelength may be predetermined, or adjusted accordingly for each desired TOF application. The pulse rise time may correspond to an amount of time for the amplitude of a pulse to rise to a desired or predetermined peak pulse amplitude. The pulse fall time may correspond to an amount of time for the peak pulse amplitude to fall to a desired or predetermined value. The pulse rise time and/or the pulse fall time may be modulated to meet a certain threshold value. In some cases, the TOF light source may be pulsed from a lower power mode (e.g., 50%) to higher power mode (e.g., 90%) to minimize rise time. In some cases, a movable plate may be used to chop a continuous TOF light beam into a plurality of TOF light pulses, which can also minimize or reduce pulse rise time.

The TOF parameter optimizer may be configured to adjust one or more camera parameters. The camera parameters may include, for example, a number of shutters, shutter timing, shutter overlap, shutter spacing, and shutter duration. As used herein, a shutter may refer to a physical shutter and/or an electronic shutter. A physical shutter may comprise a movement of a shuttering mechanism (e.g., a leaf shutter or a focal-plane shutter of an imaging device or imaging sensor) in order to control exposure of light to the imaging device or imaging sensor. An electronic shutter may comprise turning one or more pixels of an imaging device or imaging sensor ON and/or OFF to control exposure. The number of shutters may correspond to a number of times in a predetermined time period during which the TOF camera is shuttered open to receive TOF light pulses. In some cases, two or more shutters may be used for a TOF light pulse. Temporally spaced shutters can be used to deduce the depth of features in the target region. In some cases, a first shutter may be used for a first pulse (e.g., an outgoing pulse), and a second shutter may be used for a second pulse (e.g., an incoming pulse). Shutter timing may correspond to a timing of shutter opening and/or shutter closing based on a timing of when a pulse is transmitted and/or received. The opening and/or closing of the shutters may be adjusted to capture one or more TOF pulses or a portion thereof. In some cases, the shutter timing may be adjusted based on a path length of the TOF pulses or a depth range of interest. Shutter timing modulation may be implemented to minimize the duty cycle of TOF light source pulsing and/or camera shutter opening and closing, which can enhance the operating conditions of the TOF light source and improve hardware longevity (e.g., by limiting or controlling the operating temperature). Shutter overlap may correspond to a temporal overlap of two or more shutters. Shutter overlap may increase peak Rx power at short pulse widths where peak power is not immediately attained. Shutter spacing may correspond to the temporal spacing or time gaps between two or more shutters. Shutter spacing may be adjusted to time the TOF camera shutters to receive the beginning and/or the end of the pulse. Shutter spacing may be optimized to increase the accuracy of TOF measurements at decreased Rx power. Shutter duration may correspond to a length of time during which the TOF camera is shuttered open to receive TOF light pulses. Shutter duration may be modulated to minimize noise associated with a received TOF light signal, and to ensure that the TOF camera receives a minimum amount of light needed for TOF depth sensing applications.

In some cases, hardware may be interchanged or adjusted in addition to or in lieu of software-based changes to pulse parameters and camera parameters, in order to achieve the desired depth sensing capabilities for a particular depth sensing application.

In some cases, the system may further comprise an image post processing unit configured to update the depth map based on temperature fluctuations associated with an operation of the TOF light source or the TOF sensor, thereby enhancing depth sensing accuracy and surgical safety. Such temperature fluctuations may create visual aberrations, errors, distortions, or irregularities in the depth map. Compensating for temperature-induced errors in the depth map may also enhance safety during a surgical operation (e.g., by providing a more accurate assessment of a distance between a surgical tool and one or more critical structures in the target region so that a surgeon can constrain movement of the surgical tool in a Z-direction and minimize injury to the critical structures).

In some cases, the image post processing unit configured to perform image post processing on the depth map to enhance depth sensing accuracy and surgical safety. The image post processing may comprise at least one of spatial filtering and temporal filtering based on a measured depth of a feature or a pixel within the depth map. In some cases, the image post processing may comprise adjusting a size of a filtering kernel. The size of the filtering kernel may be adjustable based on a measured depth of one or more features in the target region in order to maintain a desired imaging resolution at said measured depth. Changing a size of the filtering kernel may allow an image processing algorithm to refine depth map values for one or more pixels in the depth map based on (i) depth map values for neighboring pixels and (ii) a weighting function for the depth map values associated with each pixel and its neighboring pixels. This may permit filtering more heavily for closer depths while maintaining sub-mm resolutions.

In some embodiments, the system may further comprise a calibration unit configured to perform at least one of (i) camera calibration to correct camera reprojection errors and distortions in an XY plane and (ii) depth calibration to correct for depth measurement distortions along a Z axis. Camera calibration may be performed for the TOF camera. Depth calibration may be performed for the TOF depth sensor.

The calibration unit may be configured to perform the camera calibration and/or the depth calibration using a calibration target. In some cases, the calibration target may be a stationary target located on a static rig. In other cases, the calibration target may be a target located on a movable rig. In some cases, the calibration unit may be configured to perform the camera calibration or the depth calibration using a video of the calibration target. The calibration target may be moving or stationary. The video may be used to determine a change in a position and/or an orientation of the calibration target over time.

In some cases, the calibration unit may be configured to perform the camera calibration or the depth calibration using camera reconstruction quality as feedback. In such cases, the depth camera may reconstruct a calibration target (e.g., an object with a known size/shape) in three-dimensional (3D) space, and the calibration unit may compare the 3D reconstruction to the size, shape, and/or dimensions of the calibration target in real space. The comparison of the 3D reconstruction to the calibration target in real space can provide feedback for both camera and depth calibration.

In some cases, the calibration unit may be configured to perform the camera calibration or the depth calibration based at least in part on TOF light angle entry correction. In cases where a light guide such as a fiber optic cable is used, angled light entry can cause delays in the transmission of the TOF light along fiber optic cable due to the angled light bouncing off of internal surfaces of fiber optic cable. The calibration unit may be configured to correct distortions in the depth map due to such delays caused by angled light entry.

In some cases, the calibration unit may be configured to perform the camera calibration or the depth calibration based on IR intensity error calibration or RGB intensity error correction.

The medical imaging systems described herein may be configured to adjust TOF image acquisition parameters for different tissues/organs based on prior experiments and/or real-time optimizations. The TOF image acquisition parameters may comprise the pulse parameters and/or camera parameters described above. The different tissues/organs may be identified using a separate RGB image and/or a separate TOF depth image obtained at an earlier time. In some cases, the different tissues/organs may be identified using a live RGB image and/or a live TOF depth image.

The medical imaging systems described herein may be configured to perform real time camera calibration and real time depth calibration for different tissues/organs based on prior experiments and/or real-time optimizations. The medical imaging systems described herein may be configured to perform live camera or depth calibration based on the real-time acquisition of one or more images of a calibration target visible within the target region.

In some cases, the medical imaging systems described herein may be configured to perform pulse parameter optimizations, camera parameter optimizations, camera calibrations, and/or depth calibrations, based on a desired application, depth range, tissue type, scope type, tool selection, or procedure type.

In some cases, a single imaging sensor may be used for both depth imaging and laser speckle imaging. In some cases, the TOF sensors described herein may comprise an imaging sensor configured for TOF imaging and at least one of RGB imaging, laser speckle imaging, and fluorescence imaging. In some cases, the imaging sensor may be configured for TOF imaging and perfusion imaging. In any of the embodiments described herein, the TOF sensor may be configured to see and register non-TOF light.

In some cases, the imaging sensor may be configured to capture TOF depth signals and laser speckle signals during alternating or different temporal slots. For example, the imaging sensor may capture a TOF depth signal at a first time instance, a laser speckle signal at a second time instance, a TOF depth signal at a third time instance, a laser speckle signal at a fourth time instance, and so on. The imaging sensor may be configured to capture a plurality of optical signals at different times. The optical signals may comprise a TOF depth signal, an RGB signal, a fluorescence signal, and/or a laser speckle signal.

In other cases, the imaging sensor may be configured to simultaneously capture TOF depth signals and laser speckle signals to generate one or more medical images comprising a plurality of spatial regions. The plurality of spatial regions may correspond to different imaging modalities. For example, a first spatial region of the one or more medical images may comprise a TOF depth image based on TOF measurements, and a second spatial region of the one or more medical images may comprise a laser speckle image based on laser speckle signals.

In some embodiments, the system may further comprise an image post processing unit configured to normalize an RGB image of the target region, a fluorescent image of the target region, or speckle based flow and perfusion signals associated with the target region, based at least in part on one or more TOF depth measurements obtained using the TOF sensor.

In some cases, an image of the target region may exhibit shading effects that are not visually representative of the actual target region. When an image of a surgical scene is obtained by illuminating the surgical scene with light directed through a scope (e.g., a laparoscope, an endoscope, a borescope, a videoscope, or a fiberscope), the image may comprise a radial shading gradient. The radial shading gradient may correspond to a light intensity fall-off pattern that varies as a function of an inverse square of a distance from a center point of illumination. The light intensity fall-off pattern may also vary as a function of a distance from a tip of the scope to the center point of illumination. The light intensity fall-off pattern may be a function of (i) a vertical distance from a tip of the scope to a center point of illumination within the surgical scene and (ii) a horizontal distance from the center point of illumination to the one or more pixels of the initial image. The one or more TOF depth measurements obtained using the TOF sensor may be used to reduce or eliminate misleading, deceiving, or erroneous shading effects present within an image generated using RGB data, laser speckle signals, and/or fluorescence characteristics.

In some cases, the image post processing unit may be configured to use an illumination profile of the target region and a distance between the scope and the target region being imaged to correct for image intensity at a periphery of one or more RGB or fluorescent images obtained using light pulses or light beams transmitted through the scope. In some cases, the image post processing unit may be configured to use a constant hematocrit concentration (i.e., the proportion of blood that consists of red blood cells, by volume) to estimate blood flow velocity through or proximal to the target region.

In some embodiments, the system may further comprise a processor configured to determine a translational and a rotational motion of the scope, based at least in part on (i) a known position or a known depth of the target region and (ii) a known velocity of the scope or scope assembly. In some cases, the processor may be configured to refine a computation of the translational and rotational motion of the scope based at least in part on one or more kinematic measurements obtained using a motion sensor or an inertial measurement unit.

The processor may be configured to use the translational and rotational motion of the scope to reduce speckle motion artifacts. Speckle motion artifacts may comprise visual artifacts in a speckle image due to external motions of a scope or TOF sensor relative to a target tissue surface.

The processor may be configured to use the translational and rotational motion of the scope to perform three-dimensional (3D) reconstruction of the target region. 3D reconstruction may comprise stitching together multiple images of different portions of a surgical scene to create a larger, combined image of the surgical scene.

The processor may be configured to use the translational and rotational motion of the scope to generate a minimap. The minimap may comprise a visual representation of which portion of a global map is currently being displayed/imaged/visualized using the scope assembly.

In some embodiments, the processor may be further configured to use the translational and/or rotational motion of the scope to simulate binocular vision. In some cases, the processor may be configured to perform image scaling, determine a proximity of objects or features relative to the scope, or perform grid overlays on one or more images obtained using the scope.

The processor may be configured to use the translational and rotational motion of the scope to autonomously control a position or an orientation of a robotic arm, a robotic camera, or a surgical tool. For example, the processor may be configured to reposition the robotic arm, camera, or tool relative to the scope to provide a surgeon, the scope, the robotic arm, the camera, and/or the tool with line of sight access to the target region or a portion thereof. In some cases, the processor may be configured to use the position, orientation, or motion of the scope relative to the surgical scene to reposition the robotic arm, camera, or tool relative to the scope and/or the surgical scene.

In some cases, the processor may be configured to control a motion of a robot based at least in part on the one or more TOF depth measurements obtained using the TOF sensor. The robot may comprise a robotic camera, a robotic tool, or a robotic arm configured to manipulate one or more surgical tools. The processor may be configured to position or move the robotic arm, camera, or tool to provide a surgeon, an operator, the robotic arm, the robotic camera, the robotic tool, and/or the scope with line of sight access to the target region. In some cases, the processor may be configured to control a motion of the robotic camera, tool, or arm in part based on a position, orientation, and/or motion of the scope relative to one or more features within the target region or surgical scene. As described above, the position, orientation, and/or motion of the scope may be determined using one or more TOF depth measurements.

In some cases, the processor may be configured to control the robot based on the preferences of a surgeon or the steps of surgical procedure. For example, a surgeon may prefer to operate at a certain depth, or a certain step of a surgical procedure may require medical operations or image acquisitions at a certain depth.

In some embodiments, the system may further comprise a stereo imaging device configured to obtain a set of depth measurements of the target region. In such embodiments, the image processing unit may be configured to generate the depth map based at least in part on the set of depth measurements obtained using the stereo imaging device and the one or more TOF depth measurements obtained using the TOF sensor. In some embodiments, the image processing unit may be configured to use the one or more TOF depth measurements obtained using the TOF depth sensor to train a stereo imaging algorithm or a monocular depth algorithm. The stereo imaging algorithm and/or the monocular depth algorithm may be configured to process the set of depth measurements obtained using the stereo imaging device. In some cases, a combination of stereo imaging and TOF imaging can be used to (1) mitigate complexities of stereo image processing and (2) refine TOF measurements.

In any of the embodiments described herein, the image processing unit may be configured to generate one or more RGB images, laser speckle images, or fluorescence images of the target region, based at least in part on the plurality of light beams or light pulses reflected from the target region.

In any of the embodiments described herein, the TOF depth sensor may comprise a single photon avalanche photodiode (SPAD) sensor. The SPAD sensor may comprise a solid-state photodetector with a diode placed within each pixel of the SPAD sensor. Each diode may be configured to receive a single incoming photon of light and to convert the single incoming photon into an "avalanche" of electrons, thereby generating a large electrical pulse signal corresponding to the incoming photon received by the diode. The incoming photon may be associated with one or more TOF light pulses transmitted to and reflected from the target region, as described above.

The SPAD sensor may be based on one or more p-n junctions. The one or more p-n junctions may be reverse-biased. A reverse-biased p-n junction may correspond to a p-n junction with a p-type region connected to the negative terminal of a battery and an n-type region connected to the positive terminal of a battery. In a reverse-biased p-n junction, the voltage at the cathode may be comparatively higher than the voltage at the anode, and minimal current may flow until the diode breaks down. Once the electric field intensity of the p-n junction increases beyond a critical level, the p-n junction depletion zone may break down and induce an electrical current flow, usually by an avalanche breakdown process.

The one or more p-n junctions may be reverse-biased at a voltage Va that exceeds the breakdown voltage Vb of the one or more p-n junctions. The reverse bias of the p-n junctions of the SPAD sensor may produce an electric field that is sufficiently high such that a single charge carrier (e.g., a TOF photon) injected into the depletion layer can trigger a self-sustaining avalanche of electrons, thereby generating an electrical current. If the primary charge carrier is photo-generated, the leading edge of the avalanche pulse may also mark the arrival time of the detected photon.

In contrast with a traditional photodiode, which has a low reverse bias voltage and produces a leakage current that changes linearly with the absorption of photons, a SPAD sensor has a reverse bias that is sufficiently high to enable impact ionization. Impact ionization may occur when a first electron (or hole) with sufficient kinetic energy overcomes the ionization energy of the bulk material, knocks a bound second electron out of its bound state (in the valence band), and promotes the second electron to a state in the conduction band. Impact ionization may be used to produce an avalanche current. A large avalanche of current carriers can grow exponentially and can be triggered by just a single photon-initiated carrier.

In some embodiments, the SPAD sensor may output an electrical signal based on the number of generated pulses it counts. In some embodiments, the SPAD sensor may be configured to perform photon counting, a technique by which the SPAD sensor quantifies the number of photon particles received and determines one or more parameters of the signal light (e.g., intensity and/or time distribution) based on the photon particles received. Photon counting, which treats light as digital signals, can eliminate interference from electronic noise and enable highly accurate detection of weak signals. Additionally, when utilized with processing circuitry, photon counting can be used to accurately detect the amount of light received and the precise time at which one or more photons are detected.

As described above, the SPAD sensor may be configured to detect single photons that provide short duration trigger pulses that can be counted. In some cases, the SPAD sensor can also be used to accurately detect the time of arrival of the incident photons, in part due to the high speed at which the avalanche builds up, and the low timing jitter associated with the SPAD sensor. The ability of the SPAD sensor to convert a single photon into a plurality of electrons can enhance imaging sensitivity and improve the accuracy of any distance measurements obtained using the SPAD sensor. The SPAD sensor can also provide a time resolution sufficient to determine the exact timing at which one or more photons reach a pixel of the SPAD sensor. Leveraging this functionality, the SPAD sensor can be configured for any TOF measurements as described herein, including 3D distance measurements.

Figure 11:
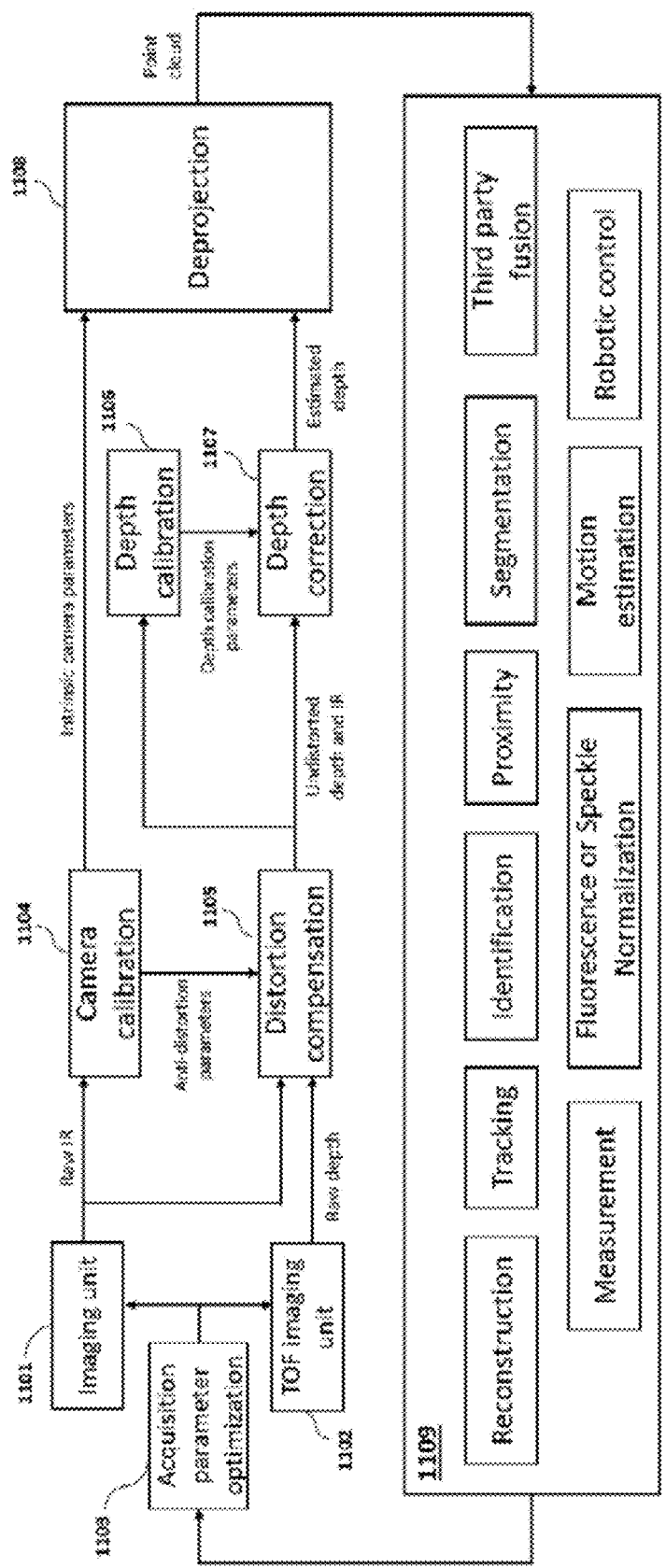
FIG. 11 schematically illustrates a system configured to use a TOF imaging device to perform one or more TOF applications, in accordance with some embodiments.

FIG. 11 illustrates an exemplary system for TOF imaging. The system may be configured to use a TOF imaging device to perform one or more TOF applications. The system may comprise a first imaging unit 1101 and a second imaging unit 1102. The first imaging unit 1101 may comprise an imaging sensor for RGB imaging, laser speckle contrast imaging, and/or fluorescence imaging. The second imaging unit 1102 may comprise any TOF sensor or depth sensor as described herein. The first imaging unit 1101 and the second imaging unit 1102 may be operatively coupled to an acquisition parameter optimizer 1103. The acquisition parameter optimizer 1103 may be configured to adjust, modify, and/or optimize one or more imaging parameters associated with the first imaging unit 1101 and the second imaging unit 1102, based at least in part on a desired application, depth range, tissue type, scope type, and/or procedure type. The imaging parameters may comprise, for example, camera parameters such as number of shutters, shutter timing, shutter overlap, shutter spacing, and shutter duration. The imaging parameters may be adjusted, modified, or optimized for different tissues/organs based on prior experiments and/or real-time optimizations.

In some embodiments, the acquisition parameter optimizer 1103 may be configured to adjust, modify, and/or optimize one or more pulse parameters associated with the light sources used to generate the light pulses or light beams detectable by the first imaging unit 1101 and the second imaging unit 1102. The pulse parameters may comprise, for example, an illumination intensity, a pulse width, a pulse shape, a pulse count, a pulse on/off level, a pulse duty cycle, a TOF light pulse wavelength, a light pulse rise time, and/or a light pulse fall time. The pulse parameters may be adjusted, modified, or optimized for different tissues/organs based on prior experiments and/or real-time optimizations. The pulse parameters may be updated based at least in part on a desired application, depth range, tissue type, scope type, and/or procedure type.

The first imaging unit 1101 may be configured to capture and provide raw IR images to a camera calibration unit 1104. The camera calibration unit 1104 may be configured to generate a set of anti-distortion parameters and/or a set of intrinsic camera calibration parameters based at least in part on the raw IR images. In some cases, the first imaging unit 1101 may be configured to provide the raw IR images to a distortion compensation unit 1105.

The second imaging unit 1102 may be configured to capture and provide raw depth images to a distortion compensation unit 1105. The distortion compensation unit 1105 may be configured to receive the anti-distortion parameters generated by the camera calibration unit 1104 and the raw IR images captured using the first imaging unit 1101. In some cases, the distortion compensation unit 1105 may be configured to generate undistorted depth and IR images based at least in part on the raw depth images, the raw IR images, and/or the anti-distortion parameters received from the camera calibration unit 1104.

The undistorted depth and IR images generated using the distortion compensation unit 1105 may be provided to a depth calibration unit 1106. The depth calibration unit 1106 may be configured to generate a set of depth calibration parameters based at least in part on a calibration target and/or the undistorted depth and IR images received from the distortion compensation unit 1105. The depth calibration unit 1106 may be configured to provide the depth calibration parameters to a depth correction unit 1107. The depth correction unit 1107 may be configured to use the depth calibration parameters to perform depth correction on the undistorted depth and IR images provided by the distortion compensation unit 1105. In some cases, the distortion compensation unit 1105 may be configured to provide the undistorted depth and IR images directly to the depth correction unit 1107. In any of the embodiments described herein, the depth correction unit 1107 may be configured to use the depth calibration parameters to compute an estimated depth of one or more features present in the undistorted depth and IR images, or to update a computation of the estimated depth of such features present in the undistorted depth and IR images.

In some embodiments, the system may comprise an image processing unit 1108. The image processing unit 1108 may be configured to receive the estimated depth computations from the depth correction unit 1107 and the intrinsic camera parameters from the camera calibration unit 1104. The image processing unit 1108 may be configured to generate a point cloud based at least in part on the estimated depth computations and the intrinsic camera parameters. The point cloud may correspond to one or more features present within the images obtained using the first imaging unit 1101 and the second imaging unit 1102. The point cloud may be generated using deprojection. Deprojection may involve using (i) a 2D pixel location in an image and (ii) depth information associated with the image to (iii) map the 2D pixel location to a 3D point location within a 3D coordinate space. The 3D coordinate space may correspond to real space. The image processing unit 1108 and/or the point cloud generated using the image processing unit 1108 may be used to perform a plurality of TOF imaging applications 1109. The plurality of TOF imaging applications 1109 may include, for example, 3D reconstruction, feature tracking, feature identification, qualitative and/or quantitative assessments of feature proximity, image segmentation, third party image fusion, measurement of features, fluorescence and/or speckle image normalization, motion estimation, and/or robotic control.

Figure 12:
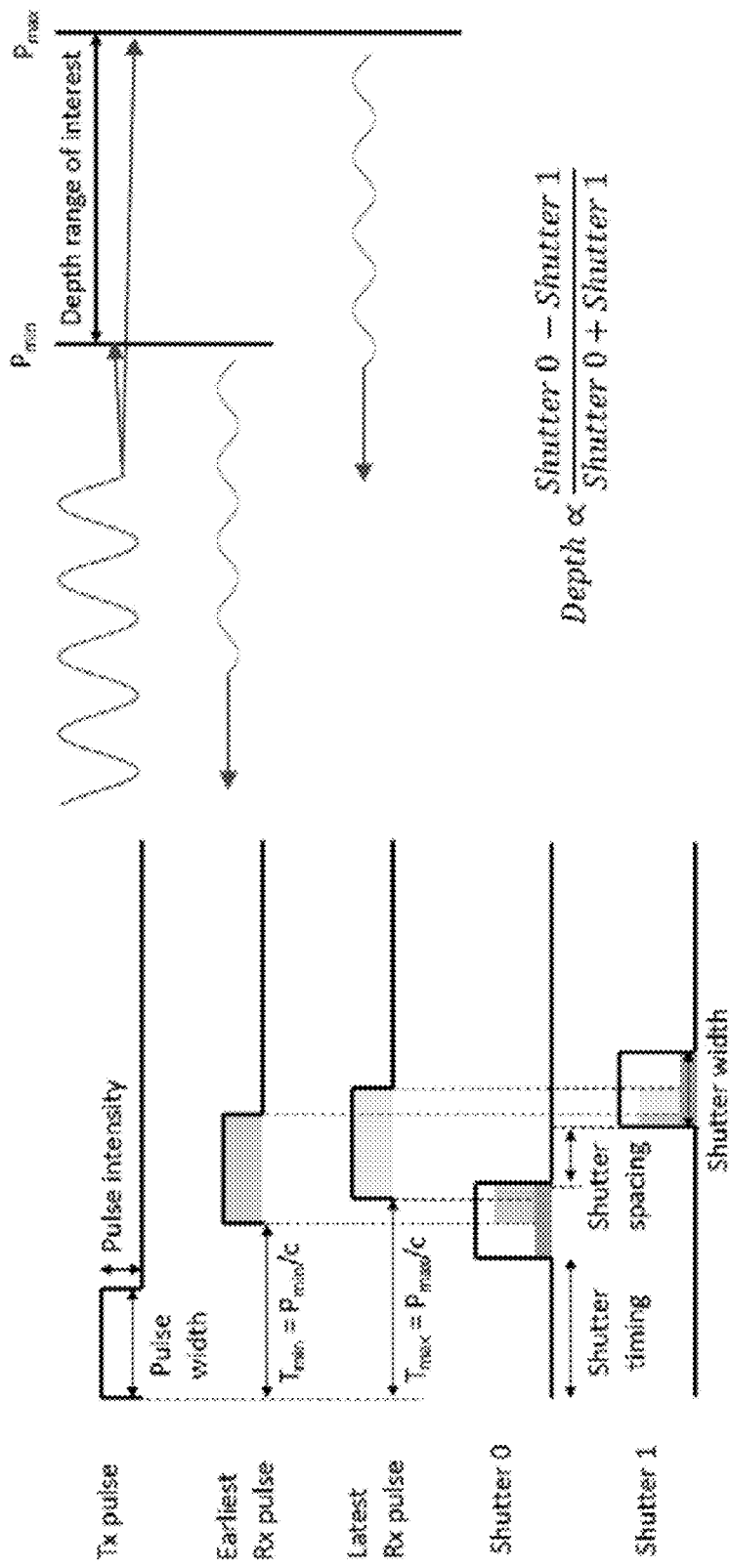
FIG. 12 schematically illustrates a plurality of shutters for capturing and/or registering one or more TOF pulses, in accordance with some embodiments.

FIG. 12 illustrates a plurality of camera shutters for capturing and/or registering one or more TOF pulses. As shown in FIG. 12, when one or more TOF pulses are transmitted to a target region, the one or more TOF pulses may be reflected back at different times depending on a depth of the respective surface off which the TOF pulses are reflected. For example, when a first set of pulses (Tx pulses) are transmitted to a target region, a second pulse (the earliest Rx pulse) and a third pulse (the latest Rx pulse) may be reflected back from the target region. The earliest Rx pulse may be reflected off a portion of the target region having a first depth, and the latest Rx pulse may be reflected off a portion of the target region having a second depth. The second depth may be greater than the first depth. The first depth may correspond to a pathlength $P_{min}$, and the second depth may correspond to a pathlength $P_{max}$. As such, the earliest Rx pulse may be received at $T_{min}=P_{min}/c$, and the latest Rx pulse may be received at $T_{max}=P_{max}/c$, where c equals the speed of light. As shown in FIG. 12, a plurality of shutters (e.g., Shutter 0 and Shutter 1) may be used to capture at least a portion of the earliest received TOF pulse and the latest received TOF pulse. The shutter timing, shutter spacing, and/or shutter width may be adjusted to capture the received TOF pulses or a portion thereof. In some cases, the depth of a feature in the target region may be computed in part based on the following function:

$$\text{Depth} \propto \frac{\text{Shutter 0} - \text{Shutter 1}}{\text{Shutter 0} + \text{Shutter 1}}$$

As used herein, Shutter 0 and Shutter 1 may correspond to the total integrated photon count at each shutter within a frame.

Figure 13B:
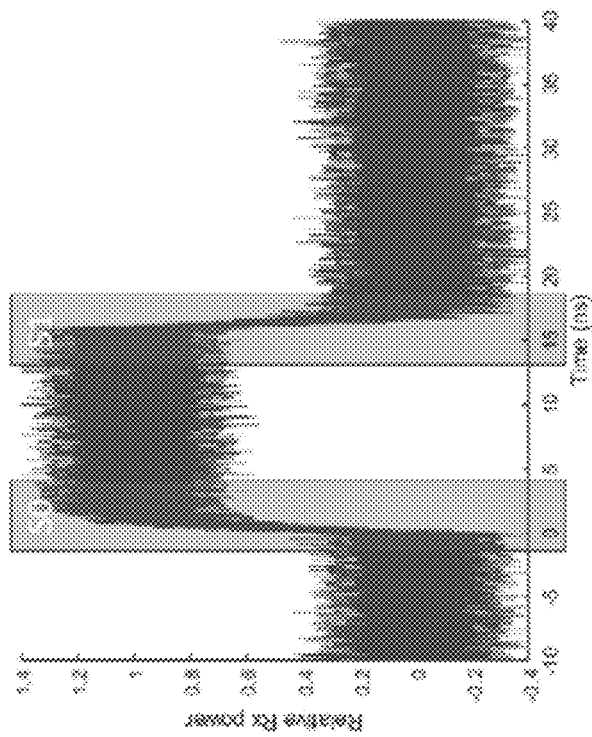
FIG. 13A and FIG. 13B schematically illustrate various examples of shutter spacing, in accordance with some embodiments.
Figure 13A:
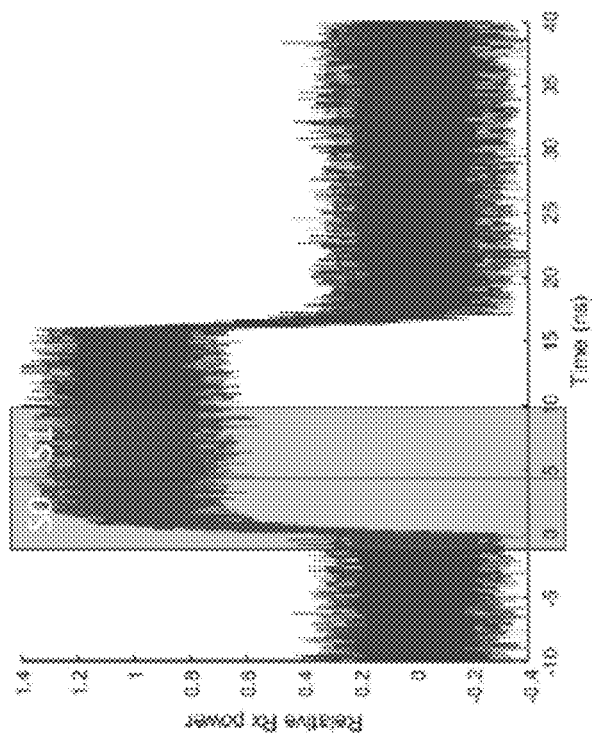

FIG. 13A illustrates an example of a plurality of shutters that are temporally adjacent to each other. In some cases, the plurality of shutters s0 and s1 may be adjacent to each other to capture a signal that exhibits peak Rx power over a predetermined period of time. FIG. 13B illustrates an example of a plurality of shutters that are temporally spaced relative to each other. In some cases, the plurality of shutters s0 and s1 may be temporally spaced to capture a beginning portion and an end portion of a pulse. In some alternative embodiments, the plurality of shutters s0 and s1 may overlap temporally.

Figure 14:
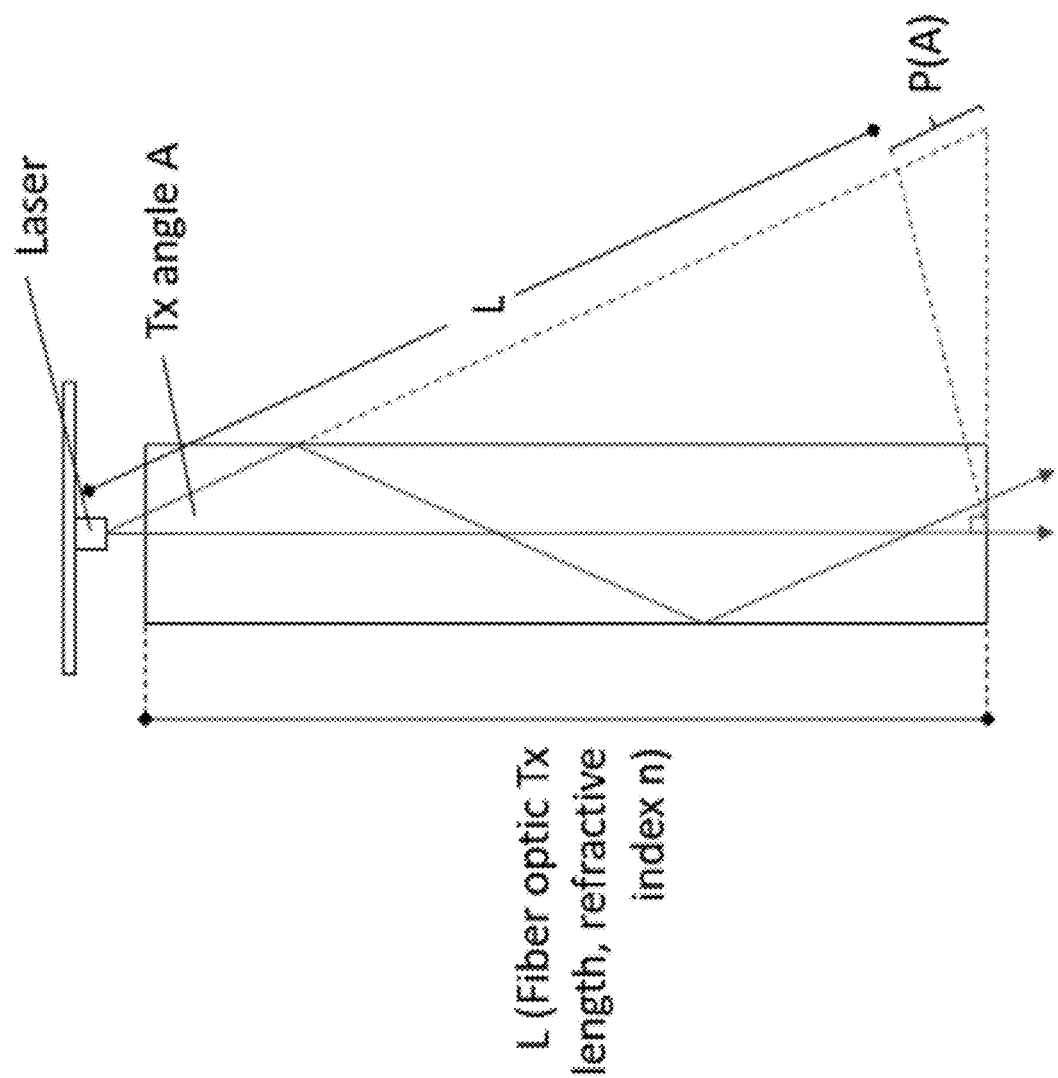
FIG. 14 schematically illustrates a method for depth correction based on an entry angle of a TOF light transmitted through a fiber optic cable, in accordance with some embodiments.

FIG. 14 illustrates a depth correction method based on an angle of entry of the TOF light into a fiber optic cable or a light guide. In some cases, when TOF light is provided to a fiber optic cable or light guide, the TOF light may enter the light guide at an angle A. Light emitted at an angle A may travel an extra distance P(A). The corrected travel distance $D_{corrected}$ may be computed as a function of the raw travel distance $D_{raw}$ and the extra distance P(A):

$$D_{corrected} = D_{raw} - P(A)$$

The relationship between angle A, the extra distance P(A), the length L of the fiber optic cable through which light is transmitted, and the refractive index n of the fiber optic cable may be expressed as follows:

$$\sin(pi/2 - A)/(L*n) = \sin(90)/(L*n + P(A))$$

This mathematical relationship may be simplified to the following expression:

$$P(A) = L*n(\sec(A) - 1)$$

Therefore, the relationship between the corrected travel distance $D_{corrected}$, the raw travel distance $D_{raw}$, the length L of the fiber optic cable, and the light entry angle A may be expressed as follows:

$$D_{corrected} = D_{raw} - L*(\sec(A) - 1).$$

The corrected travel distance $D_{corrected}$ may be used to perform image calibration and to correct distortions in a depth map caused by the angled entry of TOF light into the fiber optic cable.

Computer Systems

Figure 10:
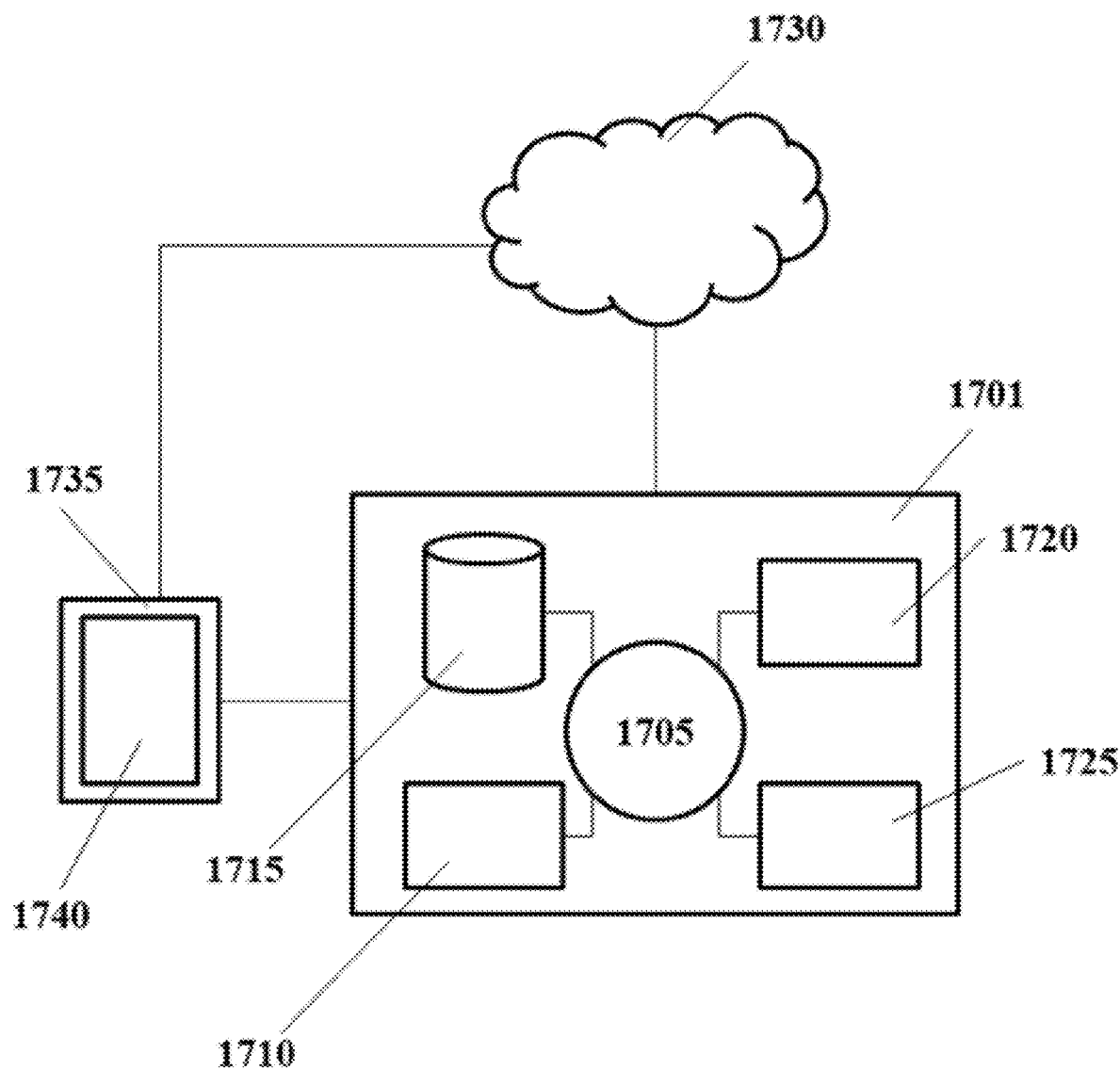
FIG. 10 schematically illustrates a computer system that is programmed or otherwise configured to implement methods provided herein.

In an aspect, the present disclosure provides computer systems that are programmed or otherwise configured to implement methods of the disclosure, e.g., any of the subject methods for medical imaging. FIG. 10 shows a computer system 1701 that is programmed or otherwise configured to implement a method for medical imaging. The computer system 1701 may be configured to, for example, (i) direct an illumination source to combine white light with coherent laser light to generate a combined light beam, (ii) direct the illumination source to provide the combined light beam to through an elongated scope and towards the scope assembly, and (iii) direct at least one sensor of an imaging unit of the scope assembly to receive at least a portion of a light signal that is reflected or emitted by one or more locations within a subject's body upon illumination by at least a portion of the combined light beam. The computer system 1701 can be an electronic device of a user or a computer system that is remotely located with respect to the electronic device. The electronic device can be a mobile electronic device.

The computer system 1701 may include a central processing unit (CPU, also "processor" and "computer processor" herein) 1705, which can be a single core or multi core processor, or a plurality of processors for parallel processing. The computer system 1701 also includes memory or memory location 1710 (e.g., random-access memory, read-only memory, flash memory), electronic storage unit 1715 (e.g., hard disk), communication interface 1720 (e.g., network adapter) for communicating with one or more other systems, and peripheral devices 1725, such as cache, other memory, data storage and/or electronic display adapters. The memory 1710, storage unit 1715, interface 1720 and peripheral devices 1725 are in communication with the CPU 1705 through a communication bus (solid lines), such as a motherboard. The storage unit 1715 can be a data storage unit (or data repository) for storing data. The computer system 1701 can be operatively coupled to a computer network ("network") 1730 with the aid of the communication interface 1720. The network 1730 can be the Internet, an internet and/or extranet, or an intranet and/or extranet that is in communication with the Internet. The network 1730 in some cases is a telecommunication and/or data network. The network 1730 can include one or more computer servers, which can enable distributed computing, such as cloud computing. The network 1730, in some cases with the aid of the computer system 1701, can implement a peer-to-peer network, which may enable devices coupled to the computer system 1701 to behave as a client or a server.

The CPU 1705 can execute a sequence of machine-readable instructions, which can be embodied in a program or software. The instructions may be stored in a memory location, such as the memory 1710. The instructions can be directed to the CPU 1705, which can subsequently program or otherwise configure the CPU 1705 to implement methods of the present disclosure. Examples of operations performed by the CPU 1705 can include fetch, decode, execute, and writeback.

The CPU 1705 can be part of a circuit, such as an integrated circuit. One or more other components of the system 1701 can be included in the circuit. In some cases, the circuit is an application specific integrated circuit (ASIC).

The storage unit 1715 can store files, such as drivers, libraries and saved programs. The storage unit 1715 can store user data, e.g., user preferences and user programs. The computer system 1701 in some cases can include one or more additional data storage units that are located external to the computer system 1701 (e.g., on a remote server that is in communication with the computer system 1701 through an intranet or the Internet).

The computer system 1701 can communicate with one or more remote computer systems through the network 1730. For instance, the computer system 1701 can communicate with a remote computer system of a user (e.g., a subject, an end user, a consumer, a healthcare provider, an imaging technician, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1701 via the network 1730.

Methods as described herein can be implemented by way of machine (e.g., computer processor) executable code stored on an electronic storage location of the computer system 1701, such as, for example, on the memory 1710 or electronic storage unit 1715. The machine executable or machine readable code can be provided in the form of software. During use, the code can be executed by the processor 1705. In some cases, the code can be retrieved from the storage unit 1715 and stored on the memory 1710 for ready access by the processor 1705. In some situations, the electronic storage unit 1715 can be precluded, and machine-executable instructions are stored on memory 1710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1701 can include or be in communication with an electronic display 1735 that comprises a user interface (UI) 1740 for providing, for example, a portal for a healthcare provider or an imaging technician to monitor or track one or more features of the optical adapter (e.g., coupling to the scope, coupling to the camera, the image sensor, the optics assembly, etc.). The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1705.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A scope assembly, comprising:
   an elongated scope;
   an imaging unit operably coupled to a distal tip of the elongated scope, wherein the imaging unit is configured to move relative to the elongated scope and obtain a plurality of imaging data of a target site from a plurality of perspectives using at least two imaging sensors having different optical axes;
   one or more motion sensors within the imaging unit, wherein the one or more motion sensors are configured to provide spatial information of the imaging unit as the imaging unit moves relative to the elongated scope; and
   a processor operatively coupled to the imaging unit and the sensors, wherein the processor is configured to generate a three-dimensional (3D) reconstruction of the target site based on the plurality of imaging data and the spatial information.

2. The scope assembly of claim 1, wherein the one or more motion sensors are configured to sense one of position, orientation, or acceleration of at least a portion of the scope assembly.

3. The scope assembly of claim 1 wherein the one or more motion sensors comprise:
   a first motion sensor configured to detect and record one of position, orientation, or acceleration of an imaging unit arm coupled to the imaging unit; and
   a second motion sensor configured to detect and record one of position, orientation, or acceleration of the imaging unit.

4. The scope assembly of claim 1, wherein the one or more motion sensors comprise an inertial measurement unit.

5. The scope assembly of claim 1, wherein the one or more motion sensors are further configured to provide spatiotemporal information of the imaging unit.

6. The scope assembly of claim 1, wherein the one or more motion sensors are further configured to measure movement of the imaging unit relative to at least a portion of the elongated scope.

7. The scope assembly of claim 6, wherein the measured movement comprises spatiotemporal movement of the imaging unit.

8. The scope assembly of claim 6, wherein the measured movement is combined with the imaging data to produce the 3D reconstruction of the target site.

9. The scope assembly of claim 1, wherein the imaging unit is configured to move relative to the elongated scope via one or more joint mechanisms, and wherein the one or more motion sensors are operatively coupled to the one or more joint mechanisms.

10. The scope assembly of claim 9, wherein the imaging unit comprises a plurality of joint mechanisms, and wherein an individual joint mechanism of the plurality of joint mechanisms comprises at least one motion sensor.

11. A method comprising:
    providing a scope assembly including (i) an elongated scope, (ii) an imaging unit operatively coupled to a distal tip of the elongated scope, and (iii) one or more motion sensors operatively coupled to the imaging unit;
    moving the imaging unit relative to the elongated scope to obtain a plurality of imaging data of a target site from a plurality of perspectives using at least two imaging sensors having different optical axes;
    providing spatial information of the imaging unit using the motion sensors within the imaging unit as the imaging unit moves relative to the elongated scope; and
    generating a three-dimensional (3D) reconstruction of the target site using a processor based on the plurality of imaging data and the spatial information.

12. The method of claim 11, wherein providing the spatial information further comprises:
sensing one of position, orientation, or acceleration of the imaging unit.

13. The method of claim 11, wherein the one or more motion sensors comprise an inertial measurement unit.

14. The method of claim 11, wherein providing the spatial information further comprises providing the spatial information using spatiotemporal information of the imaging unit.

15. The method of claim 11 wherein providing the spatial information further comprises measuring movement of the imaging unit relative to at least a portion of the elongated scope.

16. The method of claim 15 wherein the measured movement comprises spatiotemporal movement of the imaging unit.

17. The method of claim 15 wherein generating the 3D reconstruction of the target site further comprises combining the measured movement with the imaging data to produce the 3D reconstruction of the target site.

18. The method of claim 11, wherein moving the imaging unit relative to the elongated scope further comprises moving the imaging unit via one or more joint mechanisms.

19. The method of claim 18, wherein the one or more joint mechanisms includes a plurality of joint mechanisms at least one of which has a motion sensor.

20. A scope assembly, comprising:
an elongated scope;
an imaging unit operably coupled to a distal tip of the elongated scope, wherein the imaging unit is configured to (i) move relative to the elongated scope via one or more joint mechanisms and (ii) obtain a plurality of imaging data of a target site from a plurality of perspectives using at least two imaging sensors having different optical axes;
one or more motion sensors within the imaging unit and the joint mechanisms, wherein the one or more motion sensors are configured to provide spatiotemporal information of the imaging unit as the imaging unit moves relative to the elongated scope; and
a processor operatively coupled to the imaging unit and the sensors, wherein the processor is configured to generate a three-dimensional (3D) reconstruction of the target site based on the plurality of imaging data and the spatiotemporal information.

* * * * *